US006387697B1

(12) United States Patent
Yuqiu et al.

(10) Patent No.: US 6,387,697 B1
(45) Date of Patent: May 14, 2002

(54) COMPOSITIONS FOR TREATMENT AND DIAGNOSIS OF BREAST CANCER AND METHODS FOR THEIR USE

(75) Inventors: Jiang Yuqiu, Kent; Davin C. Dillon; Jennifer L. Mitcham, both of Redmond; Jiangchun Xu, Bellevue, all of WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/222,575

(22) Filed: Dec. 28, 1998

(51) Int. Cl.[7] .................................................. C12N 5/00

(52) U.S. Cl. ................. 435/325; 435/320.1; 435/252.3; 435/254.2; 536/24.3; 536/23.5

(58) Field of Search ............................... 536/23.1, 23.5, 536/23.4, 24.3, 24.31, 24.33; 435/320.1, 455, 325, 243, 69.1, 6, 252.3, 254.2; 424/184.1, 192.1; 514/44

(56) References Cited

U.S. PATENT DOCUMENTS

| | | | |
|---|---|---|---|
| 4,962,187 A | 10/1990 | Pant | 530/350 |
| 5,215,926 A | 6/1993 | Etchells, III et al. | 436/501 |
| 5,240,856 A | 8/1993 | Goffe et al. | 435/299 |
| 5,986,170 A | 11/1999 | Subjeck | 800/2 |

FOREIGN PATENT DOCUMENTS

| | | |
|---|---|---|
| WO | WO 89/06280 | 7/1989 |
| WO | WO 91/16116 | 10/1991 |
| WO | WO 91/16629 | 10/1991 |
| WO | WO 92/07243 | 4/1992 |
| WO | WO 96/29430 | 9/1996 |
| WO | WO 98/33915 | 8/1998 |
| WO | WO 98/54963 | 12/1998 |
| WO | WO 99/09155 | 2/1999 |

OTHER PUBLICATIONS

GenBank Accession No. AI272025.1 Nov. 17, 1998.*

Watson et al., Methods of Creating Recombinant DNA Molecules, (Recombinant DNA Second Edition, pp. 63–77) 1994.*

Chang and Shu, "Current status of adoptive immunotherapy of cancer," *Critical Reviews in Oncology/Hematology 22* (3):213–228, Apr. 1996.

Cheever and Chen, "Therapy with cultured T cells: principles revisited," *Immunological Reviews*, 157: 177–194, 1997.

Cheever et al., "Potential uses of interleukin 2 in cancer therapy," *Immunobiol*, 172:365–382, 1986.

Durrant L., "Cancer vaccines," *Anti–Cancer Drugs*, 8:727–733, 1997.

Porter–Jordan and Lippman, "Overview of the biologic markers of breast cancer," *Breast Cancer 8*:(1):73–100, Feb. 1994.

Wei et al., "Protection against mammary tumor growth by vaccination with full–length, modified human ErbB–2 DNA," *Int. J. Cancer*, 81:748–754, 1999.

Stratagene 1991 product catalog, Prime–It™ Random Primer Labeling Kit, Catalog No. 300387, p. 66.*

* cited by examiner

*Primary Examiner*—John S. Brusca
(74) *Attorney, Agent, or Firm*—Seed Intellectual Property Law Group PLLC

(57) ABSTRACT

Compounds and methods for the treatment and diagnosis of breast cancer are provided. The inventive compounds include polypeptides containing at least a portion of a breast tumor antigen. Vaccines and pharmaceutical compositions for immunotherapy of breast cancer comprising such polypeptides, or polynucleotides encoding such polypeptides, are provided, together with polynucleotides for preparing the inventive polypeptides. The inventive polypeptides may be used to generate antibodies useful for the diagnosis and monitoring of breast cancer.

12 Claims, 1 Drawing Sheet

SYN18C6 Northern Blot

Figure 1:
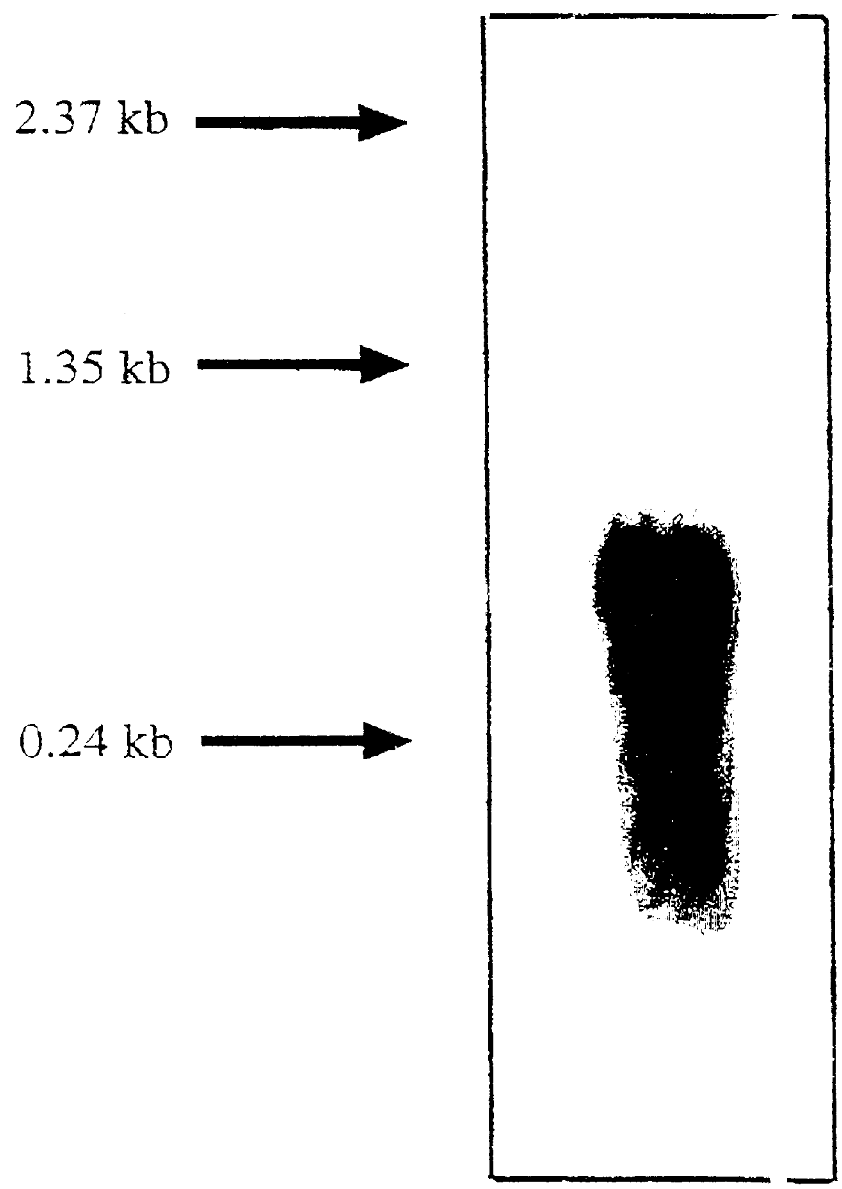

COMPOSITIONS FOR TREATMENT AND DIAGNOSIS OF BREAST CANCER AND METHODS FOR THEIR USE

TECHNICAL FIELD

The present invention relates generally to compositions and methods for the treatment of breast cancer. The invention is more particularly related to polypeptides comprising at least a portion of a protein that is preferentially expressed in breast tumor tissue and to polynucleotides encoding such polypeptides. Such polypeptides may be used in vaccines and pharmaceutical compositions for treatment of breast cancer.

BACKGROUND OF THE INVENTION

Breast cancer is a significant health problem for women in the United States and throughout the world. Although advances have been made in detection and treatment of the disease, breast cancer remains the second leading cause of cancer—related deaths in women, affecting more than 180, 000 women in the United States each year. For women in North America, the life-time odds of getting breast cancer are one in eight.

No vaccine or other universally successful method for the prevention or treatment of breast cancer is currently available. Management of the disease currently relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific tumor markers. See, e.g., Porter-Jordan and Lippman, *Breast Cancer* 8:73–100 (1994). However, the use of established markers often leads to a result that is difficult to interpret, and the high mortality observed in breast cancer patients indicates that improvements are needed in the treatment, diagnosis and prevention of the disease.

Accordingly, there is a need in the art for improved methods for the treatment and diagnosis of breast cancer. The present invention fulfills these needs and further provides other related advantages.

SUMMARY OF THE INVENTION

The present invention provides compounds and methods for the treatment and diagnosis of breast cancer. In one aspect, isolated polypeptides are provided comprising at least an immunogenic portion of a breast tumor antigen or a variant thereof, wherein the antigen comprises an amino acid sequence encoded by a polynucleotide having a sequence selected from the group consisting of: (a) nucleotide sequences recited in SEQ ID NO: 1–61 and 63–174; (b) complements of said nucleotide sequences; and (c) sequences that hybridize to a sequence of (a) or (b) under moderately stringent conditions.

In related aspects, isolated polynucleotides encoding the above polypeptides are provided. In specific embodiments, such polynucleotides comprise a sequence selected from the group consisting of sequences provided in SEQ ID NO: 1–61 and 63–174. The present invention further provides expression vectors comprising the above polynucleotides, together with host cells transformed or transfected with such expression vectors. In preferred embodiments, the host cells are selected from the group consisting of *E. coli*, yeast and mammalian cells.

In another aspect, the present invention provides fusion proteins comprising a first and a second inventive polypeptide or, alternatively, an inventive polypeptide and a known breast tumor antigen.

The present invention also provides pharmaceutical compositions comprising at least one of the above polypeptides, or a polynucleotide encoding such a polypeptide, and a physiologically acceptable carrier, together with vaccines comprising at least one such polypeptide or polynucleotide in combination with a non-specific immune response enhancer. Pharmaceutical compositions and vaccines comprising one or more of the above fusion proteins are also provided.

In yet another aspect, methods are provided for inhibiting the development of breast cancer in a patient, comprising administering an effective amount of at least one of the above pharmaceutical compositions and/or vaccines.

The polypeptides disclosed herein may be usefully employed in the diagnosis and monitoring of breast cancer. In one aspect of the present invention, methods are provided for detecting breast cancer in a patient, comprising: (a) contacting a biological sample obtained from a patient with a binding agent that is capable of binding to one of the above polypeptides; and (b) detecting in the sample a protein or polypeptide that binds to the binding agent. In preferred embodiments, the binding agent is an antibody, most preferably a monoclonal antibody.

In related aspects, methods are provided for monitoring the progression of breast cancer in a patient, comprising: (a) contacting a biological sample obtained from a patient with a binding agent that is capable of binding to one of the above polypeptides; (b) determining in the sample an amount of a protein or polypeptide that binds to the binding agent; (c) repeating steps (a) and (b); and comparing the amounts of polypeptide detected in steps (b) and (c).

Within related aspects, the present invention provides antibodies, preferably monoclonal antibodies, that bind to the inventive polypeptides, as well as diagnostic kits comprising such antibodies, and methods of using such antibodies to inhibit the development of breast cancer.

The present invention further provides methods for detecting breast cancer comprising: (a) obtaining a biological sample from a patient; (b) contacting the sample with a first and a second oligonucleotide primer in a polymerase chain reaction, at least one of the oligonucleotide primers being specific for a polynucleotide that encodes one of the above polypeptides; and (c) detecting in the sample a DNA sequence that amplifies in the presence of the first and second oligonucleotide primers. In a preferred embodiment, at least one of the oligonucleotide primers comprises at least about 10 contiguous nucleotides of a polynucleotide comprising a sequence elected from the group consisting of SEQ ID NO: 1–61 and 63–174.

In a further aspect the present invention provides a method for detecting breast cancer in a patient comprising: (a) obtaining a biological sample from the patient; (b) contacting the sample with an oligonucleotide probe specific for a polynucleotide that encodes one of the above polypeptides; and (c) detecting in the sample a DNA sequence that hybridizes to the oligonucleotide probe. Preferably, the oligonucleotide probe comprises at least about 15 contiguous nucleotides of a polynucleotide comprising a sequence selected from the group consisting of SEQ ID NO: 1–61 and 63–174.

In related aspects, diagnostic kits comprising the above oligonucleotide probes or primers are provided.

These and other aspects of the present invention will become apparent upon reference to the following detailed description. All references disclosed herein are hereby incorporated by reference in their entirety as if each was incorporated individually.

BRIEF DESCRIPTION OF THE DRAWING AND SEQUENCE IDENTIFIERS

FIG. 1 shows the results of a Northern blot of the clone SYN18C6 (SEQ ID NO: 40).

SEQ ID NO: 1 is the determined cDNA sequence of JBT2.

SEQ ID NO: 2 is the determined cDNA sequence of JBT6.

SEQ ID NO: 3 is the determined cDNA sequence of JBT7.

SEQ ID NO: 4 is the determined cDNA sequence of JBT10.

SEQ ID NO: 5 is the determined cDNA sequence of JBT13.

SEQ ID NO: 6 is the determined cDNA sequence of JBT14.

SEQ ID NO: 7 is the determined cDNA sequence of JBT15.

SEQ ID NO: 8 is the determined cDNA sequence of JBT16.

SEQ ID NO: 9 is the determined cDNA sequence of JBT17.

SEQ ID NO: 10 is the determined cDNA sequence of JBT22.

SEQ ID NO: 11 is the determined cDNA sequence of JBT25.

SEQ ID NO: 12 is the determined cDNA sequence of JBT28.

SEQ ID NO: 13 is the determined cDNA sequence of JBT32.

SEQ ID NO: 14 is the determined cDNA sequence of JBT33.

SEQ ID NO: 15 is the determined cDNA sequence of JBT34.

SEQ ID NO: 16 is the determined cDNA sequence of JBT36.

SEQ ID NO: 17 is the determined cDNA sequence of JBT37.

SEQ ID NO: 18 is the determined cDNA sequence of JBT51.

SEQ ID NO: 19 is the determined cDNA sequence of JBTT1.

SEQ ID NO: 20 is the determined cDNA sequence of JBTT7.

SEQ ID NO: 21 is the determined cDNA sequence of JBTT11.

SEQ ID NO: 22 is the determined cDNA sequence of JBTT14.

SEQ ID NO: 23 is the determined cDNA sequence ofJBTT18.

SEQ ID NO: 24 is the determined cDNA sequence of JBTT19.

SEQ ID NO: 25 is the determined cDNA sequence of JBTT20.

SEQ ID NO: 26 is the determined cDNA sequence of JBTT21.

SEQ ID NO: 27 is the determined cDNA sequence of JBTT22.

SEQ ID NO: 28 is the determined cDNA sequence of JBTT28.

SEQ ID NO: 29 is the determined cDNA sequence of JBTT29.

SEQ ID NO: 30 is the determined cDNA sequence of JBTT33.

SEQ ID NO: 31 is the determined cDNA sequence of JBTT37.

SEQ ID NO: 32 is the determined cDNA sequence of JBTT38.

SEQ ID NO: 33 is the determined cDNA sequence of JBTT47.

SEQ ID NO: 34 is the determined cDNA sequence of JBTT48.

SEQ ID NO: 35 is the determined cDNA sequence of JBTT50.

SEQ ID NO: 36 is the determined cDNA sequence of JBTT51.

SEQ ID NO: 37 is the determined cDNA sequence of JBTT52.

SEQ ID NO: 38 is the determined cDNA sequence of JBTT54.

SEQ ID NO: 39 is the determined cDNA sequence of SYN17F4.

SEQ ID NO: 40 is the determined cDNA sequence of SYN18C6.

SEQ ID NO: 41 is the determined cDNA sequence of SYN19A2.

SEQ ID NO: 42 is the determined cDNA sequence of SYN19C8.

SEQ ID NO: 43 is the determined cDNA sequence of SYN20A12.

SEQ ID NO: 44 is the determined cDNA sequence of SYN20G6.

SEQ ID NO: 45 is the determined cDNA sequence of SYN20G6–2.

SEQ ID NO: 46 is the determined cDNA sequence of SYN21B9.

SEQ ID NO: 47 is the determined cDNA sequence of SYN21B9–2.

SEQ ID NO: 48 is the determined cDNA sequence of SYN21C10.

SEQ ID NO: 49 is the determined cDNA sequence of SYN21G10.

SEQ ID NO: 50 is the determined cDNA sequence of SYN21G10–2.

SEQ ID NO: 51 is the determined cDNA sequence of SYN21G11.

SEQ ID NO: 52 is the determined cDNA sequence of SYN21G11–2.

SEQ ID NO: 53 is the determined cDNA sequence of SYN21H8.

SEQ ID NO: 54 is the determined cDNA sequence of SYN22A10.

SEQ ID NO: 55 is the determined cDNA sequence of SYN22A10–2.

SEQ ID NO: 56 is the determined cDNA sequence of SYN22A12.

SEQ ID NO: 57 is the determined cDNA sequence of SYN22A2.

SEQ ID NO: 58 is the determined cDNA sequence of SYN22B4.

SEQ ID NO: 59 is the determined cDNA sequence of SYN22C2.

SEQ ID NO: 60 is the determined cDNA sequence of SYN22E10.

SEQ ID NO: 61 is the determined cDNA sequence of SYN22F2.

SEQ ID NO: 62 is a predicted amino acid sequence for SYN18C6.

SEQ ID NO: 63 is the determined cDNA sequence of B723P.

SEQ ID NO: 64 is the determined cDNA sequence for B724P.

SEQ ID NO: 65 is the determined cDNA sequence of B770P.

SEQ ID NO: 66 is the determined cDNA sequence of B716P.

SEQ ID NO: 67 is the determined cDNA sequence of B725P.

SEQ ID NO: 68 is the determined cDNA sequence of B717P.

SEQ ID NO: 69 is the determined cDNA sequence of B771P.

SEQ ID NO: 70 is the determined cDNA sequence of B722P.

SEQ ID NO: 71 is the determined cDNA sequence of B726P.

SEQ ID NO: 72 is the determined CDNA sequence of B727P.

SEQ ID NO: 73 is the determined cDNA sequence of B728P.

SEQ ID NO: 74–87 are the determined cDNA sequences of isolated clones which show homology to known sequences.

SEQ ID NO: 88 is the determined cDNA sequence of 13053.

SEQ ID NO: 89 is the determined cDNA sequence of 13057.

SEQ ID NO: 90 is the determined cDNA sequence of 13059.

SEQ ID NO: 91 is the determined cDNA sequence of 13065.

SEQ ID NO: 92 is the determined cDNA sequence of 13067.

SEQ ID NO: 93 is the determined cDNA sequence of 13068.

SEQ ID NO: 94 is the determined cDNA sequence of 13071.

SEQ ID NO: 95 is the determined cDNA sequence of 13072.

SEQ ID NO: 96 is the determined cDNA sequence of 13073.

SEQ ID NO: 97 is the determined cDNA sequence of 13075.

SEQ ID NO: 98 is the determined cDNA sequence of 13078.

SEQ ID NO: 99 is the determined cDNA sequence of 13079.

SEQ ID NO: 100 is the determined cDNA sequence of 13081.

SEQ ID NO: 101 is the determined cDNA sequence of 13082.

SEQ ID NO: 102 is the determined cDNA sequence of 13092.

SEQ ID NO: 103 is the determined cDNA sequence of 13097.

SEQ ID NO: 104 is the determined cDNA sequence of 13101.

SEQ ID NO: 105 is the determined cDNA sequence of 13102.

SEQ ID NO: 106 is the determined cDNA sequence of 13119.

SEQ ID NO: 107 is the determined cDNA sequence of 13131.

SEQ ID NO: 108 is the determined cDNA sequence of 13133.

SEQ ID NO: 109 is the determined cDNA sequence of 13135.

SEQ ID NO: 110 is the determined cDNA sequence of 13139.

SEQ ID NO: 111 is the determined cDNA sequence of 13140.

SEQ ID NO: 112 is the determined cDNA sequence of 13146.

SEQ ID NO: 113 is the determined cDNA sequence of 13147.

SEQ ID NO: 114 is the determined cDNA sequence of 13148.

SEQ ID NO: 115 is the determined cDNA sequence of 13149.

SEQ ID NO: 116 is the determined cDNA sequence of 13151.

SEQ ID NO: 117 is the determined cDNA sequence of 13051

SEQ ID NO: 118 is the determined cDNA sequence of 13052

SEQ ID NO: 119 is the determined cDNA sequence of 13055

SEQ ID NO: 120 is the determined cDNA sequence of 13058

SEQ ID NO: 121 is the determined cDNA sequence of 13062

SEQ ID NO: 122 is the determined cDNA sequence of 13064

SEQ ID NO: 123 is the determined cDNA sequence of 13080

SEQ ID NO: 124 is the determined cDNA sequence of 13093

SEQ ID NO: 125 is the determined cDNA sequence of 13094

SEQ ID NO: 126 is the determined cDNA sequence of 13095

SEQ ID NO: 127 is the determined cDNA sequence of 13096

SEQ ID NO: 128 is the determined cDNA sequence of 13099

SEQ ID NO: 129 is the determined cDNA sequence of 13100

SEQ ID NO: 130 is the determined cDNA sequence of 13103

SEQ ID NO: 131 is the determined cDNA sequence of 13106

SEQ ID NO: 132 is the determined cDNA sequence of 13107

SEQ ID NO: 133 is the determined cDNA sequence of 13108

SEQ ID NO: 134 is the determined cDNA sequence of 13121

SEQ ID NO: 135 is the determined cDNA sequence of 13126

SEQ ID NO: 136 is the determined cDNA sequence of 13129

SEQ ID NO: 137 is the determined cDNA sequence of 13130

SEQ ID NO: 138 is the determined cDNA sequence of 13134

SEQ ID NO: 139 is the determined cDNA sequence of 13141

SEQ ID NO: 140 is the determined cDNA sequence of 13142

SEQ ID NO: 141 is the determined cDNA sequence of 14376

SEQ ID NO: 142 is the determined cDNA sequence of 14377

SEQ ID NO: 143 is the determined cDNA sequence of 14383

SEQ ID NO: 144 is the determined cDNA sequence of 14384

SEQ ID NO: 145 is the determined cDNA sequence of 14387

SEQ ID NO: 146 is the determined cDNA sequence of 14392

SEQ ID NO: 147 is the determined cDNA sequence of 14394

SEQ ID NO: 148 is the determined cDNA sequence of 14398

SEQ ID NO: 149 is the determined cDNA sequence of 14401

SEQ ID NO: 150 is the determined cDNA sequence of 14402

SEQ ID NO: 151 is the determined cDNA sequence of 14405

SEQ ID NO: 152 is the determined cDNA sequence of 14409

SEQ ID NO: 153 is the determined cDNA sequence of 14412

SEQ ID NO: 154 is the determined cDNA sequence of 14414

SEQ ID NO: 155 is the determined cDNA sequence of 14415

SEQ ID NO: 156 is the determined cDNA sequence of 14416

SEQ ID NO: 157 is the determined cDNA sequence of 14419

SEQ ID NO: 158 is the determined cDNA sequence of 14426

SEQ ID NO: 159 is the determined cDNA sequence of 14427

SEQ ID NO: 160 is the determined cDNA sequence of 14375

SEQ ID NO: 161 is the determined cDNA sequence of 14378

SEQ ID NO: 162 is the determined cDNA sequence of 14379

SEQ ID NO: 163 is the determined cDNA sequence of 14380

SEQ ID NO: 164 is the determined cDNA sequence of 14381

SEQ ID NO: 165 is the determined cDNA sequence of 14382

SEQ ID NO: 166 is the determined cDNA sequence of 14388

SEQ ID NO: 167 is the determined cDNA sequence of 14399

SEQ ID NO: 168 is the determined cDNA sequence of 14406

SEQ ID NO: 169 is the determined cDNA sequence of 14407

SEQ ID NO: 170 is the determined cDNA sequence of 14408

SEQ ID NO: 171 is the determined cDNA sequence of 14417

SEQ ID NO: 172 is the determined cDNA sequence of 14418

SEQ ID NO: 173 is the determined cDNA sequence of 14423

SEQ ID NO: 174 is the determined cDNA sequence of 14424

DETAILED DESCRIPTION OF THE INVENTION

As noted above, the present invention is generally directed to compositions and methods for the treatment and diagnosis of breast cancer. The inventive compositions are generally isolated polypeptides that comprise at least a portion of a breast tumor antigen. Also included within the present invention are molecules (such as an antibody or fragment thereof) that bind to the inventive polypeptides. Such molecules are referred to herein as "binding agents."

In particular, the subject invention discloses polypeptides comprising at least a portion of a human breast tumor antigen, or a variant thereof, wherein the breast tumor antigen includes an amino acid sequence encoded by a polynucleotide including a sequence selected from the group consisting of: nucleotide sequences recited in SEQ ID NO: 1–61, 63–73, 88–117 and 142–160, the complements of said nucleotide sequences, and variants thereof. As used herein, the term "polypeptide" encompasses amino acid chains of any length, including full length proteins, wherein the amino acid residues are linked by covalent peptide bonds. Thus, a polypeptide comprising a portion of one of the above breast antigens may consist entirely of the portion, or the portion may be present within a larger polypeptide that contains additional sequences. The additional sequences may be derived from the native protein or may be heterologous, and such sequences may be immunoreactive and/or antigenic.

As used herein, an "immunogenic portion" of a human breast tumor antigen is a portion that is capable of eliciting an immune response in a patient inflicted with breast cancer and as such binds to antibodies present within sera from a breast cancer patient. Such immunogenic portions generally comprise at least about 5 amino acid residues, more preferably at least about 10, and most preferably at least about 20 amino acid residues. Immunogenic portions of the proteins described herein may be identified in antibody binding assays. Such assays may generally be performed using any of a variety of means known to those of ordinary skill in the art, as described, for example, in Harlow and Lane, *Antibodies: A Laboratory Manual,* Cold Spring Harbor Laboratory, Cold Spring Harbor, N.Y., 1988. For example, a polypeptide may be immobilized on a solid support (as described below) and contacted with patient sera to allow binding of antibodies within the sera to the immobilized polypeptide. Unbound sera may then be removed and bound antibodies detected using, for example, $^{125}$ 1-labeled Protein A. Alternatively, a polypeptide may be used to generate monoclonal and polyclonal antibodies for use in detection of the polypeptide in blood or other fluids of breast cancer patients. Methods for preparing and identifying immunogenic portions of antigens of known sequence are well known in the art and include those summarized in Paul, *Fundamental Immunology,* 3$^{rd}$ ed., Raven Press, 1993, pp. 243–247.

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HNRNA molecule contains introns and corresponds to a polynucleotide in a generally one-to-one manner. An mRNA molecule corresponds to an HnRNA and polynucleotide from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments.

The compositions and methods of the present invention also encompass variants of the above polypeptides and polynucleotides. Such variants include, but are not limited to, naturally occurring allelic variants of the inventive sequences.

A polypeptide "variant," as used herein, is a polypeptide that differs from the recited polypeptide only in conservative substitutions and/or modifications, such that the antigenic properties of the polypeptide are retained. In a preferred embodiment, variant polypeptides differ from an identified sequence by substitution, deletion or addition of five amino acids or fewer. Such variants may generally be identified by modifying one of the above polypeptide sequences, and evaluating the antigenic properties of the modified polypeptide using, for example, the representative procedures described herein. Polypeptide variants preferably exhibit at least about 70%, more preferably at least about 90% and most preferably at least about 95% identity (determined as described below) to the identified polypeptides.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

A nucleotide "variant" is a sequence that differs from the recited nucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (DNA, 2:183, 1983). Nucleotide variants may be naturally occurring allelic variants, or non-naturally occurring variants. Variant nucleotide sequences preferably exhibit at least about 70%, more preferably at least about 80% and most preferably at least about 90% identity (determined as described below) to the recited sequence.

The breast tumor antigens provided by the present invention include variants that are encoded by DNA sequences which are substantially homologous to one or more of the DNA sequences specifically recited herein. "Substantial homology," as used herein, refers to DNA sequences that are capable of hybridizing under moderately stringent conditions. Suitable moderately stringent conditions include prewashing in a solution of 5X SSC, 0.5% SDS, 1.0 mM EDTA (pH 8.0); hybridizing at 50° C.—65° C., 5X SSC, overnight or, in the event of cross-species homology, at 45° C. with 0.5X SSC; followed by washing twice at 65° C. for 20 minutes with each of 2X, 0.5X and 0.2X SSC containing 0.1% SDS. Such hybridizing DNA sequences are also within the scope of this invention, as are nucleotide sequences that, due to code degeneracy, encode an immunogenic polypeptide that is encoded by a hybridizing DNA sequence.

Two nucleotide or polypeptide sequences are said to be "identical" if the sequence of nucleotides or amino acid residues in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, Mo. (1978) A model of evolutionary change in proteins —Matrices for detecting distant relationships. In Dayhoff, Mo. (ed.) Atlas of Protein Sequence and Structure, National Biomedical Resarch Foundaiton, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D.G. and Sharp, P.M. (1989) Fast and sensitive multiple sequence alignments on a microcomputer CABIOS 5:151–153; Myers, E.W. and Muller W. (1988) Optimal alignments in linear space CABIOS 4:11–17; Robinson, E.D. (1971) *Comb. Theor* 11:105; Santou, N. Nes, M. (1987) The neighbor joining method. A new method for reconstructing phylogenetic trees *Mol. Biol. EvoL* 4:406–425; Sneath, P.H.A. and Sokal, R.R. (1973) *Numerical Taxonomy —the Principles and Practice of Numerical Taxonomy,* Freeman Press, San Francisco, Calif.; Wilbur, W.J. and Lipman, D.J. (1983) Rapid similarity searches of nucleic acid and protein data banks *Proc. Natl. Acad, Sci. USA* 80:726–730.

Preferably, the "percentage of sequence identity" is determined by comparing two optimally aligned sequences over a window of comparison of at least 20 positions, wherein the portion of the polynucleotide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

The breast tumor antigens of the present invention, and polynucleotides encoding such antigens, may be isolated from breast tumor tissue using any of a variety of methods well known in the art. DNA sequences corresponding to a gene (or a portion thereof) encoding one of the inventive breast tumor antigens may be isolated from a breast tumor cDNA library using a subtraction technique as described in detail below. Examples of such DNA sequences are provided in SEQ ID NO: 1–61 and 63–174. Partial DNA sequences thus obtained may be used to design oligonucleotide primers for the amplification of full-length DNA sequences in a polymerase chain reaction (PCR), using techniques well known in the art (see, for example, MuHis et al., *Cold Spring Harbor Symp. Quant. BioL,* 51:263, 1987; Erlich ed., *PCR Technology,* Stockton Press, N.Y., 1989). Once a DNA sequence encoding a polypeptide is obtained, any of the above modifications may be readily introduced using standard mutagenesis techniques, such as oligonucleotide-directed site-specific mutagenesis as taught, for example, by Adelman et al. (DNA, 2:183, 1983).

The breast tumor polypeptides disclosed herein may also be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain (see, for example, Merrifield, *J. Am. Chem. Soc.* 85:2149–2146, 1963). Equipment for automated synthesis of polypeptides is commercially available from suppliers such as Perkin Elmer/Applied BioSystems Division (Foster City, Calif.), and may be operated according to the manufacturer's instructions.

Alternatively, any of the above polypeptides may be produced recombinantly by inserting a DNA sequence that encodes the polypeptide into an expression vector and expressing the protein in an appropriate host. Any of a variety of expression vectors known to those of ordinary skill in the art may be employed to express recombinant polypeptides of this invention. Expression may be achieved in any appropriate host cell that has been transformed or transfected with an expression vector containing a polynucleotide that encodes a recombinant polypeptide. Suitable host cells include prokaryotes, yeast and higher eukaryotic cells. Preferably, the host cells employed are *E. coli,* yeast or a mammalian cell line, such as CHO cells. The DNA sequences expressed in this manner may encode naturally occurring polypeptides, portions of naturally occurring polypeptides, or other variants thereof.

In general, regardless of the method of preparation, the polypeptides disclosed herein are prepared in an isolated, substantially pure, form (i.e., the polypeptides are homogenous as determined by amino acid composition and primary sequence analysis). Preferably, the polypeptides are at least about 90% pure, more preferably at least about 95% pure and most preferably at least about 99% pure. In certain preferred embodiments, described in more detail below, the substantially pure polypeptides are incorporated into pharmaceutical compositions or vaccines for use in one or more of the methods disclosed herein.

In a related aspect, the present invention provides fusion proteins comprising a first and a second inventive polypeptide or, alternatively, a polypeptide of the present invention and a known breast tumor antigen, together with variants of such fusion proteins.

A DNA sequence encoding a fusion protein of the present invention is constructed using known recombinant DNA techniques to assemble separate DNA sequences encoding the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39–46, 1985; Murphy et al., *Proc. Natl. Acad Sci. USA* 83:8258–8262, 1986; U.S. Pat. No. 4,935,233 and U.S. Pat. No. 4,751,180. The linker sequence may be from 1 to about 50 amino acids in length. Peptide sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons require to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J Med.,* 336:86–91 (1997)).

Polypeptides of the present invention that comprise an immunogenic portion of a breast tumor antigen may generally be used for immunotherapy of breast cancer, wherein the polypeptide stimulates the patient's own immune response to breast tumor cells. The present invention thus provides methods for using one or more of the immunoreactive polypeptides encoded by a polynucleotide comprising a sequence of SEQ ID NO: 1–61 and 63–174 (or fusion proteins comprising one or more such polypeptides and/or DNA encoding such polypeptides) for immunotherapy of breast cancer in a patient. As used herein, a "patient" refers to any warm—blooded animal, preferably a human. A patient may be afflicted with a disease, or may be free of detectable disease. Accordingly, the above immunoreactive polypeptides (or fusion proteins or polynucleotides encoding such polypeptides) may be used to treat breast cancer or to inhibit the development of breast cancer. The polypeptides may be administered either prior to or following surgical removal of primary tumors and/or treatment by administration of radiotherapy and conventional chemotherapeutic drugs.

In these aspects, the polypeptide or fusion protein is generally present within a pharmaceutical composition and/or a vaccine. Pharmaceutical compositions may comprise one or more polypeptides, each of which may contain one or more of the inventive sequences (or variants thereof), and a physiologically acceptable carrier. The vaccines may comprise one or more such polypeptides and a non-specific immune response enhancer, wherein the non-specific immune response enhancer is capable of eliciting or enhancing an immune response to an exogenous antigen. Examples of non-specific-immune response enhancers include adjuvants, biodegradable microspheres (e.g., polylactic galactide) and liposomes (into which the polypeptide is incorporated). Pharmaceutical compositions and vaccines may also contain other epitopes of breast tumor antigens, either incorporated into a combination polypeptide (i.e., a single polypeptide that contains multiple epitopes) or present within a separate polypeptide.

Alternatively, a pharmaceutical composition or vaccine may contain DNA encoding one or more of the above polypeptides, such that the polypeptide is generated in situ. In such pharmaceutical compositions and vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter). Bacterial delivery systems involve the administration of a bacterium (such as *Bacillus—Calmette—Guerrin*) that expresses an epitope of a breast tumor cell antigen on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., PNAS 86:317–321, 1989; Flexner et al., *Ann. N.Y. Acad Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., PNAS 91:215–219, 1994; Kass-Eisler et al., PNAS 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in published PCT application WO 90/11092, and Ulmer et al., *Science* 259:1745–1749, 1993, reviewed by Cohen, *Science* 259:1691–1692, 1993. The uptake of naked DNA may be increased by coating the DNA onto biodegradable beads, which are efficiently transported into the cells.

Routes and frequency of administration, as well as dosage, will vary from individual to individual and may parallel those currently being used in immunotherapy of other diseases. In general, the pharmaceutical compositions and vaccines may be administered by injection (e.g., intracutaneous, intramuscular, intravenous or subcutaneous), intranasally (e.g., by aspiration) or orally. Between 1 and 10 doses may be administered over a 3–24 week period. Preferably, 4 doses are administered, at an interval of 3 months, and booster administrations may be given periodically thereafter. Alternate protocols may be appropriate for individual patients. A suitable dose is an amount of polypeptide or DNA that is effective to raise an immune response (cellular and/or humoral) against breast tumor cells in a treated patient. A suitable immune response is at least 10–50% above the basal (i.e., untreated) level. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 $\mu$g. Suitable dose sizes will vary with the size of the patient, but will typically range from about 0.01 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a lipid, a wax and/or a buffer. For oral administration, any of the above carriers or a solid carrier, such as mannitol, lactose, starch, magnesium stearate, sodium saccharine, talcum, cellulose, glucose, sucrose, and/or magnesium carbonate, may be employed. Biodegradable microspheres (e.g., polylactic glycolide) may also be employed as carriers for the pharmaceutical compositions of this invention. Suitable biodegradable microspheres are disclosed, for example, in U.S. Pat. Nos. 4,897,268 and 5,075,109.

Any of a variety of non-specific immune response enhancers may be employed in the vaccines of this invention. For example, an adjuvant may be included.

Most adjuvants contain a substance designed to protect the antigen from rapid catabolism, such as aluminum hydroxide or mineral oil, and a nonspecific stimulator of immune response, such as lipid A, *Bordella pertussis* or *Mycobacterium tuberculosis.* Such adjuvants are commercially available as, for example, Freund's Incomplete Adjuvant and Complete Adjuvant (Difco Laboratories, Detroit, Mich.) and Merck Adjuvant 65 (Merck and Company, Inc., Rahway, N.J.).

Polypeptides disclosed herein may also be employed in adoptive immunotherapy for the treatment of cancer. Adoptive immunotherapy may be broadly classified into either active or passive immunotherapy. In active immunotherapy, treatment relies on the in vivo stimulation of the endogenous host immune system to react against tumors with the administration of immune response-modifying agents (for example, tumor vaccines, bacterial adjuvants, and/or cytokines).

In passive immunotherapy, treatment involves the delivery of biologic reagents with established tumor-immune reactivity (such as effector cells or antibodies) that can directly or indirectly mediate antitumor effects and does not necessarily depend on an intact host immune system. Examples of effector cells include T lymphocytes (for example, CD8+ cytotoxic T-lymphocyte, CD4+ T-helper, tumor-infiltrating lymphocytes), killer cells (Natural Killer cells, lymphokine-activated killer cells), B cells, or antigen presenting cells (such as dendritic cells and macrophages) expressing the disclosed antigens. The polypeptides disclosed herein may also be used to generate antibodies or anti-idiotypic antibodies (as in U.S. Pat. No. 4,918,164), for passive immunotherapy.

The predominant method of procuring adequate numbers of T-cells for adoptive immunotherapy is to grow immune T-cells in vitro. Culture conditions for expanding single antigen-specific T-cells to several billion in number with retention of antigen recognition in vivo are well known in the art. These in vitro culture conditions typically utilize intermittent stimulation with antigen, often in the presence of cytokines, such as IL-2, and non-dividing feeder cells. As noted above, the immunoreactive polypeptides described herein may be used to rapidly expand antigen-specific T cell cultures in order to generate sufficient number of cells for immunotherapy. In particular, antigen-presenting cells, such as dendritic, macrophage or B-cells, may be pulsed with immunoreactive polypeptides or transfected with a polynucleotide sequence(s), using standard techniques well known in the art. For cultured T-cells to be effective in therapy, the cultured T-cells must be able to grow and distribute widely and to survive long term in vivo. Studies have demonstrated that cultured T-cells can be induced to grow in vivo and to survive long term in substantial numbers by repeated stimulation with antigen supplemented with IL-2 (see, for example, Cheever et al. Ibid).

The polypeptides disclosed herein may also be employed to generate and/or isolate tumor—reactive T-cells, which can then be administered to the patient. In one technique, antigen-specific T-cell lines may be generated by in vivo immunization with short peptides corresponding to immunogenic portions of the disclosed polypeptides. The resulting antigen specific CD8+ CTL clones may be isolated from the patient, expanded using standard tissue culture techniques, and returned to the patient.

Alternatively, peptides corresponding to immunogenic portions of the polypeptides may be employed to generate tumor reactive T cell subsets by selective in vitro stimulation and expansion of autologous T cells to provide antigen-specific T cells which may be subsequently transferred to the patient as described, for example, by Chang et al. (*Crit. Rev. Oncol. Hematol.,* 22(3), 213, 1996).

In another embodiment, syngeneic or autologous dendritic cells may be pulsed with peptides corresponding to at least an immunogenic portion of a polypeptide disclosed herein. The resulting antigen-specific dendritic cells may either be transferred into a patient, or employed to stimulate T cells to provide antigen-specific T cells which may, in turn, be administered to a patient. The use of peptide-pulsed dendritic cells to generate antigen-specific T cells and the subsequent use of such antigen-specific T cells to eradicate tumors in a murine model has been demonstrated by Cheever et al. ("Therapy With Cultured T Cells: Principles Revisited," *Immunological Reviews,* 157:177, 1997). Additionally vectors expressing the disclosed polynucleotides may be introduced into stem cells taken from the patient and clonally propagated in vitro for autologous transplant back into the same patient.

In one specific embodiment, cells of the immune system, such as T cells, may be isolated from the peripheral blood of a patient, using a commercially available cell separation system, such as CellPro Incorporated's (Bothell, Wash.) CEPRATE[198] system (see U.S. Pat. No. 5,240,856; U.S. Pat. No. 5,215,926; WO 89/06280; WO 91/16116 and WO 92/07243). The separated cells are stimulated with one or more of the immunoreactive polypeptides contained within a delivery vehicle, such as a microsphere, to provide antigen-specific T cells. The population of tumor antigen-specific T cells is then expanded using standard techniques and the cells are administered back to the patient.

Additionally vectors expressing the disclosed polynucleotides may be introduced into stem cells taken from the patient and clonally propagated in vitro for autologous transplant back into the same patient.

Polypeptides of the present invention may also, or alternatively, be used to generate binding agents, such as antibodies or fragments thereof, that are capable of detecting metastatic human breast tumors. Binding agents of the present invention may generally be prepared using methods known to those of ordinary skill in the art, including the representative procedures described herein. Binding agents are capable of differentiating between patients with and without breast cancer, using the representative assays described herein. In other words, antibodies or other binding agents raised against a breast tumor antigen, or a suitable portion thereof, will generate a signal indicating the presence of primary or metastatic breast cancer in at least about 20% of patients afflicted with the disease, and will generate a negative signal indicating the absence of the disease in at least about 90% of individuals without primary or metastatic breast cancer. Suitable portions of such breast tumor antigens are portions that are able to generate a binding agent that indicates the presence of primary or metastatic breast cancer in substantially all (i.e., at least about 80%, and preferably at least about 90%) of the patients for which breast cancer would be indicated using the full length antigen, and that indicate the absence of breast cancer in substantially all of those samples that would be negative when tested with full length antigen. The representative assays described below, such as the two-antibody sandwich assay, may generally be employed for evaluating the ability of a binding agent to detect metastatic human breast tumors.

The ability of a polypeptide prepared as described herein to generate antibodies capable of detecting primary or metastatic human breast tumors may generally be evaluated by raising one or more antibodies against the polypeptide (using, for example, a representative method described herein) and determining the ability of such antibodies to detect such tumors in patients. This determination may be made by assaying biological samples from patients with and without primary or metastatic breast cancer for the presence of a polypeptide that binds to the generated antibodies. Such test assays may be performed, for example, using a representative procedure described below. Polypeptides that generate antibodies capable of detecting at least 20% of primary or metastatic breast tumors by such procedures are considered to be useful in assays for detecting primary or metastatic human breast tumors. Polypeptide specific antibodies may be used alone or in combination to improve sensitivity.

Polypeptides capable of detecting primary or metastatic human breast tumors may be used as markers for diagnosing breast cancer or for monitoring disease progression in patients. In one embodiment, breast cancer in a patient may be diagnosed by evaluating a biological sample obtained from the patient for the level of one or more of the above polypeptides, relative to a predetermined cut-off value. As used herein, suitable "biological samples" include blood, sera and urine.

The level of one or more of the above polypeptides may be evaluated using any binding agent specific for the polypeptide(s). A "binding agent," in the context of this invention, is any agent (such as a compound or a cell) that binds to a polypeptide as described above. As used herein, "binding" refers to a noncovalent association between two separate molecules (each of which may be free (i.e., in solution) or present on the surface of a cell or a solid support), such that a "complex" is formed. Such a complex may be free or immobilized (either covalently or noncovalently) on a support material. The ability to bind may generally be evaluated by determining a binding constant for the formation of the complex. The binding constant is the value obtained when the concentration of the complex is divided by the product of the component concentrations. In general, two compounds are said to "bind" in the context of the present invention when the binding constant for complex formation exceeds about $10^3$ L/mol. The binding constant may be determined using methods well known to those of ordinary skill in the art.

Any agent that satisfies the above requirements may be a binding agent. For example, a binding agent may be a ribosome with or without a peptide component, an RNA molecule or a peptide. In a preferred embodiment, the binding partner is an antibody, or a fragment thereof Such antibodies may be polyclonal, or monoclonal. In addition, the antibodies may be single chain, chimeric, CDR-grafted or humanized. Antibodies may be prepared by the methods described herein and by other methods well known to those of skill in the art.

There are a variety of assay formats known to those of ordinary skill in the art for using a binding partner to detect polypeptide markers in a sample. See, e.g., Harlow and Lane, *Antibodies: A Laboratory Manual,* Cold Spring Harbor Laboratory, 1988. In a preferred embodiment, the assay involves the use of binding partner immobilized on a solid support to bind to and remove the polypeptide from the remainder of the sample. The bound polypeptide may then be detected using a second binding partner that contains a reporter group. Suitable second binding partners include antibodies that bind to the binding partner/polypeptide complex. Alternatively, a competitive assay may be utilized, in which a polypeptide is labeled with a reporter group and allowed to bind to the immobilized binding partner after incubation of the binding partner with the sample. The extent to which components of the sample inhibit the binding of the labeled polypeptide to the binding partner is indicative of the reactivity of the sample with the immobilized binding partner.

The solid support may be any material known to those of ordinary skill in the art to which the antigen may be attached. For example, the solid support may be a test well in a microtiter plate or a nitrocellulose or other suitable membrane.

Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 $\mu$g, and preferably about 100 ng to about 1 $\mu$g, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a second antibody (containing a reporter group) capable of binding to a different site on the polypeptide is added. The amount of second antibody that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is that period of time that is sufficient to detect the presence of polypeptide within a sample obtained from an individual with breast cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include enzymes (such as horseradish peroxidase), substrates, cofactors, inhibitors, dyes, radionuclides, luminescent groups, fluorescent groups and biotin. The conjugation of antibody to reporter group may be achieved using standard methods known to those of ordinary skill in the art.

The second antibody is then incubated with the immobilized antibody-polypeptide complex for an amount of time sufficient to detect the bound polypeptide. An appropriate amount of time may generally be determined by assaying the level of binding that occurs over a period of time. Unbound second antibody is then removed and bound second antibody is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of breast cancer, the signal detected from the reporter group that remains bound to the solid support is generally compared to a signal that corresponds to a predetermined cut-off value. In one preferred embodiment, the cut-off value is the average mean signal obtained when the immobilized antibody is incubated with samples from patients without breast cancer. In general, a sample generating a signal that is three standard deviations above the predetermined cut-off value is considered positive for breast cancer. In an alternate preferred embodiment, the cut-off value is determined using a Receiver Operator Curve, according to the method of Sackett et al., *Clinical Epidemiology: A Basic Science for Clinical Medicine,* Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for breast cancer.

In a related embodiment, the assay is performed in a flow-through or strip test format, wherein the antibody is immobilized on a membrane, such as nitrocellulose. In the flow—through test, polypeptides within the sample bind to the immobilized antibody as the sample passes through the membrane. A second, labeled antibody then binds to the antibody-polypeptide complex as a solution containing the second antibody flows through the membrane. The detection of bound second antibody may then be performed as described above. In the strip test format, one end of the membrane to which antibody is bound is immersed in a solution containing the sample. The sample migrates along the membrane through a region containing second antibody and to the area of immobilized antibody. Concentration of second antibody at the area of immobilized antibody indicates the presence of breast cancer. Typically, the concentration of second antibody at that site generates a pattern, such as a line, that can be read visually. The absence of such a pattern indicates a negative result. In general, the amount of antibody immobilized on the membrane is selected to generate a visually discernible pattern when the biological sample contains a level of polypeptide that would be sufficient to generate a positive signal in the two-antibody sandwich assay, in the format discussed above. Preferably, the amount of antibody immobilized on the membrane ranges from about 25 ng to about 1 $\mu$g, and more preferably from about 50 ng to about 500 ng. Such tests can typically be performed with a very small amount of biological sample.

Of course, numerous other assay protocols exist that are suitable for use with the antigens or antibodies of the present invention. The above descriptions are intended to be exemplary only.

In another embodiment, the above polypeptides may be used as markers for the progression of breast cancer. In this embodiment, assays as described above for the diagnosis of breast cancer may be performed over time, and the change in the level of reactive polypeptide(s) evaluated. For example, the assays may be performed every 24–72 hours for a period of 6 months to 1 year, and thereafter performed as needed. In general, breast cancer is progressing in those patients in whom the level of polypeptide detected by the binding agent increases over time. In contrast, breast cancer is not progressing when the level of reactive polypeptide either remains constant or decreases with time.

Antibodies for use in the above methods may be prepared by any of a variety of techniques known to those of ordinary skill in the art. See, e.g., Harlow and Lane, *Antibodies: A Laboratory Manual,* Cold Spring Harbor Laboratory, 1988. In one such technique, an immunogen comprising the antigenic polypeptide is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Monoclonal antibodies of the present invention may also be used as therapeutic reagents, to diminish or eliminate breast tumors. The antibodies may be used on their own (for instance, to inhibit metastases) or coupled to one or more therapeutic agents. Suitable agents in this regard include radionuclides, differentiation inducers, drugs, toxins, and derivatives thereof Preferred radionuclides include 90Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl—containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement—mediated hydrolysis (e.g., U.S. Pat. No. 4,671,958, to Rodwell et al.), and acid—catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U. S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Diagnostic reagents of the present invention may also comprise DNA sequences encoding one or more of the above polypeptides, or one or more portions thereof. For example, at least two oligonucleotide primers may be employed in a polymerase chain reaction (PCR) based assay to amplify breast tumor—specific cDNA derived from a biological sample, wherein at least one of the oligonucleotide primers is specific for a polynucleotide encoding a breast tumor protein of the present invention. The presence of the amplified cDNA is then detected using techniques well known in the art, such as gel electrophoresis. Similarly, oligonucleotide probes specific for a polynucleotide encoding a breast tumor protein of the present invention may be used in a hybridization assay to detect the presence of an inventive polypeptide in a biological sample.

As used herein, the term “oligonucleotide primer/probe specific for a polynucleotide” means an oligonucleotide sequence that has at least about 60%, preferably at least about 75% and more preferably at least about 90%, identity to the polynucleotide in question. Oligonucleotide primers and/or probes which may be usefully employed in the inventive diagnostic methods preferably have at least about 10–40 nucleotides. In a preferred embodiment, the oligonucleotide primers comprise at least about 10 contiguous nucleotides of a polynucleotide comprising a sequence selected from SEQ ID NO: 1–61 and 63–174. Preferably, oligonucleotide probes for use in the inventive diagnostic methods comprise at least about 15 contiguous oligonucleotides of a polynucleotide comprising a sequence provided in SEQ ID NO: 1–61 and 63–174. Techniques for both PCR based assays and hybridization assays are well known in the art (see, for example, *Mullis et al. Ibid; Ehrlich, Ibid*). Primers or probes may thus be used to detect breast tumor-specific sequences in biological samples, including blood, urine and/or breast tumor tissue.

The following Examples are offered by way of illustration and not by way of limitation.

EXAMPLES

Example 1

ISOLATION AND CHARACTERIZATION OF BREAST TUMOR POLYPEPTIDES

This Example describes the isolation of breast tumor polypeptides from a breast tumor cDNA library.

A cDNA subtraction library containing cDNA from breast tumor subtracted with normal breast cDNA was constructed as follows. Total RNA was extracted from primary tissues using Trizol reagent (Gibco BRL Life Technologies, Gaithersburg, Md.) as described by the manufacturer. The polyA+ RNA was purified using an oligo(dT) cellulose column according to standard protocols. First strand cDNA was synthesized using the primer supplied in a Clontech PCR-Select cDNA Subtraction Kit (Clontech, Palo Alto, Calif.). The driver DNA consisted of cDNAs from two normal breast tissues with the tester cDNA being from three primary breast tumors. Double-stranded cDNA was synthesized for both tester and driver, and digested with a combination of endonucleases (luI, MscI, PvuII, SalI and StuI) which recognize six base pairs DNA. This modification increased the average cDNA size dramatically compared with cDNAs generated according to Clontech's protocol. The digested tester cDNAs were ligated to two different adaptors and the subtraction was performed according to Clontech's protocol. The subtracted cDNAs were subjected to two rounds of PCR amplification, following the manufacturer's protocol. The resulting PCR products were subcloned into the TA cloning vector, pCRII (Invitrogen, San Diego, Calif.) and transformed into ElectroMax *E. coli* DH10B cells (Gibco BRL Life, Technologies) by electroporation. DNA was isolated from independent clones and sequenced using a Perkin Elmer/Applied Biosystems Division (Foster City, Calif.) Automated Sequencer Model 373A.

Sixty-three distinct cDNA clones were found in the subtracted breast tumor—specific cDNA library. The determined one strand (5' or 3') cDNA sequences for the clones are provided in SEQ ID NO: 1–61, 72 and 73, respectively. Comparison of these cDNA sequences with known sequences in the gene bank using the EMBL and GenBank databases (Release 97) revealed no significant homologies to the sequences provided in SEQ ID NO: 14, 21, 22, 27, 29, 30, 32, 38, 44, 45, 53, 72 and 73. The sequences of SEQ ID NO: 1, 3, 16, 17, 34, 48, 57, 60 and 61 were found to represent known human genes. The sequences of SEQ ID NO: 2, 4, 23, 39 and 50 were found to show some similarity to previously identified non-human genes. The remaining clones (SEQ ID NO: 5–13, 15, 18–20, 24–26, 28, 31, 33, 35–37, 40–43, 46, 47, 49, 51, 52, 54–56, 58 and 59) were found to show at least some degree of homology to previously identified expressed sequence tags (ESTs).

To determine mRNA expression levels of the isolated cDNA clones, cDNA clones from the breast subtraction described above were randomly picked and colony PCR amplified. Their mRNA expression levels in breast tumor, normal breast and various other normal tissues were determined using microarray technology (Synteni, Palo Alto, Calif.). Briefly, the PCR amplification products were arrayed onto slides in an array format, with each product occupying a unique location in the array. mRNA was extracted from the tissue sample to be tested, reverse transcribed, and fluorescent—labeled cDNA probes were generated. The microarrays were probed with the labeled cDNA probes, the slides scanned and fluorescence intensity was measured.

Data was analyzed using Synteni provided GEMTOOLS Software. Of the seventeen cDNA clones examined, those of SEQ ID NO: 40, 46, 59 and 73 were found to be over-expressed in breast tumor and expressed at low levels in all normal tissues tested (breast, PBMC, colon, fetal tissue, salivary gland, bone marrow, lung, pancreas, large intestine, spinal cord, adrenal gland, kidney, pancreas, liver, stomach, skeletal muscle, heart, small intestine, skin, brain and human mammary epithelial cells). The clones of SEQ ID NO: 41 and 48 were found to be over-expressed in breast tumor and expressed at low levels in all other tissues tested, with the exception of bone marrow. The clone of SEQ ID NO: 42 was found to be over-expressed in breast tumor and expressed at low levels in all other tissues tested except bone marrow and spinal cord. The clone of SEQ ID NO: 43 was found to be over-expressed in breast tumor and expressed at low levels in all other tissues tested with the exception of spinal cord, heart and small intestine. The clone of SEQ ID NO: 51 was found to be over-expressed in breast tumor and expressed at low levels in all other tissues tested with the exception of large intestine. The clone of SEQ ID NO: 54 was found to be over-expressed in breast tumor and expressed at low levels in all other tissues tested with the exception of PBMC, stomach and small intestine. The clone of SEQ ID NO: 56 was found to be over-expressed in breast tumor and expressed at low levels in all other tissues tested with the exception of large and small intestine, human mammary epithelia cells and SCID mouse—passaged breast tumor. The clone of SEQ ID NO: 60 was found to be over-expressed in breast tumor and expressed at low levels in all other tissues tested with the exception of spinal cord and heart. The clone of SEQ ID NO: 61 was found to be over-expressed in breast tumor and expressed at low levels in all other tissues tested with the exception of small intestine. The clone of SEQ ID NO: 72 was found to be over-expressed in breast tumor and expressed at low levels in all other tissues tested with the exception of colon and salivary gland.

The results of a Northern blot analysis of the clone SYN18C6 (SEQ ID NO: 40) are shown in FIG. 1. A predicted protein sequence encoded by SYN18C6 is provided in SEQ ID NO: 62

Additional cDNA clones that are over-expressed in breast tumor tissue were isolated from breast cDNA subtraction libraries as follows. Breast subtraction libraries were prepared, as described above, by PCR—based subtraction employing pools of breast tumor cDNA as the tester and pools of either normal breast cDNA or cDNA from other normal tissues as the driver. cDNA clones from breast subtraction were randomly picked and colony PCR amplified and their mRNA expression levels in breast tumor, normal breast and various other normal tissues were determined using the microarray technology described above. Twenty-four distinct cDNA clones were found to be over-expressed in breast tumor and expressed at low levels in all normal tissues tested (breast, brain, liver, pancreas, lung, salivary gland, stomach, colon, kidney, bone marrow, skeletal muscle, PBMC, heart, small intestine, adrenal gland, spinal cord, large intestine and skin). The determined partial cDNA sequences for these clones are provided in SEQ ID NO: 63–87. Comparison of the sequences of SEQ ID NO: 74–87 with those in the gene bank as described above, revealed homology to previously identified human genes. No significant homologies were found to the sequences of SEQ ID NO: 63–73.

Example 2

ISOLATION AND CHARACTERIZATION OF BREAST TUMOR POLYPEPTIDES OBTAINED BY PCR-BASED SUBTRACTION USING SCID-PASSAGED TUMOR RNA

Human breast tumor antigens were obtained by PCR-based subtraction using SCID mouse passaged breast tumor RNA as follows. Human breast tumor was implanted in SCID mice and harvested on the first or sixth serial passage, as described in patent application Ser. No. 08/556,659 filed Nov. 13, 1995, U.S. Pat. No. 5,986,170. Genes found to be differentially expressed between early and late passage SCID tumor may be stage specific and therefore useful in therapeutic and diagnostic applications. Total RNA was prepared from snap frozen SCID passaged human breast tumor from both the first and sixth passage.

PCR—based subtraction was performed essentially as described above. In the first subtraction (referred to as T9), RNA from first passage tumor was subtracted from sixth passage tumor RNA to identify more aggressive, later passage-specific antigens. Of the 64 clones isolated and sequenced from this subtraction, no significant homologies were found to 30 of these clones, hereinafter referred to as: 13053, 13057, 13059, 13065, 13067, 13068, 13071–13073, 13075, 13078, 13079, 13081, 13082, 13092, 13097, 13101, 13102, 13131, 13133, 13119, 13135, 13139, 13140, 13146–13149, and 13151, with the exception of some previously identified expressed sequence tags (ESTs). The determined cDNA sequences for these clones are provided in SEQ ID NO: 88–116, respectively. The isolated cDNA sequences of SEQ ID NO: 117–140 showed homology to known genes.

In a second PCR—based subtraction, RNA from sixth passage tumor was subtracted from first passage tumor RNA to identify antigens down—regulated over multiple passages. Of the 36 clones isolated and sequenced, no significant homologies were found to nineteen of these clones, hereinafter referred to as: 14376, 14377, 14383, 14384, 14387, 14392, 14394, 14398, 14401, 14402, 14405, 14409, 14412, 14414–14416, 14419, 14426, and 14427, with the exception of some previously identified expressed sequence tags (ESTs). The determined cDNA sequences for these clones are provided in SEQ ID NO: 141–159, respectively. The isolated cDNA sequences of SEQ ID NO: 160–174 were found to show homology to previously known genes.

Example 3

SYNTHESIS OF POLYPEPTIDES

Polypeptides may be synthesized on an Perkin Elmer/Applied Biosystems Division 430A peptide synthesizer using FMOC chemistry with UPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

From the foregoing, it will be appreciated that, although specific embodiments of the invention have been described herein for the purposes of illustration, various modifications may be made without deviating from the spirit and scope of the invention.

What is claimed is:

1. An isolated polynucleotide consisting of SEQ ID NO: 56.

2. An isolated polynucleotide consisting of SEQ ID NO: 57.

3. An isolated polynucleotide consisting of SEQ ID NO: 63.

4. An isolated polynucleotide consisting of SEQ ID NO: 71.

5. An isolated cDNA comprising a sequence selected from the group consisting of: sequences having at least 90% identity to SEQ ID NO: 56.

6. An isolated cDNA comprising a sequence selected from the group consisting of: sequences having at least 90% identity to SEQ ID NO: 71.

7. An isolated cDNA comprising a sequence selected from the group consisting of sequences having at least 90% identity to SEQ ID NO: 63.

8. An expression vector comprising a polynucleotide according to any one of claims 5 and 6.

9. A host cell transformed with the expression vector of claim 8.

10. The host cell of claim 9 wherein the host cell is selected from the group consisting of *E. coli*, yeast and mammalian cell lines.

11. A diagnostic kit comprising two oligonucleotide primers, at least one of the oligonucleotide primers being specific for a polynucleotide of any one of claims 1–5 and 6 and being at least 10 nucleotides in length.

12. A diagnostic kit comprising two oligonucleotide probes, at least one of the oligonucleotide probes being specific for a polynucleotide of any one of claims 1–5 and 6 being at least 10 nucleotide in length.

* * * * *

UNITED STATES PATENT AND TRADEMARK OFFICE

CERTIFICATE OF CORRECTION

PATENT NO. : 6,387,697 B1
DATED : May 14, 2002
INVENTOR(S) : Jiang Yuqiu et al.

It is certified that error appears in the above-identified patent and that said Letters Patent is hereby corrected as shown below:

Column 160,
Line 2, "according to any one of claims 5 and 6." should read -- according to any one of claims 1-6. --.

Signed and Sealed this

Twenty-fourth Day of December, 2002

JAMES E. ROGAN
*Director of the United States Patent and Trademark Office*

SEQUENCE LISTING

```
<160> NUMBER OF SEQ ID NOS: 174

<210> SEQ ID NO 1
<211> LENGTH: 281
<212> TYPE: DNA
<213> ORGANISM: Human

<400> SEQUENCE: 1

caatgacagt caatctctat cgacagcctg cttcatattt agctattgtt c gtattgcct     60

tctgtcctag gaacagtcat atctcaagtt caaatgccac aacctgagaa g cggtgggct    120

aagataggtc ctactgcaaa ccacccctcc atatttccgt acgcaattac a attcagttt    180

ctgtgacatc tctttacacc actggaggaa aaatgagata ttctctgatt t attctacta    240

taacactcta catagagcta tggtgagtgc taaccacatc g                         281


<210> SEQ ID NO 2
<211> LENGTH: 300
<212> TYPE: DNA
<213> ORGANISM: Human

<400> SEQUENCE: 2

gaggtcctgg gctaacctaa tggtttatta ttggtggaga gaaagatctg g aaatacttg     60
```

```
aggttattac atactagatt agcttctaat gtgaaccatt tttcttttaa c agtgataaa    120

ttattatttc cgaagttaac tgttcccttg gtcgtgatac acactcgatt a acaaacata    180

ctgttgtatt ttttccagtt ttgtttggct atgccaccac agtcatcccc a gggtctata    240

catactatgt ctcaactgta ttatttgcca tttttggcat tagaatgctt c gggaaggct    300


<210> SEQ ID NO 3
<211> LENGTH: 302
<212> TYPE: DNA
<213> ORGANISM: Human

<400> SEQUENCE: 3

ggccgaggta attggttaag tctaaagaga ttattattcc ttgatgtttg c tttgtattg     60

gctacaaatg tgcagaggta atacatatgt gatgtcgatg tctctgtctt t ttttttgtc    120

tttaaaaaat aattggcagc aactgtattt gaataaaatg atttcttagt a tgattgtac    180

agtaatgaat gaaagtggaa catgtttctt tttgaaaggg agagaattga c catttattg    240

ttgtgatgtt taagttataa cttatcgagc acttttagta gtgataactg t ttttaaact    300

tg                                                                   302


<210> SEQ ID NO 4
<211> LENGTH: 293
<212> TYPE: DNA
<213> ORGANISM: Human

<400> SEQUENCE: 4

tgtaccaatc ctttggcaca agaatatgta agaactatag ttgtttttat t ggtttttgt     60

tcttgagatt gttttcattc tgtttttgac tgtatctctt taggaggctg a ggatggcat    120

tattgcttat gatgactgtg gggtgaaact gactattgct tttcaagcca a ggatgtgga    180

aggatctact tctcctcaaa tacgagataa ggcaagataa ttctgctcat t cgagagagg    240

gttaagagtt gtcatcttaa tcataaatcc tgcaggatgg gttcttcaaa t tt          293


<210> SEQ ID NO 5
<211> LENGTH: 275
<212> TYPE: DNA
<213> ORGANISM: Human

<400> SEQUENCE: 5

cgaggtttgg aatcagactt ctgtgtccag taaaaaactc ctgcactgaa g tcattgtga     60

cttgagtagt tacagactga ttccagtgaa cttgatctaa tttcttttga t ctaatgaat    120

gtgtctgctt accttgtctc cttttaattg ataagctcca agtagttgct a attttttga    180

caactttaaa tgagtttcat tcacttcttt tacttaatgt tttaagtata g taccaataa    240

tttcattaac ctgttctcaa gtggtttagc tacca                               275


<210> SEQ ID NO 6
<211> LENGTH: 301
<212> TYPE: DNA
<213> ORGANISM: Human

<400> SEQUENCE: 6

gaggtctggt ttcctgggta tgcctggact gttgcccagt gtaagatctg t gcaagccat     60

attggatgga agtttacggc caccaaaaaa gacatgtcac ctcaaaaatt t tggggctta    120

acgcgatctg ctctgttgcc cacgatccca gacactgaag atgaaataag t ccagacaaa    180
```

-continued

```
gtaatacttt gcttgtaaac agatgtgata gagataaagt tatctaacaa a ttggttata    240

ttctaagatc tgctttggaa attattgcct ctgatacata cctaagtaaa c ataacatta    300

a                                                                     301


<210> SEQ ID NO 7
<211> LENGTH: 301
<212> TYPE: DNA
<213> ORGANISM: Human

<400> SEQUENCE: 7

gtccagtttg tacacagtga ttccttatgc acgccgaaag ggtttccgta a aaatgacat     60

tatatacaaa tctgtacacc catccaccag agcgattctc cagctcccag a gggagttat    120

caacttaaag caggatacct gaggtttcat gtctttagtt gccttatcat a atcccaaat    180

atacatttca gggtttgttt ttgtttttaa agacactttc ctggaatatg t gcactatgg    240

ttaaaattaa aaacaaaagt aataaaataa aatgatcgct ggaaggactg a cctccccac    300

c                                                                     301


<210> SEQ ID NO 8
<211> LENGTH: 301
<212> TYPE: DNA
<213> ORGANISM: Human

<400> SEQUENCE: 8

ctgtcctcat ctctgcaaag ttcagcttcc ttccccaggt ctctgtgcac t ctgtcttgg     60

atgctctggg gagctcatgg gtggaggagt ctccaccaga gggaggctca g gggactggt    120

tgggccaggg atgaatattt gagggataaa aattgtgtaa gagccaaaga a ttggtagta    180

gggggagaac agagaggagc tgggctatgg gaaatgattt gaataatgga g ctgggaata    240

tggctggata tctggtacta aaaaagggtc tttaagaacc tacttcctaa t ctcttcccc    300

a                                                                     301


<210> SEQ ID NO 9
<211> LENGTH: 301
<212> TYPE: DNA
<213> ORGANISM: Human

<400> SEQUENCE: 9

gaggtctgcc taagtagagg acaaagactt cctcctttca aaggagaact g agcccagga     60

ttggtaagtt taaggcactt aaccttgacc agctctgtag gtctggagca t tctggtccc    120

tggccgcttt caccaccagg cccttctcac ttatccacct cacatactgc c ccagcattc    180

ctttggcatt gcgagctgtg acttgacaca ttttaatgac aagattgaag t agctacctt    240

gcaggataga ttttctgggg tataggggac aaaccaacag tgccatcagg t gtcttaaca    300

c                                                                     301


<210> SEQ ID NO 10
<211> LENGTH: 301
<212> TYPE: DNA
<213> ORGANISM: Human

<400> SEQUENCE: 10

ggcaggtcca acagttcttc cagttctggt cgagctttga atcgtccctt g aagtcttct     60

tcagtgtgct ccttcactga cagtctgact ccttcaggaa gactgctttg g attatttcc    120

aagaaaattt ctgcaaacgt agcactcaaa ccgctgatct gaaccactcg c tcatgggtg    180
```

-continued

```
gtaagcactg agtccaggag cattttgctg ccttggtcct gcaactgcaa c acttctatg    240

gttttggttg gcattgcata actttcctcg actttaatgg agagagattg c agaggttgt    300

g                                                                     301


<210> SEQ ID NO 11
<211> LENGTH: 301
<212> TYPE: DNA
<213> ORGANISM: Human

<400> SEQUENCE: 11

aggtctgtga ctttcaccca ggacccagga cgcagccctc cgtgggcact g ccggcgcct     60

tgtctgcaca ctggaggtcc tccattacag aggcccagcg cacatcgctg g ccccacaaa    120

cgttcagggg tacagccatg gcagctcctt cctctgccgt gagaaaagtg c ttggagtac    180

ggtttgccac acacgtgact ggacagtgtc caattcaaat ctttcagggc a gagtccgag    240

cagcgcttgg tgacagcctg tcctctcctg ctctccaaag gccctgctcc c tgtcctctc    300

t                                                                     301


<210> SEQ ID NO 12
<211> LENGTH: 301
<212> TYPE: DNA
<213> ORGANISM: Human

<400> SEQUENCE: 12

gaggtctggg attacaggca cgtgccacca cacctagcta atttttgagc a tggggctca     60

aaggaactgc tctctggggc atgtcagatt tcggatttgg ggctgcacac t gatactctc    120

taagtggtgg aggaacttca tcccactgaa attcctttgg catttggggt t ttgtttttc    180

tttttttcct tcttcatcct cctccttttt taaaagtcaa cgagagcctt c gctgactcc    240

accgaagaag tgcaccactg ggagccaccc cagtgccagg cgcccgtcca g ggacacaca    300

c                                                                     301


<210> SEQ ID NO 13
<211> LENGTH: 256
<212> TYPE: DNA
<213> ORGANISM: Human

<400> SEQUENCE: 13

tttttggca taaaaaacac aatgatttaa tttctaaagc acttatatta t tatggcatg     60

gtttgggaaa caggttatta tattccacat aggtaattat gcagtgcttc t catggaaaa    120

aatgcttagg tattggcctt ttctctggaa accatatttt tcctttttta a taatcaact    180

aaaatgtata tgttaaaaag cctcatcttt tgattttcaa tatacaaaat g ctttcttta    240

aaagaacaag attcaa                                                     256


<210> SEQ ID NO 14
<211> LENGTH: 301
<212> TYPE: DNA
<213> ORGANISM: Human

<400> SEQUENCE: 14

ggtccttgat agaggaagag gaatatccaa ggcaaagcca ccaccacgtc c aacctcctc     60

atcctctacc tttcctgtcc ccagaggtat gagatagacc ccctggcctg g ttcctgcac    120

tgtgctaggc ccacagtgga cacttccacc ttaatggaga ataggcccca t ggagtggag    180
```

-continued

```
gtccctcctc catggcctgc aacccaatga ctatgggggt gacacaagtg a cctctgccc    240

tgtgatggct caacaccatc acacgcaact gtccagacaa gccccctcaa c gggctgctg    300

t                                                                    301


<210> SEQ ID NO 15
<211> LENGTH: 259
<212> TYPE: DNA
<213> ORGANISM: Human

<400> SEQUENCE: 15

gtcttgaaag tatttattgt ttaataattc tttctcccct cagccccatc c ggccactct     60

ctctttctgc ttttctgatc atcctaaagg ctgaatacat cctcctcctg t gtggaggac    120

acgaagcaat actaaaatca atacactcga tcaggtcttc atcagatacc a cgtcactgt    180

gggtagagtg ctaattttca acaaatgtgg tgttcttagg gccccacaag g tagtccttt    240

ctcaaggtcg ctgggccac                                                 259


<210> SEQ ID NO 16
<211> LENGTH: 301
<212> TYPE: DNA
<213> ORGANISM: Human

<400> SEQUENCE: 16

cgaggttgtt cacattttca aataaataat actccccgta agtaataact g caaccaatc     60

agtgttattc agtgctatgc ctccttgtaa tgggtagtta ttaattattt t cagagcttt    120

ctggaaatac tgtcctaact ggctatgttt aggatctttg ttatctctga a gacaaagaa    180

agaactagga ctcttaattt tggggtgctt cttgactctt agttgggaaa c tgaaaatat    240

ttccaacctt ttacccacgt caatggcata ttctgggaat caccaccacc a ccaccacta    300

c                                                                    301


<210> SEQ ID NO 17
<211> LENGTH: 301
<212> TYPE: DNA
<213> ORGANISM: Human

<400> SEQUENCE: 17

gcccgggcag gtctggggcc tagggtggct ctttgcaaag ctgaggggca a gctaaggaa     60

gccaggcagg tcaggggccc tttcggcctt ctcaagcctc cacctgagtt c tcgtcaatg    120

ccagtctccc tggtatgatt ggggacatta tcagagaaac atctaatagc g cacatctgg    180

gcacccacac tctgcttcag ttgcatccat cctcccaccc caaattcaac t cctgaccca    240

atacaaaaga ctttttttaac caggatttct tcttgcagga aagctgactt g gaaacacgg    300

g                                                                    301


<210> SEQ ID NO 18
<211> LENGTH: 301
<212> TYPE: DNA
<213> ORGANISM: Human

<400> SEQUENCE: 18

attacaggca cgtgccacca cacctagcta atttttgagc atggggctca a aggaactgc     60

tctctggggc atgtcagatt tcggatttgg ggctgcacac tgatactctc t aagtggtgg    120

aggaacttca tcccactgaa attcctttgg catttggggt tttgtttttc t ttttttcct    180

tcttcatcct cctccttttt taaaagtcaa cgagagcctt cgctgactcc a ccgaagaag    240
```

-continued

```
tgcaccactg gggaccaccc agtgccaggc gcccgtccag ggacacacac a gtcttcact    300

g                                                                   301

<210> SEQ ID NO 19
<211> LENGTH: 301
<212> TYPE: DNA
<213> ORGANISM: Human

<400> SEQUENCE: 19

agaatctctg cactgtcatc aggtacaaca aaagatcaaa cccctgtccc g atgttaact     60

ttttaactta aaagaatgcc agaaaaccca gatcaacact ttccagctac g agccgtcca    120

caaaggccac ccaaaggcca gtcagactcg tgcagatctt attttttaat a gtagtaacc    180

acaatacaca gctctttaaa gctgttcata ttcttccccc attaaacacc t gccccgggc    240

ggccaagggc gaattctgca gatatccatc acactggcgg ccgctcgagc a tgcatctag    300

a                                                                   301

<210> SEQ ID NO 20
<211> LENGTH: 290
<212> TYPE: DNA
<213> ORGANISM: Human

<400> SEQUENCE: 20

aggttttttt tttttttttt tttttttttt tttttccctt tcaattcatt t aatttcaac     60

aatctgtcaa aaaacagcca ataaacaaat actgaattac attctgctgg g ttttttaaa    120

ggctctaaac tataaaaaca tcttgtgtct cccaccctga ccaccctgct a cttttccat    180

ataccacagg ccacccataa acacaaagcc agggggtgaa gctgacatgg t ctatttgga    240

gccagtaaac aggagggcga taagtcctga taagcactta tggacaatat              290

<210> SEQ ID NO 21
<211> LENGTH: 301
<212> TYPE: DNA
<213> ORGANISM: Human

<400> SEQUENCE: 21

agaaaggtaa ctgccagcca ggcttgcatt gtttagccag aaattgctgc t tggttctag     60

actctttaaa aaaaaaaaat acccagggtt tgtcatcatt ttcagaggca g agtgccaaa    120

tatcacccaa agctcttgtg tctttttttt accccttat tttattttta t ttattaatt    180

ttttgtgcaa acatcaaatg tcactggtgt tcacagaagg cttttttgac t agccttaaa    240

ttcctgagtc aaaagattaa tcagattttc aggcagtgtt taatcaggtg c tttgtcctg    300

t                                                                   301

<210> SEQ ID NO 22
<211> LENGTH: 301
<212> TYPE: DNA
<213> ORGANISM: Human

<400> SEQUENCE: 22

gacgccatgc accctccggt aaccagcagc cgcctgtcca tcccccaaga c cggaaaggc     60

agcagcagcc cccgggagcc cagggctgtc ctcggtgcat ctggctgcag a gggaaattg    120

atgaccttac acagcaacta gcggccatgc agtccttcac tgacaagttc c aggaccttt    180

gaagttggag ccagcgtccg gagctgcagc caagcgagtt tcctccttat c ctccttagc    240
```

-continued

```
cagggctttt tctcttccgc tgcatttgcc cccttcccaa cgcaattcaa a gcagttgtg    300

a                                                                   301


<210> SEQ ID NO 23
<211> LENGTH: 381
<212> TYPE: DNA
<213> ORGANISM: Human

<400> SEQUENCE: 23

cgaggtccag acagtggacc aagagatacg ctacataaat tggggtttca c aattcttac     60

attatttgtc tgtcacagaa gagagctgct tatgattttg aaggggtcag g gagggtggg    120

agttggtaaa gagtagggta tttctataac agatattatt cagtcttatt t cctaagatt    180

ttgttgtaac ttaaggtatc ttgctacagt agacagaatt ggtaatagca a cttttaaaa    240

ttgtcattag ttctgcaata ttagctgaaa tgtagtacag aaaagaatgt a catttagac    300

atttgggttc agttgcttgt agtctgtaaa tttaaaacag cttaatttgg t acaggttac    360

acatatggac ctcccgggcg g                                             381


<210> SEQ ID NO 24
<211> LENGTH: 214
<212> TYPE: DNA
<213> ORGANISM: Human

<400> SEQUENCE: 24

aatgatgtaa aaattaatca acagggctgc cacttgcgaa tcccctccaa g gatgctgtg     60

caaagggtct cattggtcct gatgaataat cttgtgactg tacatattcc t gggtgcatg    120

tccacaaata ctgaggtata gcctgcatgc cactaaaaat aacaaaggtt t caggggtgg    180

aaacattgtc caccacactg tcatgaccat cttt                               214


<210> SEQ ID NO 25
<211> LENGTH: 302
<212> TYPE: DNA
<213> ORGANISM: Human

<400> SEQUENCE: 25

gggggcactg agaactccct ctggaattct tggggggtgt tggggagaga c tgtgggcct     60

ggagataaaa cttgtctcct ctaccaccac cctgtaccct agcctgcacc t gtcctcatc    120

tctgcaaagt tcagcttcct tccccaggtc tctgtgcact ctgtcttgga t gctctgggg    180

agctcatggg tggaggagtc tccaccagag ggaggctcag ggactggttt g ggccaggga    240

tgaatatttg agggataaaa attgtgtaag aagccaaaga aattggtagt a gggggagaa    300

ac                                                                  302


<210> SEQ ID NO 26
<211> LENGTH: 301
<212> TYPE: DNA
<213> ORGANISM: Human

<400> SEQUENCE: 26

ttggagaacg cgctgacata ctgctcggcc acagtcagtg aagctgctgc a tctccatta     60

tgttgtgtca gagctgcagc caggattcga atagcttcag ctttagcctt g gccttcgcc    120

agaactgcac tggcctctcc tgctgcctga tttatctgtg cagccttttc t gcttcggag    180

gccaggatct gggcctgttt cttcccttct gccacattga tggccgactc t cgggtcccc    240

tcagactcta gaactgtggc ccgtttccgc cgctctgcct ccacctgcat c tgcatagac    300
```

```
t                                                                   301

<210> SEQ ID NO 27
<211> LENGTH: 301
<212> TYPE: DNA
<213> ORGANISM: Human

<400> SEQUENCE: 27

aaatcagtca tcacatctgt gaaaagagtg ctagttataa caaatgagat c acaaatttg     60

accattttat tagacaccct ctattagtgt taacagacaa agatgaaggt t aagttgaaa    120

tcaaattgaa atcatcttcc ctctgtacag attgcaatat ctgataatac c ctcaacttt    180

cttggtgcaa attaattgcc tggtactcac agtccagtgt taacaggcaa t aatggtgtg    240

attccagagg agaggactag gtggcaggaa aataaatgag attagcagta t ttgacttgg    300

a                                                                   301

<210> SEQ ID NO 28
<211> LENGTH: 286
<212> TYPE: DNA
<213> ORGANISM: Human

<400> SEQUENCE: 28

tttttttttg cacaggatgc acttattcta ttcattctcc cccacccttc c catatttac     60

atccttagag gaagagaggg gtaaggtgat aaagtaactg aaggaccgca a gacgggtat    120

gtcccttgtt caccaaatgg tcaaagggtc aaagatcgga ggaggtcagg g ggtaacgca    180

ggaacaggtg agggcgtttc gccctctctc cctctcccct tttcaacctc t taatcactg    240

gctaactcgc gacctcatgg gttaattcgt aagcttacac gcgttg                  286

<210> SEQ ID NO 29
<211> LENGTH: 301
<212> TYPE: DNA
<213> ORGANISM: Human

<400> SEQUENCE: 29

gtcatgttct tgctcttcct tctttacaca tttgagttgt gccttctgtt c ttaaagaga     60

ttttcctttg ttcaaaggat ttattcctac catttcacaa atccgaaaat a attgaggaa    120

acaggttaca tcattccaat tttgccttgg gtttgaagag tctctcatgg t ggcacagtc    180

ctccagggta gctatgttgt tgggctcccc tacatcccag aagctcagag a ctttgtcaa    240

aggtgtgccg tccacccatt gccactgacc ctcgacaacc tggtctgaca g tccaataaa    300

a                                                                   301

<210> SEQ ID NO 30
<211> LENGTH: 332
<212> TYPE: DNA
<213> ORGANISM: Human

<400> SEQUENCE: 30

gagcagaatt gatgcctatg gctccaagtc aaatactgct aatctcattt a ttttcctgc     60

cacctagtcc tctcctctgg aatcacacca ttattgcctg ttaacactgg a ctgtgagta    120

ccaggcaatt aatttgcacc aagaaagttg agggtattat cagatattgc a atctgtaca    180

gagggaagat gatttcaatt tgatttcaac ttaaccttca tctttgtctg t taacactaa    240

tagagggtgt ctaataaaat ggtcaaattt gtgatctcat ttgttataac t agcactctt    300
```

-continued

```
ttcacagatg tgatgactga tttccagcag ac                                 332


<210> SEQ ID NO 31
<211> LENGTH: 141
<212> TYPE: DNA
<213> ORGANISM: Human

<400> SEQUENCE: 31

aaaggctatc aagtactttg aaggacagga aggaatgaac acacccaggt g gacgtttgg     60

tttcatttgc aggggttcag ggagggttgc aggggttcag ggagggctct t gtcccacaa    120

ccgggggaag ggagagggca c                                             141


<210> SEQ ID NO 32
<211> LENGTH: 201
<212> TYPE: DNA
<213> ORGANISM: Human

<400> SEQUENCE: 32

gagctgatct cacagcacat acagaatgat gctactatgt agaccctcac t cccttggga     60

aatctgtcat ctaccttaaa gagagaaaaa agatggaaca taggcccacc t agtttcatc    120

catccaccta cataaccaac atagatgtga ggtccactgc actgatagcc a gactgcctg    180

gggtaaacct tttcagggag g                                             201


<210> SEQ ID NO 33
<211> LENGTH: 181
<212> TYPE: DNA
<213> ORGANISM: Human

<400> SEQUENCE: 33

tttcaaaaca ctcatatgtt gcaaaaaaca catagaaaaa taaagtttgg t gggggtgct     60

gactaaactt caagtcacag acttttatgt gacagattgg agcagggttt g ttatgcatg    120

tagagaaccc aaactaattt attaaacagg atagaaacag gctgtctggg t gaaatggtt    180

c                                                                   181


<210> SEQ ID NO 34
<211> LENGTH: 151
<212> TYPE: DNA
<213> ORGANISM: Human

<400> SEQUENCE: 34

atgtcctgca cagtatagct tggacctctg ggcctgaacc agggtgagca t caaggcccc     60

catttctcct caccacgggg tcgcttgtca gctccaagaa ccagtctggc c ccactgaga    120

acttttcagt cgagggcctg atgaatcttg g                                  151


<210> SEQ ID NO 35
<211> LENGTH: 291
<212> TYPE: DNA
<213> ORGANISM: Human

<400> SEQUENCE: 35

tctttagggc aaaatcatgt ttctgtgtac ctagcaatgt gttcccattt t attaagaaa     60

agctttaaca cgtgtaatct gcagtcctta acagtggcgt aattgtacgt a cctgttgtg    120

tttcagtttg tttttcacct ataatgaatt gtaaaaacaa acatacttgt g ggtctgat     180

agcaaacata gaaatgatgt atattgtttt ttgttatcta tttattttca t caatacagt    240

attttgatgt attgcaaaaa tagataataa tttatataac aggttttctg t            291
```

<210> SEQ ID NO 36
<211> LENGTH: 201
<212> TYPE: DNA
<213> ORGANISM: Human

<400> SEQUENCE: 36

```
ctgatacaat tataataacg gttccctgaa ccttttagag tgcaattaag a acaaaaact     60
aaattttgtt tacatgaata tggaataaat acaataatca aaatatgact c tccctaaaa    120
gtgaaacaca caagccaatc cggaactgct gtgcgaaaga taaaatcgag a aaggcaagg    180
tttcggtagg aggacgcgat g                                              201
```

<210> SEQ ID NO 37
<211> LENGTH: 121
<212> TYPE: DNA
<213> ORGANISM: Human

<400> SEQUENCE: 37

```
catcacactg gcggccgctc gagcatgcat ctagagggcc caattcgccc t ataatgagt     60
cgtattacaa ttcactggcc gtcgttttac aacgtcgtga ctgggaaaac c ctggcgtta    120
c                                                                    121
```

<210> SEQ ID NO 38
<211> LENGTH: 200
<212> TYPE: DNA
<213> ORGANISM: Human

<400> SEQUENCE: 38

```
aaacatgtat tactctatat ccccaagtcc tagagcatga cctgcatgtt g gagatgttg     60
tacagcaatg tatttatcca gacatacata tatgatattt agagacacag t gattctttt    120
gataacacca cacatagaac attataatta cacacaaatt tatggtaaaa g aattaatat    180
gctgtctggt gctgctgtta                                                200
```

<210> SEQ ID NO 39
<211> LENGTH: 760
<212> TYPE: DNA
<213> ORGANISM: Human

<400> SEQUENCE: 39

```
gcgtggtcgt cggccgaggt cctgggctag acctaatggt ttattattgg t ggagagaaa     60
gatctggaaa tacttgaggt tattacatac tagattagct tctaatgtga a ccatttttc    120
ttttaacagt gatcaaatta ttatttcgaa gttaatcgtt cccttggtgg c tgcatacac    180
atcgcattaa caaacatact gttgtatttt ttcccagttt tgtttggcta t gccaccaca    240
gtcatcccca gggtctatac atactatgtt tcaactgtat tatttgccat t tttggcatt    300
agaatgcttc gggaaggctt aaagatgagc cctgatgagg gtcaagagga a ctggaagaa    360
gttcaagctg aattaaagaa gaaagatgaa gaagtaagcc atggcactgt t gatctggac    420
caaaaaggca ctcaactagg aataaacact ctacagaggt ttctcagtgg c cccatctgt    480
gtgatatgcg gggctacaca aaaatagctt cttttgcttt gttctgttct t atacctgtc    540
tgtgatctga cttggggttg gtgtgaatgt agtagagaaa ggaagctgac a gatgaatac    600
tgaacacagg taatcagttt ccttaattag gttgattata agctcctgaa a agcaggaac    660
tgtattttat aattttacct gtttctcccg tggtgtctag gatagtaagt g agcagagca    720
```

-continued

```
gtaaatactg tttggtttgt tcagacctgc ccgggcggcc                          760


<210> SEQ ID NO 40
<211> LENGTH: 452
<212> TYPE: DNA
<213> ORGANISM: Human

<400> SEQUENCE: 40

aatcactaaa gatattgact agagaatgct gtgtgctatt tcaattacat t tgtttttct     60

tttattaaca ggaattttga ttcttcaagg aagtggctca atttcaattt c aggtgacca    120

ggtttatcgt gacttttcct tcttgtttac ttttcgctag gaaggggagt t gtaggggca    180

gattcaggta ttggaatagg aaaattacgt ctaaaccatg gaaatcttgg a aatggaatt    240

ggtggaagtg ggcgaaatgg atatgggtaa gggaacacaa aaaaccctga a gctaattca    300

tcgctgtcac tgatacttct tttttctcgt tcctggtctt gagagactgg g aaaccaaca    360

gccactgcca agatggctgt gatcaggagg agaactttct tcatctcaaa c gtttcagtc    420

agttctttct ctcacctcgg ccgcgaccac gc                                   452


<210> SEQ ID NO 41
<211> LENGTH: 676
<212> TYPE: DNA
<213> ORGANISM: Human

<400> SEQUENCE: 41

aatctttgaa tgccaagtct cttctgtact ttcttttatt aacatcatag t ctttgcatc     60

aagatacata gcaatgatag caggtttctt tttaaagctt agtattaata t taaatattt    120

ttccccattt aaattttaca ttacttgcca agaaaaaaaa aaaattaaaa c tcaagttac    180

ttgaagcctg gacacacttc catgattagc cgggctaggt aaaagttggt g gctttattc    240

ttcctgctct ataagcagat ccaggcccta gaaagatggg accagggtat a taattgttt    300

ttgaaaagtg tgctacaaaa atggatggcc tgttataagc caggatacaa a gttaaggat    360

gggggtaagg gagggacatt ttcttccaga agaaaagaca gaatttctga a gagtcccag    420

tccataattt tcccaaaatg gttggaggag agggtaaaat ctcaacatga g tttcaaagt    480

actgtctctg tgaggggccg gtagatgcct tgctgaggag ggatggctaa t ttggaccat    540

gccccatccc cagctaggag aatggaaatg gaaactttaa ttgcccagtg g gtgtgaaag    600

tgggctgaag cttggttggt actgaattct ctaagaggtt tcttctagaa a cagacaact    660

cagacctgcc cgggcg                                                     676


<210> SEQ ID NO 42
<211> LENGTH: 468
<212> TYPE: DNA
<213> ORGANISM: Human

<400> SEQUENCE: 42

agcgtggtcg cggccgaggt ttggccggga gcctgatcac ctgccctgct g agtcccagg     60

ctgagcctca gtctccctcc cttggggcct atgcagaggt ccacaacaca c agatttgag    120

ctcagccctg gtgggcagag aggtagggat ggggctgtgg ggatagtgag g catcgcaat    180

gtaagactcg ggattagtac acacttgttg attaatggaa atgtttacag a tccccaagc    240

ctggcaaggg aatttcttca actccctgcc ccccagccct ccttatcaaa g gacaccatt    300

ttggcaagct ctatgaccaa ggagccaaac atcctacaag acacagtgac c atactaatt    360

aaaacccct gcaaagccca gcttgaaacc ttcacttagg aacgtaatcg t gtcccctat    420
```

-continued

```
cctacttccc cttcctaatt ccacagacct gcccgggcgg ccgctcga              468


<210> SEQ ID NO 43
<211> LENGTH: 408
<212> TYPE: DNA
<213> ORGANISM: Human

<400> SEQUENCE: 43

atcatatcaa aacactatct tcccatctgt ttctcaatgc ctgctacttc t tgtagatat     60

ttcatttcag gagagcagca gttaaacccg tggattttgt agttaggaac c tgggttcaa    120

acctctttcc actaattggc tatgtctctg gacagttttt tttttttttt t tttttttaa    180

accctttctg aactttcact ttctatggct acctcaaaga attgttgtga g gcttgagat    240

aatgcatttg taaagggtct gccagatagg aagatgctag ttatggattt a caaggttgt    300

taaggctgta agagtctaaa acctacagtg aatcacaatg catttacccc c actgacttg    360

gacataagtg aaaactagcc cgaagtctct ttttcaaatt acttacag              408


<210> SEQ ID NO 44
<211> LENGTH: 160
<212> TYPE: DNA
<213> ORGANISM: Human

<400> SEQUENCE: 44

tggtcgcggc cgaggtcttg tgtgccctgt ggtccagggg accaagaaca a caagatcca     60

ctctctgtgc tacaatgatt gcaccttctc acgcaacact ccaaccagga c tttcaacta    120

caacttctcc gctttggcaa acaccgtcac tcttgctgga                        160


<210> SEQ ID NO 45
<211> LENGTH: 231
<212> TYPE: DNA
<213> ORGANISM: Human

<400> SEQUENCE: 45

cgagcggccg cccgggcagg tctggggagg tgattccatc cagagtcata t ctgttgtca     60

ccccaataag tcgatcagca aggctgacag gctgtgagga aaccccggcc t tgtagcctg    120

tcacctctgg ggggatgatg actgcctggc agacgtaggc tgtgatagat t tgggagaaa    180

acctgactca ccctcaggaa tccggaggtc ggtgacattg tcggtgcaca c              231


<210> SEQ ID NO 46
<211> LENGTH: 371
<212> TYPE: DNA
<213> ORGANISM: Human

<400> SEQUENCE: 46

cccgggcagg tctgtgtaac atgccaaggc tttgcacttt ctgcagagca g tttttttatt     60

ttccttatca ggtacaggtt ttggtttttc ttgactatct ctgatgaatt t ttcatgagt    120

ctgtatatgc agaatctttt ccctaaatac tgcttcgtcc catgtctgaa g gcgtaaaat    180

aaagtcattc atcatttttt ctttgtacat gtttatttgt tctttttcaa t tacaccaag    240

cattactagt cagaaggaag cacttgctac ctcttgctct tcctctgcct c tggtttgga    300

tcattttgat gacattgccc acattactca tgaaggatga caagattgca c tgtgcaatg    360

tcaattgcct t                                                        371


<210> SEQ ID NO 47
```

-continued

<211> LENGTH: 261
<212> TYPE: DNA
<213> ORGANISM: Human

<400> SEQUENCE: 47

```
gccctgtttt tatacacttc acatttgcag aaatataatg atgccctcat t atcagtgag     60
catgcacgaa tgaaagatgc tctggattac ttgaaagact tcttcagcaa t gtccgagca    120
gcaggattcg atgagattga gcaagatctt actcagagat ttgaagaaaa g ctgcaggaa    180
ctagaaagtg tttccaggga tcccagcaat gagaatccta aacttgaaga c ctctgcttc    240
atcttacaag aagagtacca c                                              261
```

<210> SEQ ID NO 48
<211> LENGTH: 701
<212> TYPE: DNA
<213> ORGANISM: Human

<400> SEQUENCE: 48

```
cgagcggccc ccgggcaggt ccaattagta caagtctcat gatataatca c tgcctgcat     60
acatatgcac agatccagtt agtgagtttg tcaagcttaa tctaattggt t aagtctcaa    120
agagattatt attcttgatg tttgctttgt attggctaac aaatgtgcag a ggtaataca    180
tatgtgatgt ccgatgtctc tgtctttttt tttgtcttta aaaaataatt g gcagcaact    240
gtatttgaat aaaatgattt cttagtatga ttgtaccgta atgaatgaaa g tggaacatg    300
tttctttttg aaagggagag aattgaccat ttattattgt gatgtttaag t tataactta    360
ttgagcactt ttagtagtga taactgtttt taaacttgcc taataccttt c ttgggtatt    420
gtttgtaatg tgacttattt aaccccottt tttgtttgtt taagttgctg c tttaggtta    480
acagcgtgtt ttagaagatt taaatttttt tcctgtctgc acaattagtt a ttcagagca    540
agagggcctg attttataga agccccttga aaagaggtcc agatgagagc a gagatacag    600
tgagaaatta tgtgatctgt gtgttgtggg aagagaattt tcaatatgta a ctacggagc    660
tgtagtgcca ttagaaactg tgaatttcca aataaatttg a                         701
```

<210> SEQ ID NO 49
<211> LENGTH: 270
<212> TYPE: DNA
<213> ORGANISM: Human

<400> SEQUENCE: 49

```
agcggccgcc cgggcaggtc tgatattagt agctttgcaa ccctgataga g taaataaat     60
tttatgggcg ggtgccaaat actgctgtga atctatttgt atagtatcca t gaatgaatt    120
tatggaaata gatatttgtg cagctcaatt tatgcagaga ttaaatgaca t cataatact    180
ggatgaaaac ttgcatagaa ttctgattaa atagtgggtc tgtttcacat g tgcagtttg    240
aagtatttaa attaaccact cctttcacag                                     270
```

<210> SEQ ID NO 50
<211> LENGTH: 271
<212> TYPE: DNA
<213> ORGANISM: Human

<400> SEQUENCE: 50

```
atgcatttat ccatatgaac ttgattattc tgaattactg actataaaaa g gctattgtg     60
aaagatatca cactttgaaa cagcaaatga attttcaatt ttacatttaa t tataagacc    120
acaataaaaa gttgaacatg cgcatatcta tgcatttcac agaagattag t aaaactgat    180
```

-continued ggcaacttca gaattatttc atgaagggta caaacagtct ttaccacaat t ttcccatgg 240 tcttatcctt caaaataaaa ttccacacac t 271

<210> SEQ ID NO 51
<211> LENGTH: 241
<212> TYPE: DNA
<213> ORGANISM: Human

<400> SEQUENCE: 51
tggtcgcggc cgaggtgtga ggagatgaac tttgtgttaa tggggggcac t ttaaatcga 60 aatggcttat ccccaccgcc atgtaagtta ccatgcctgt ctcctccctc c tacacattt 120 ccagctcctg ctgcagttat tcctacagaa gctgccattt accagccctc t gtgattttg 180 aatccacgag cactgcaggc cctccacagc gttactaccc agcaggcact c agctcttca 240 t 241

<210> SEQ ID NO 52
<211> LENGTH: 271
<212> TYPE: DNA
<213> ORGANISM: Human

<400> SEQUENCE: 52
tccaagactt aaaacttagg aaacacctat gatgccactt taactggaag t aatggagac 60 atctgattcc aaattcacat tttaaatgcc tatttgcaat cagcaaagag c caggtatgc 120 tgcatgctgc ttgctgtaag ttacgatttg gcttcactag ctcaaatttt t tcactccac 180 caaaagataa ggcacaggcc cgtttgtcca atcaagtttg ctgaaaatac t gcagcctga 240 gtgtagacaa acttcccctg aatttgctag a 271

<210> SEQ ID NO 53
<211> LENGTH: 493
<212> TYPE: DNA
<213> ORGANISM: Human

<400> SEQUENCE: 53
ttagcgtggt cgcggtccga ggtctggcct gactagctca ctctgaagag t gtctttcac 60 atggattaac caaaaaatgc attactgcct ttggcacact gtcttgaata t tctttctga 120 caatgagaaa atatgattta atggagtcgt tcaataacct cacaatctcg c tgttccgag 180 cagatagttt tcgtgccaac aggaactggc acatctagca ggttcacggc a tgaccttt 240 tgtggactgg ctggcataat tggaatgggt tttgattttt cttctgctaa t aactcttca 300 agcttttgaa gttttcaagc attcctctcc agttgcctgt ggttggttct t gaacaccat 360 ctccaacccc accacctcca gatgcaacct tgtctcgtga tacagacctg c ccgggcggc 420 cctcaagggc gaattctgca gatatccatc acactggcgg ccgctcgagc a tgcatctag 480 agggcccaat tcg 493

<210> SEQ ID NO 54
<211> LENGTH: 321
<212> TYPE: DNA
<213> ORGANISM: Human

<400> SEQUENCE: 54
cgtggtcgcg gccgaggtct gtttgcttgt tggtgtgagt ttttcttctg g agactttgt 60 actgaatgtc aataaactct gtgattttgt taggaagtaa aactgggatc t atttagcca 120

```
ctggtaagct tctgaggtga aggattcagg gacatctcgt ggaacaaaca c tccccactg    180

gactttctct ctggagatac ccttttgaat atacaatggc cttggctcac t aggtttaaa    240

tacaaacaag tctgaaaccc actgaagact gagagattgc agcaatattc t ctgaattag    300

gatcgggttc cataactcta a                                              321


<210> SEQ ID NO 55
<211> LENGTH: 281
<212> TYPE: DNA
<213> ORGANISM: Human

<400> SEQUENCE: 55

ttgcaaatga aactgtggat gtataataag aaaacacaag ggtttattct t aacactaaa     60

attaacatgc cacacgaaga ctgcattaca gctctctgtt tctgtaatgc a gaaaaatct    120

gaacagccca ccttggttac agctagcaaa gatggttact tcaaagtatg g atattaaca    180

gatgactctg acatatacaa aaaagctgtt ggctggacct gtgactttgt t ggtagttat    240

cacaagtatc aagcaactaa ctgttgtttc tccgaagatg g                        281


<210> SEQ ID NO 56
<211> LENGTH: 612
<212> TYPE: DNA
<213> ORGANISM: Human

<400> SEQUENCE: 56

gcgtggtcgc ggccgaggtc ctgtccgggg gcactgagaa ctccctctgg a attcttggg     60

gggtgttggg gagagactgt gggcctggag ataaaacttg tctcctctac c accaccctg    120

taccctagcc tgcacctgtc ctcatctctg caaagttcag cttccttccc c aggtctctg    180

tgccactctg tcttggatgc tctggggagc tcatgggtgg aggagtctcc a ccagaggga    240

ggctcagggg actggttggg ccagggatga atatttgagg gataaaaatt g tgtaagagc    300

caaagaattg gtagtagggg gagaacagag aggagctggg ctatgggaaa t gatttgaat    360

aatggagctg ggaatatggc tggatatctg gtactaaaaa agggtcttta a gaacctact    420

tcctaatctc ttccccaatc caaaccatag ctgtctgtcc agtgctctct t cctgcctcc    480

agctctgccc caggctcctc ctagactctg tccctgggct agggcagggg a ggagggaga    540

gcagggttgg gggagaggct gaggagagtg tgacatgtgg ggagaggacc a gacctgccc    600

gggcggccgt cg                                                        612


<210> SEQ ID NO 57
<211> LENGTH: 363
<212> TYPE: DNA
<213> ORGANISM: Human

<400> SEQUENCE: 57

gtcgcggccg aggtcctgag cgtcacccta gttctgcccc tttttagctg t gtagacttg     60

gacaagacat ttgacttccc tttctccttg tctataaaat gtggacagtg g acgtctgtc    120

acccaagaga gttgtgggag acaagatcac agctatgagc acctcgcacg g tgtccagga    180

tgcacagcac aatccatgat gcgttttctc cccttacgca ctttgaaacc c atgctagaa    240

aagtgaatac atctgactgt gctccactcc aacctccagc gtggatgtcc c tgtctgggc    300

ccttttctg tttttattc tatgttcagc accactggca ccaaatacat t ttaattcac    360

cga                                                                  363
```

-continued

<210> SEQ ID NO 58
<211> LENGTH: 750
<212> TYPE: DNA
<213> ORGANISM: Human

<400> SEQUENCE: 58

```
cgtggtcgcg gccgaggtct aattccacct gactggcaga acctgcgccc c tcgcctaac     60
ctgcgccctt ctcccaactc gcgtgcctca cagaacccag gtgctgcaca g ccccgagat    120
gtggcccttc ttcaggaaag agcaaataag ttggtccaag tacttgatgc t taaggaata    180
cacaaaggtg cccatcaagc gctcagaaat gctgagagat atcatccgtg a atacactga    240
tgtttatcca gaaatcattg aacgtgcatg ctttgtccta gagaagaaat t tgggattca    300
actgaaagaa attgacaaag aagaacacct gtatattctc atcagtaccc c cgagtccct    360
ggctggcata ctgggaacga ccaaagacac acccaagctc ggtctcttct t ggtgattct    420
gggtgtcatc ttcatgaatg gcaaccgtgc cagtgaggct gtcttttggg a ggcactacg    480
caagatggga ctgcgtcctg ggtgagaca tcccctccct tggagatcta a ggaaacttc    540
tcacctatga gtttgtaaag cagaaatacc tggactacag acgagtgccc a acagcaacc    600
ccccggagta tgagttcctc tggggcctcc gtccctacca tgagactagc a agatgaaaa    660
tgctgagatt cattgcagag gttcagaaaa gagaccctcg tgactggact g cacagttca    720
tggaggctgc agatgaggac ctgcccgggc                                      750
```

<210> SEQ ID NO 59
<211> LENGTH: 505
<212> TYPE: DNA
<213> ORGANISM: Human

<400> SEQUENCE: 59

```
tggccgcccg ggcaggtcca gtctacaagc agagcactct catggggagc a ccagatgag     60
ttccagccgc agttctttta taagctttaa gtgcctcatg aagacgcgag g atctcttcc    120
aagtgcaacc tggtcacatc agggcacatt cagcagcaga agtctgtttc c agtatagtc    180
cttggtatgg ctaaattcca ctgtcccttt ctcagcagtc aataatccat g ataaattct    240
gtacaacact gtagtcaata acagcagcac cagacagcat attaattctt t taccataaa    300
tttgtgtgta attataatgt tctatgtgtg gtgttatcaa aagaatcact g tgtctctaa    360
atatcatata tgtatgtctg gataaataca ttgctgtaca acatctccaa c atgcaggtc    420
atgctctaag acttggggat atagagtaat acatgtttcg tggacctcgg c cgcgaccac    480
gctaagggcg aattctgcag atatc                                           505
```

<210> SEQ ID NO 60
<211> LENGTH: 520
<212> TYPE: DNA
<213> ORGANISM: Human

<400> SEQUENCE: 60

```
cgtggtcgcg gccgaggtcc tcaggacaag gaaacaggta tcagcatgat g gtagcagaa     60
accttatcac caaggtgcag gagctgactt cttccaaaga gttgtggttc c gggcagcgg    120
tcattgcctg cccttgctgg agggctgatt ttagtgttgc ttattatgtt g gccctgagg    180
atgcttcgaa gtgaaaataa gaggctgcag gatcagcggc aacagatgct c tcccgtttg    240
cactacagct ttcacggaca ccattccaaa aaggggcagg ttgcaaagtt a gacttggaa    300
tgcatggtgc cggtcagtgg gcacgagaac tgctgtctga cctgtgataa a atgagacaa    360
```

-continued

```
gcagacctca gcaacgataa gatcctctcg cttgttcact ggggcatgta c agtgggcac    420

gggaagctgg aattcgtatg acggagtctt atctgaacta cacttactga a cagcttgaa    480

ggacctgccc gggcggccgc tcgaaagggg cgaattctgc                          520
```

```
<210> SEQ ID NO 61
<211> LENGTH: 447
<212> TYPE: DNA
<213> ORGANISM: Human

<400> SEQUENCE: 61

agagaggtgt ttttattctt tggggacaaa gccgggttct gtgggtgtag g attctccag     60

gttctccagg ctgtagggcc cagaggctta atcagaattt tcagacaaaa c tggaacctt    120

tctttttccc cgttggttta tttgtagtcc ttgggcaaac caatgtcttt g ttcgaaaga    180

gggaaaataa tccaaacgtt tttcttttaa cttttttttt aggttcaggg g cacatgtgt    240

aggcttgcta tataggtaaa ttgcatgtca ccagggtttg ttgtacagat t atttcatca    300

tccagataaa aagcatagta ccagataggt agtttttttga tcctcaccct c cttccatgc    360

tccgacctca ggtaggcccc agtgtctgac ctgcccggcg gcccgctcga a agggccaat    420

tctgcagata tccatcacac tggccgg                                        447
```

```
<210> SEQ ID NO 62
<211> LENGTH: 83
<212> TYPE: PRT
<213> ORGANISM: Human

<400> SEQUENCE: 62

Lys Lys Val Leu Leu Leu Ile Thr Ala Ile L eu Ala Val Ala Val Gly
 1               5                  10                  15

Phe Pro Val Ser Gln Asp Gln Glu Arg Glu L ys Arg Ser Ile Ser Asp
            20                  25                  30

Ser Asp Glu Leu Ala Ser Gly Phe Phe Val P he Pro Tyr Pro Tyr Pro
        35                  40                  45

Phe Arg Pro Leu Pro Pro Ile Pro Phe Pro A rg Phe Pro Trp Phe Arg
    50                  55                  60

Arg Asn Phe Pro Ile Pro Ile Pro Ser Ala P ro Thr Thr Pro Leu Pro
65                  70                  75                  80

Ser Glu Lys
```

```
<210> SEQ ID NO 63
<211> LENGTH: 683
<212> TYPE: DNA
<213> ORGANISM: Human

<400> SEQUENCE: 63

acaaagattg gtagctttta tatttttta aaaatgctat actaagagaa a aaacaaaag     60

accacaacaa tattccaaat tataggttga gagaatgtga ctatgaagaa a gtattctaa    120

ccaactaaaa aaaatattga aaccactttt gattgaagca aaatgaataa t gctagattt    180

aaaaacagtg tgaaatcaca ctttggtctg taaacatatt tagctttgct t ttcattcag    240

atgtatacat aaacttattt aaaatgtcat ttaagtgaac cattccaagg c ataataaaa    300

aaagwggtag caaatgaaaa ttaaagcatt tattttggta gttcttcaat a atgatrcga    360

gaaactgaat tccatccagt agaagcatct ccttttgggt aatctgaaca a gtrccaacc    420

cagatagcaa catccactaa tccagcacca attccttcac aaagtccttc c acagaagaa    480
```

-continued

```
gtgcgatgaa tattaattgt tgaattcatt tcagggcttc cttggtccaa a taaattata    540

gcttcaatgg gaagaggtcc tgaacattca gctccattga atgtgaaata c caacgctga    600

cagcatgcat ttctgcattt tagccgaagt gagccactga acaaaactct t agagcacta    660

tttgaacgca tctttgtaaa tgt                                            683
```

<210> SEQ ID NO 64
<211> LENGTH: 749
<212> TYPE: DNA
<213> ORGANISM: Human
<220> FEATURE:
<221> NAME/KEY: modified_base
<222> LOCATION: (534)
<223> OTHER INFORMATION: Where n is a, c, g or t

<400> SEQUENCE: 64

```
ctgttcattt gtccgccagc tcctggactg gatgtgtgaa aggcatcaca t ttccatttt     60

cctccgtgta aatgttttat gtgttcgcct actgatccca ttcgttgctt c tattgtaaa    120

tatttgtcat ttgtatttat tatctctgtg ttttccccct aaggcataaa a tggtttact    180

gtgttcattt gaacccattt actgatctct gttgtatatt tttcatgcca c tgctttgtt    240

ttctcctcag aagtcgggta gatagcattt ctatcccatc cctcacgtta t tggaagcat    300

gcaacagtat ttattgctca gggtcttctg cttaaaactg aggaaggtcc a cattcctgc    360

aagcattgat tgagacattt gcacaatcta aaatgtaagc aaagtaagtc a ttaaaaata    420

caccctctac ttgggcttta tactgcatac aaatttactc atgagccttc c tttgaggaa    480

ggatgtggat ctccaaataa agatttagtg tttattttga gctctgcatc t tancaagat    540

gatctgaaca cctctccttt gtatcaataa atagccctgt tattctgaag t gagaggacc    600

aagtatagta aaatgctgac atctaaaact aaataaatag aaaacaccag g ccagaacta    660

tagtcatact cacacaaagg gagaaattta aactcgaacc aagcaaaagg c ttcacggaa    720

atagcatgga aaaacaatgc ttccagtgg                                      749
```

<210> SEQ ID NO 65
<211> LENGTH: 612
<212> TYPE: DNA
<213> ORGANISM: Human

<400> SEQUENCE: 65

```
acagcagcag tagatggctg caacaacctt cctcctaccc cagcccagaa a atatttctg     60

ccccacccca ggatccggga ccaaaataaa gagcaagcag gccccccttca c tgaggtgct    120

gggtagggct cagtgccaca ttactgtgct ttgagaaaga ggaaggggat t tgtttggca    180

ctttaaaaat agaggagtaa gcaggactgg agaggccaga gaagatacca a aattggcag    240

ggagagacca tttggcgcca gtcccctagg agatgggagg agggagatag g tatgagggt    300

aggcgctaag aagagtagga ggggtccact ccaagtggca gggtgctgaa a tgggctagg    360

accaacagga cactgactct aggtttatga cctgtccata cccgttccac a gcagctggg    420

tgggagaaat caccattttg tgacttctaa taaaataatg ggtctaggca a cagttttca    480

atggatgcta aaacgattag gtgaaaagtt gatggagaat tttaattcag g ggaattagg    540

ctgataccat ctgaaaccat ttggcatcat taaaaatgtg acaacctggt g gctgccagg    600

gaggaagggg ag                                                        612
```

<210> SEQ ID NO 66
<211> LENGTH: 703

<212> TYPE: DNA
<213> ORGANISM: Human

<400> SEQUENCE: 66

```
tagcgtggtc gcggccgagg tacattgatg ggctggagag cagggttggc a gcctgttct     60
gcacagaacc aagaattaca gaaaaaagtc caggagctgg agaggcacaa c atctccttg    120
gtagctcagc tccgccagct gcagacgcta attgctcaaa cttccaacaa a gctgcccag    180
accagcactt gtgttttgat tcttcttttt tccctggctc tcatcatcct g cccagcttc    240
agtccattcc agagtcgacc agaagctggg tctgaggatt accagcctca c ggagtgact    300
tccagaaata tcctgaccca caaggacgta acagaaaatc tggagaccca a gtggtagag    360
tccagactga gggagccacc tggagccaag gatgcaaatg gctcaacaag g acactgctt    420
gagaagatgg gagggaagcc aagacccagt gggcgcatcc ggtccgtgct g catgcagat    480
gagatgtgag ctggaacaga ccttcctggc ccacttcctg atcacaagga a tcctgggct    540
tccttatggc tttgcttccc actgggattc ctacttaggt gtctgccctc a ggggtccaa    600
atcacttcag gacaccccaa gagatgtcct ttagtctctg cctgaggcct a gtctgcatt    660
tgtttgcata tatgagaggg tacctgcccg ggcggccgct cga                        703
```

<210> SEQ ID NO 67
<211> LENGTH: 1022
<212> TYPE: DNA
<213> ORGANISM: Human

<400> SEQUENCE: 67

```
cttgagaaag caggattgtt ttaagttcca agatttaaca aacttactgt t cagcatcat     60
attcaagcct aaaaggaaga taggattttc aagatatatt tccaacttct t taacatggc    120
accatggatg aactgtttct cagcactgtg ctgcttcact tggaattaag g atgaattgg    180
gaggagacag tatgacatag gtgggtaggt tgggtggtga ggggaaccag t tctaatagt    240
cctcaactcc actccagctg ttcctgttcc acacggtcca ctgagctggc c cagtccctt    300
tcactcagtg tgtcaccaaa ggcagcttca aggctcaatg gcaagagacc a cctataacc    360
tcttcacctt ctgctgcctc tttctgctgc cactgactgc catggccatc t gctatagcc    420
gcattgtcct cagtgtgtcc aggccccaga caaggaaggg gagccatggt g agactccaa    480
ttcccaggcc ttaatcctta accctagacc tgttgcctct agcatcattt a tttatctac    540
ctacctaata gctatctacc agtcattaaa ccatggtgag attctaacca t gtctagcac    600
ctgatgctag agataatttt gttgaatccc ttcaattata aacagctgag t tagctggac    660
aaggactagg gaggcaatca gtattattta ttcttgaaca ccatcaagtc t agacttggt    720
ggcttcatat ttctatcata atccctgggg gtaagaaatc atatagcccc a ggttgggaa    780
ggggaaaacg gtttgcaaca ttctcctcct tgtaggaggc gagctctgtc t cactagcta    840
tgcccctcca tcaattcacc ctatactcag atcagaagct gagtgtctga a ttacagtat    900
attttctaaa ttcctagccc ctgctggtga atttgccctc ccccgctcct t tgacaattg    960
tccccgtgtt cgtctccggg ccctgagact ggccctgctt atcttgctga c cttcatcct   1020
ct                                                                   1022
```

<210> SEQ ID NO 68
<211> LENGTH: 449
<212> TYPE: DNA
<213> ORGANISM: Human

-continued

<400> SEQUENCE: 68

```
ccagatccat tttcagtggt ctggatttct ttttattttc ttttcaactt g aaagaaact     60

ggacattagg ccactatgtg ttgttactgc cactagtgtt caagtgcctc t tgttttccc    120

agagatttcc tgggtctgcc agaggcccag acaggctcac tcaagctctt t aactgaaaa    180

gcaacaagcc actccaggac aaggttcaaa atggttacaa cagcctctac c tgtcgcccc    240

agggagaaag gggtagtgat acaagtctca tagccagaga tggttttcca c tccttctag    300

atattcccaa aaagaggctg agacaggagg ttattttcaa ttttattttg g aattaaata    360

ctttttttccc tttattactg ttgtagtccc tcacttggat atacctctgt t ttcacgata    420

gaaataaggg aggtctagag cttctattc                                    449
```

<210> SEQ ID NO 69
<211> LENGTH: 387
<212> TYPE: DNA
<213> ORGANISM: Human
<220> FEATURE:
<221> NAME/KEY: modified_base
<222> LOCATION: (21)
<223> OTHER INFORMATION: Where n is a, c, g or t
<221> NAME/KEY: modified_base
<222> LOCATION: (26)
<223> OTHER INFORMATION: Where n is a, c, g or t
<221> NAME/KEY: modified_base
<222> LOCATION: (36)
<223> OTHER INFORMATION: Where n is a, c, g or t
<221> NAME/KEY: modified_base
<222> LOCATION: (45)
<223> OTHER INFORMATION: Where n is a, c, g or t
<221> NAME/KEY: modified_base
<222> LOCATION: (54)
<223> OTHER INFORMATION: Where n is a, c, g or t
<221> NAME/KEY: modified_base
<222> LOCATION: (56)
<223> OTHER INFORMATION: Where n is a, c, g or t
<221> NAME/KEY: modified_base
<222> LOCATION: (62)
<223> OTHER INFORMATION: Where n is a, c, g or t
<221> NAME/KEY: modified_base
<222> LOCATION: (63)
<223> OTHER INFORMATION: Where n is a, c, g or t
<221> NAME/KEY: modified_base
<222> LOCATION: (73)
<223> OTHER INFORMATION: Where n is a, c, g or t
<221> NAME/KEY: modified_base
<222> LOCATION: (92)
<223> OTHER INFORMATION: Where n is a, c, g or t
<221> NAME/KEY: modified_base
<222> LOCATION: (98)
<223> OTHER INFORMATION: Where n is a, c, g or t
<221> NAME/KEY: modified_base
<222> LOCATION: (105)
<223> OTHER INFORMATION: Where n is a, c, g or t
<221> NAME/KEY: modified_base
<222> LOCATION: (155)
<223> OTHER INFORMATION: Where n is a, c, g or t
<221> NAME/KEY: modified_base
<222> LOCATION: (174)
<223> OTHER INFORMATION: Where n is a, c, g or t
<221> NAME/KEY: modified_base
<222> LOCATION: (194)
<223> OTHER INFORMATION: Where n is a, c, g or t
<221> NAME/KEY: modified_base
<222> LOCATION: (302)
<223> OTHER INFORMATION: Where n is a, c, g or t
<221> NAME/KEY: modified_base
<222> LOCATION: (312)
<223> OTHER INFORMATION: Where n is a, c, g or t
<221> NAME/KEY: modified_base
<222> LOCATION: (358)
<223> OTHER INFORMATION: Where n is a, c, g or t
<221> NAME/KEY: modified_base -continued
<222> LOCATION: (375)
<223> OTHER INFORMATION: Where n is a, c, g or t
<221> NAME/KEY: modified_base
<222> LOCATION: (378)
<223> OTHER INFORMATION: Where n is a, c, g or t
<221> NAME/KEY: modified_base
<222> LOCATION: (381)
<223> OTHER INFORMATION: Where n is a, c, g or t

<400> SEQUENCE: 69
gcccttagcg tgggtcgcgg cncgangtct ggagcntatg tgatncctat g gtncncagg 60 cnnatactgc tantctcatt tattctcctg cnacctantc ctctnctctg g aatcacacc 120 attattgcct gttaacactg gactgtgagt accangcaat taatttgcac c aanaaagtt 180 gagggtatta tcanatattg caatctgtac agagggaaga tgatttcaat t tgatttcaa 240 cttaaccttc atctttgtct gttaacacta atagagggtg tctaataaaa t ggcaaattt 300 gngatctcat tnggtataac tacactcttt ttcacagatg tgatgactga a tttccanca 360 acctgcccgg gcggncgntc naagggc 387

<210> SEQ ID NO 70
<211> LENGTH: 836
<212> TYPE: DNA
<213> ORGANISM: Human

<400> SEQUENCE: 70
tattccattt acaaaataaa ttcagccctg cactttcttt agatgccttg a tttccagaa 60 tggagcttag tgctactgaa taccctggcc acagagccac ctcaggatat t cttttctcc 120 accctagttt atttatttat agatatctgt ttacaaagtc tgtagtaaat c ctgatgctg 180 accatctgaa atgtactttt tttctgaatg ctgtttcaat ctaaaatagc a gcttttgag 240 aaaacaatga tgtaaattcc ttatgataaa aggatgattc tatatattct t taatgatat 300 taaatatgcc gaagccaagc acacagtctt tctaaagtgt gtgtatgttt g tgtgaatgt 360 gaatgatact gatcttatat ctgttaaaag ttgttttaaa aagctgtggc a tcccattgt 420 tcatatttgc caagtcttct gtaaagatgt ctaggacgaa atattttatg t gctaatgca 480 tgtatttgta aaccagattt gtttaccact caaaattaac ttgttttctt c atccaaaaa 540 agtttatttc ttccacgtac ttaaattttc tgtgtgggta taatatagct t tctaatttt 600 tttctttcac aaaggcaggt tcaaaattct gttgaaagaa aaatgctttc t gaaactgag 660 gtataacacc agagcttgct gtttaaagga ttatatgatg tacatcagtt c tataaatgt 720 gctcagcagt ttaacatgtg aatcctgttt taaagtgctc agatttcaac t gtgtaagcc 780 attgatataa cgctgtaatt aaaaatgttt atatgaaaaa aaaaaaaaaa a aaaaa 836

<210> SEQ ID NO 71
<211> LENGTH: 618
<212> TYPE: DNA
<213> ORGANISM: Human

<400> SEQUENCE: 71
gttgcagtga gctcaagtgt tgggtgtatc agctcaaaac accatgtgat g ccaatcatc 60 tccacaggag caatttgttt acctttttttt tctgatgctt tactaacttc a tcttttaga 120 tttaaatcat tagtagatcc tagaggagcc agtttcagaa aatatagatt c tagttcagc 180 accacccgta gttgtgcatt gaaataatta tcattatgat tatgtatcag a gcttctggt 240 tttctcattc tttattcatt tattcaacaa ccacgtgaca aacactggaa t tacaggatg 300

-continued aagatgagat aatccgctcc ttggcagtgt tatactatta tataacctga a aaaacaaac 360 aggtaatttt cacacaaagt aatagatatc atgacacatt taaaataggg c actactgga 420 acacacagat aggacatcca ggttttgggt caatattgta gactttttgg t ggatgagat 480 atgcaggttg atrccagaag gacaacaaaa acatatgtca gatagaaggg a ggagcaaat 540 gccaagagct ggagctgagg aagatcactg tgaaattcta tgtagtctag t tggctggat 600 gctagagcaa agaggtgg 618

<210> SEQ ID NO 72
<211> LENGTH:
<212> TYPE:
<213> ORGANISM:

<400> SEQUENCE: 72

000

<210> SEQ ID NO 73
<211> LENGTH: 301
<212> TYPE: DNA
<213> ORGANISM: Human
<220> FEATURE:
<221> NAME/KEY: modified_base
<222> LOCATION: (59)
<223> OTHER INFORMATION: Where n is a, c, g or t

<400> SEQUENCE: 73
actctggtaa gcttgttgtt gtccaagtga agctccctca gatgaggcgt g ttggccana 60 gagccattgt caacagcaga gatgctgttg aaactcaatc ccaacttagc c aaattattc 120 agtcctttca ggctagctgc atcaactctg ctgattttgt tgccatcaag a tgtaattcc 180 gtaagggaag gaggaagacc ttgaggaatg ctggygatat tggyatcagc a atgcggatg 240 tasgaagagc ttcttcmttc cctggaaagc cccattttca atyccttgag c tcttcakcg 300 g 301

<210> SEQ ID NO 74
<211> LENGTH: 401
<212> TYPE: DNA
<213> ORGANISM: Human

<400> SEQUENCE: 74
agtttacatg atccctgtaa cagccatggt ctcaaactca gatgcttcct c catctgcca 60 agtgtgttct ggatacagag cacatcgtgg cttctggggt cacactcagc t taggctgtg 120 ggtccacaga gcactcatct ggctgggcta tggtggtggt ggctctactc a agaagcaaa 180 gcagttacca gcacattcaa acagtgtatt gaacatcttt taaatatcaa a gtgagaaac 240 aagaaggcaa cataataatg ttatcagaaa gatgttagga agtaaggaca g ctgtgtaaa 300 gcttgaggct gaaaagtagc ttgccagctt catttctttg gtttcttggg t agtgggccg 360 ccggaacagc aagatgtgag gttctggttc atggatcata t 401

<210> SEQ ID NO 75
<211> LENGTH: 612
<212> TYPE: DNA
<213> ORGANISM: Human

<400> SEQUENCE: 75
ttatttttca atttttattt tggttttctt acaaaggttg acattttcca t aacaggtgt 60 aagagtgttg aaaaaaaaat tcaaattttt ggggagcgag ggaaggagtt a atgaaactg 120

```
tattgcacaa tgctctgatc aatccttctt tttctctttt gcccacaatt t aagcaagta    180

gatgtgcaga agaaatggaa ggattcagct ttcagttaaa aaagaagaag a agaaatggc    240

aaagagaaag ttttttcaaa tttctttctt ttttaattta gattgagttc a tttatttga    300

aacagactgg gccaatgtcc acaaagaatt cctggtcagc accaccgatg t ccaaaggtg    360

caatatcaag gaagggcagg cgtgatggct tatttgtttt gtattcaatg a ttgtctttc    420

cccattcatt tgtcttttta gagcagccat ctacaagaac agtgtaagtg a acctgctgt    480

tgccctcagc aacaagttca acatcattag agccctgtag aatgacagcc t ttttcaggt    540

tgccagtctc ctcatccatg tatgcaatgc tgttcttgca gtggtaggtg a tgttctgag    600

aggcatagtt gg                                                        612
```

<210> SEQ ID NO 76
<211> LENGTH: 844
<212> TYPE: DNA
<213> ORGANISM: Human

<400> SEQUENCE: 76

```
ggctttcgag cggccgcccg ggcaggtctg atggttctcg taaaaacccc g ctagaaact     60

gcagagacct gaaattctgc catcctgaac tcaagagtgg agaatactgg g ttgacccta    120

accaaggatg caaattggat gctatcaagg tattctgtaa tatggaaact g gggaaacat    180

gcataagtgc caatcctttg aatgttccac ggaaacactg gtggacagat t ctagtgctg    240

agaagaaaca cgtttggttt ggagagtcca tggatggtgg ttttcagttt a gctacggca    300

atcctgaact tcctgaagat gtccttgatg tgcagcykgc attccttcga c ttctctcca    360

gccgagcttc ccagaacatc acatatcact gcaaaaatag cattgcatac a tggatcagg    420

ccagtggaaa tgtaaagaag gccctgaagc tgatggggtc aaatgaaggt g aattcaagg    480

ctgaaggaaa tagcaaattc acctacacag ttctggagga tggttgcacg a aacacactg    540

gggaatggag caaaacagtc tttgaatatc gaacacgcaa tgctgttcct t gacattgca    600

ccaccaatgt ccagaggtgc aatgtcaagg aacggcaggc gagatggctt a tttgttttg    660

tattcaatga ttgtcttgcc ccattcattt gtctttttgg agcagccatc g actaggaca    720

gagtaggtga acctgctgtt gccctcagca acaagttcca catcgttgga a ccctgcaga    780

agcacagcct tgttcaarct gcccgtctcc tcatccagat acctcggccg c gaccacgct    840

aatc                                                                 844
```

<210> SEQ ID NO 77
<211> LENGTH: 314
<212> TYPE: DNA
<213> ORGANISM: Human

<400> SEQUENCE: 77

```
ccagtcctcc acttggcctg atgagagtgg ggagtggcaa gggacgtttc t cctgcaata     60

gacacttaga tttctctctt gtgggaagaa accacctgtc catccactga c tcttctaca    120

ttgatgtgga aattgctgct gctaccacca cctcctgaag aggcttccct g atgccaatg    180

ccagccatcc tggcatcctg gccctcgagc aggctgcggt aagtagcgat c tcctgctcc    240

agccgtgtct ttatgtcaag cagcatcttg tactcctggt tctgagcctc c atctcgcat    300

cggagctcac tcag                                                      314
```

<210> SEQ ID NO 78

```
<211> LENGTH: 548
<212> TYPE: DNA
<213> ORGANISM: Human

<400> SEQUENCE: 78

accaagagcc aagtgttaca caggatattt taaaaataaa atgtttttgg a atcctcacc     60

tcccatgcta tcttctaaga taactacaaa tattcttcaa agatttaact g agttctgcc    120

aaggacctcc caggactcta tccagaatga ttattgtaaa gctttacaaa t cccaccttg    180

gccctagcga taattaggaa atcacaggca aacctcctct ctcggagacc a atgaccagg    240

ccaatcagtc tgcacattgg ttttgttaga tactttgtgg agaaaaacaa a ggctcgtga    300

tagtgcagct ctgtgcctac agagagcctc ccttttggtt ctgaaattgc t gatgtgaca    360

gagacaaagc tgctatgggt ctaaaacctt caataaagta actaatgaca c tcaaggtcc    420

tgggactctg agacagacgg tggtaaaacc cacagctgcg attcacattt c caatttatt    480

ttgagctctt tctgaagctg ttgcttccta cctgagaatt cccatttaga g agctgcaca    540

gcacagtc                                                            548


<210> SEQ ID NO 79
<211> LENGTH: 646
<212> TYPE: DNA
<213> ORGANISM: Human

<400> SEQUENCE: 79

accccgtcac tatgtgaata aaggcagcta gaaaatggac tcaattctgc a agccttcat     60

ggcaacagcc catattaaga cttctagaac aagttaaaaa aaatcttcca t ttccatcca    120

tgcatgggaa aagggcttta gtatagttta ggatggatgt gtgtataata a taaaatgat    180

aagatatgca tagtgggggga ataaagcctc agagtccttc cagtatgggg a atccattgt    240

atcttagaac cgagggattt gtttagattg ttgatctact aattttttttc t tcacttata    300

tttgaatttt caatgatagg acttattgga aattggggat aattctgttg t ggtattaaa    360

taatattcat tttttaaaaa ctcatcttgg tattgagtta gtgcattgac t tccaatgaa    420

ttgacataag cccatatttc attttaacca gaaacaaaaa ctagaaaatg t tactcccta    480

aataggcaac aatgtatttt ataagcactg cagagattta gtaaaaaaca t gtatagtta    540

ctttagaaac aacttctgac acttgagggt tacccaatgg tctccttccc a ttctttata    600

tgaggtaaat gcaaaccagg gagccaccga ataaacagcc ctgagt                  646


<210> SEQ ID NO 80
<211> LENGTH: 276
<212> TYPE: DNA
<213> ORGANISM: Human
<220> FEATURE:
<221> NAME/KEY: modified_base
<222> LOCATION: (16)
<223> OTHER INFORMATION: Where n is a, c, g or t
<221> NAME/KEY: modified_base
<222> LOCATION: (29)
<223> OTHER INFORMATION: Where n is a, c, g or t
<221> NAME/KEY: modified_base
<222> LOCATION: (32)
<223> OTHER INFORMATION: Where n is a, c, g or t
<221> NAME/KEY: modified_base
<222> LOCATION: (45)
<223> OTHER INFORMATION: Where n is a, c, g or t
<221> NAME/KEY: modified_base
<222> LOCATION: (53)
<223> OTHER INFORMATION: Where n is a, c, g or t
<221> NAME/KEY: modified_base
<222> LOCATION: (55)
```

<223> OTHER INFORMATION: Where n is a, c, g or t
<221> NAME/KEY: modified_base
<222> LOCATION: (58)
<223> OTHER INFORMATION: Where n is a, c, g or t
<221> NAME/KEY: modified_base
<222> LOCATION: (59)
<223> OTHER INFORMATION: Where n is a, c, g or t
<221> NAME/KEY: modified_base
<222> LOCATION: (65)
<223> OTHER INFORMATION: Where n is a, c, g or t
<221> NAME/KEY: modified_base
<222> LOCATION: (66)
<223> OTHER INFORMATION: Where n is a, c, g or t
<221> NAME/KEY: modified_base
<222> LOCATION: (75)
<223> OTHER INFORMATION: Where n is a, c, g or t
<221> NAME/KEY: modified_base
<222> LOCATION: (77)
<223> OTHER INFORMATION: Where n is a, c, g or t
<221> NAME/KEY: modified_base
<222> LOCATION: (85)
<223> OTHER INFORMATION: Where n is a, c, g or t
<221> NAME/KEY: modified_base
<222> LOCATION: (90)
<223> OTHER INFORMATION: Where n is a, c, g or t
<221> NAME/KEY: modified_base
<222> LOCATION: (97)
<223> OTHER INFORMATION: Where n is a, c, g or t
<221> NAME/KEY: modified_base
<222> LOCATION: (108)
<223> OTHER INFORMATION: Where n is a, c, g or t
<221> NAME/KEY: modified_base
<222> LOCATION: (112)
<223> OTHER INFORMATION: Where n is a, c, g or t
<221> NAME/KEY: modified_base
<222> LOCATION: (163)
<223> OTHER INFORMATION: Where n is a, c, g or t
<221> NAME/KEY: modified_base
<222> LOCATION: (170)
<223> OTHER INFORMATION: Where n is a, c, g or t

<400> SEQUENCE: 80
gtctgaatga gcttcnctgc gagatggganc ancataaccc agaantccaa a ancntanng 60 aacgnnaaaa cccgntngaa caagnaaacn gcaactnacg gccgcctgnt g nagggcgag 120 gacgcccacc tctcctcctc ccagttctcc tctggatcgc agncatccan a gatgtgacc 180 tcttccagcc gccaaatccg caccaaggtc atggatgtgc acgatggcaa g gtgggtgtc 240 cacccacgaa caggtccttc gcaccaagaa ctgagg 276

<210> SEQ ID NO 81
<211> LENGTH: 647
<212> TYPE: DNA
<213> ORGANISM: Human

<400> SEQUENCE: 81
gtcctgcctt tcatcttttc tttaaaaaaa ataaatgttt acaaaacatt t ccctcagat 60 tttaaaattc atggaagtaa taaacagtaa taaaatatgg atactatgaa a actgacaca 120 cagaaaaaca taaccataaa atattgttcc aggatacaga tattaattaa g agtgacttc 180 gttagcaaca cgtagacatt catacatatc cggtggaaga ctggtttctg a gatgcgatt 240 gccatccaaa cgcaaatgct tgatcttgga gtaggrtaat ggccccagga t cttgcagaa 300 gctctttatg tcaaacttct caagttgatt gacctccagg taatagtttt c aaggttttc 360 attgacagtt ggtatgtttt taagcttgtt ataggacaga tccagctcaa c cagggatga 420 cacattgaaa gaatttccag gtattccact atcagccagt tcgttgtgag a taaacgcag 480 atactgcaat gcattaaaac gcttgaaata ctcatcaggg atgttgctga t cttattgtt 540

-continued

```
gtctaagtag agagttagaa gagagacagg gagaccagaa ggcagtctgg c tatctgatt    600

gaagctcaag tcaaggtatt cgagtgattt aagaccttta aaagcag                  647
```

<210> SEQ ID NO 82
<211> LENGTH: 878
<212> TYPE: DNA
<213> ORGANISM: Human

<400> SEQUENCE: 82

```
ccttctttcc ccactcaatt cttcctgccc tgttattaat taagatatct t cagcttgta     60

gtcagacaca atcagaatya cagaaaaatc ctgcctaagg caaagaaata t aagacaaga    120

ctatgatatc aatgaatgtg ggttaagtaa tagatttcca gctaaattgg t ctaaaaaag    180

aatattaagt gtggacagac ctatttcaaa ggagcttaat tgatctcact t gttttagtt    240

ctgatccagg gagatcaccc ctctaattat ttctgaactt ggttaataaa a gtttataag    300

atttttatga agcagccact gtatgatatt ttaagcaaat atgttattta a aatattgat    360

ccttcccttg gaccaccttc atgttagttg ggtattataa ataagagata c aaccatgaa    420

tatattatgt ttatacaaaa tcaatctgaa cacaattcat aaagatttct c ttttatacc    480

ttcctcactg gccccctcca cctgcccata gtcaccaaat tctgttttaa a tcaatgacc    540

taagatcaac aatgaagtat tttataaatg tatttatgct gctagactgt g ggtcaaatg    600

tttccatttt caaattattt agaattctta tgagtttaaa atttgtaaat t tctaaatcc    660

aatcatgtaa aatgaaactg ttgctccatt ggagtagtct cccacctaaa t atcaagatg    720

gctatatgct aaaaagagaa aatatggtca agtctaaaat ggctaattgt c ctatgatgc    780

tattatcata gactaatgac atttatcttc aaaacaccaa attgtcttta g aaaaattaa    840

tgtgattaca ggtagagaac ctcggccgcg accacgct                            878
```

<210> SEQ ID NO 83
<211> LENGTH: 645
<212> TYPE: DNA
<213> ORGANISM: Human

<400> SEQUENCE: 83

```
acaaacattt tacaaaaaag aacattacca atatcagtgg cagtaagggc a agctgaaga     60

ataaatagac tgagtttccg ggcaatgtct gtcctcaaag acatccaaac t gcgttcagg    120

cagctgaaac aggcttcttt cccagtgaca agcatatgtg gtcagtaata c aaacgatgg    180

taaatgaggc tactacatag gcccagttaa caaactcctc ttctcctcgg g taggccatg    240

atacaagtgg aactcatcaa ataatttaaa cccaaggcga taacaacgct a tttcccatc    300

taaactcatt taagccttca caatgtcgca atggattcag ttacttgcaa a cgatcccgg    360

gttgtcatac agatacttgt ttttacacat aacgctgtgc catcccttcc t tcactgccc    420

cagtcaggtt tcctgttgtt ggaccgaaag gggatacatt ttagaaatgc t tccctcaag    480

acagaagtga gaaagaaagg agaccctgag gccaggatct attaaacctg g tgtgtgcgc    540

aaaagggagg gggaaggcag gaatttgaaa ggataaacgt ctcctttgcg c cgaggaatc    600

aggaagcgtg actcacttgg gtctgggacg ataccgaaat ccggt                    645
```

<210> SEQ ID NO 84
<211> LENGTH: 301
<212> TYPE: DNA
<213> ORGANISM: Human
<220> FEATURE:
<221> NAME/KEY: modified_base -continued
<222> LOCATION: (270)
<223> OTHER INFORMATION: Where n is a, c, g or t
<221> NAME/KEY: modified_base
<222> LOCATION: (284)
<223> OTHER INFORMATION: Where n is a, c, g or t

<400> SEQUENCE: 84
tctgatgtca atcacaactt gaaggatgcc aatgatgtac caatccaatg t gaaatctct 60 cctcttatct cctatgctgg agaaggatta gaaggttatg tggcagataa a gaattccat 120 gcacctctaa tcatcgatga gaatggagtt catgggctgg tgaaaaatgg t atttgaacc 180 agataccaag ttttgtttgc cacgatagga atagctttta tttttgatag a ccaactgtg 240 aacctacaag acgtcttgga caactgaagn ttaaatatcc acangggttt a ttttgcttg 300 g 301

<210> SEQ ID NO 85
<211> LENGTH: 296
<212> TYPE: DNA
<213> ORGANISM: Human
<220> FEATURE:
<221> NAME/KEY: modified_base
<222> LOCATION: (16)
<223> OTHER INFORMATION: Where n is a, c, g or t
<221> NAME/KEY: modified_base
<222> LOCATION: (20)
<223> OTHER INFORMATION: Where n is a, c, g or t
<221> NAME/KEY: modified_base
<222> LOCATION: (24)
<223> OTHER INFORMATION: Where n is a, c, g or t

<400> SEQUENCE: 85
agcgtgggtc gcggcncgan gtagagaacc gactgaaacg tttgagatga a gaaagttct 60 cctcctgatc acagccatct tggcagtggc tgttggtttc ccagtctctc a agaccagga 120 acgagaaaaa agaagtatca gtgacagcga tgaattagct tcagggtttt t tgtgttccc 180 ttacccatat ccatttcgcc cacttccacc aattccattt ccaagatttc c atggtttan 240 acgtaatttt cctattccaa tacctgaatc tgcccctaca actccccttc c tagcg 296

<210> SEQ ID NO 86
<211> LENGTH: 806
<212> TYPE: DNA
<213> ORGANISM: Human

<400> SEQUENCE: 86
tctacgatgg ccatttgctc attgtctttc ctctgtgtgt agtgagtgac c ctggcagtg 60 tttgcctgct cagagtggcc cctcagaaca acagggctgg ccttggaaaa a ccccaaaac 120 aggactgtgg tgacaactct ggtcaggtgt gatttgacat gagggccgga g gcggttgct 180 gacggcagga ctggagaggc tgcgtgcccg gcactggcag cgaggctcgt g tgtcccca 240 ggcagatctg ggcactttcc caacccaggt ttatgccgtc tccagggaag c ctcggtgcc 300 agagtggtgg gcagatctga ccatccccac agaccagaaa caaggaattt c tgggattac 360 ccagtccccc ttcaacccag ttgatgtaac cacctcattt tttacaaata c agaatctat 420 tctactcagg ctatgggcct cgtcctcact cagttattgc gagtgttgct g tccgcatgc 480 tccgggcccc acgtggctcc tgtgctctag atcatggtga ctcccccgcc c tgtggttgg 540 aatcgatgcc acggattgca ggccaaattt cagatcgtgt ttccaaacac c cttgctgtg 600 ccctttaatg ggattgaaag cacttttacc acatggagaa atatattttt a atttgtgat 660 gcttttctac aaggtccact atttctgagt ttaatgtgtt tccaacactt a aggagactc 720

-continued

```
taatgaaagc tgatgaattt tcttttctgt ccaaacaagt aaaataaaaa t aaaagtcta    780

tttagatgtt gaaaaaaaaa aaaaaa                                         806


<210> SEQ ID NO 87
<211> LENGTH: 620
<212> TYPE: DNA
<213> ORGANISM: Human

<400> SEQUENCE: 87

tttttgcatc agatctgaaa tgtctgagag taatagtttc tgttgaattt t tttttgttc     60

atttttctgc acagtccatt ctgtttttat tactatctag gcttgaaata t atagtttga    120

aattatgaca tccttcctct ttgttatttt cctcatgatt gctttggcta t tcaaagttt    180

attttagttt catgtaaatt tttgaattgt attttccatt attgtgaaaa t agtaccact    240

gcaattttaa taggaagttt attgaatcta tagattactt tggataatat g gcacttcaa    300

taatattcat gttttcaatt catagacaaa atattttaaa atttatttgt a tcttttcta    360

atttttcctt tttttattgt aaagatttac ctccttggtt aatattttcc t cagaaattt    420

attatttaag gtatagtcaa taaaattttc ttcctctatt ttgtcagata g tttaagtgt    480

atgaaaccat agatatactt gtatgttaat tttatatttt gctaatttac t gagtgtatt    540

tattagttta gagaggtttt aatgtactgt ttatggtttt ttaaatataa g attacttat    600

tttttaaaaa aaaaaaaaaa                                                620


<210> SEQ ID NO 88
<211> LENGTH: 308
<212> TYPE: DNA
<213> ORGANISM: Human
<220> FEATURE:
<221> NAME/KEY: modified_base
<222> LOCATION: (9)
<223> OTHER INFORMATION: Where n is a, c, g or t
<221> NAME/KEY: modified_base
<222> LOCATION: (189)
<223> OTHER INFORMATION: Where n is a, c, g or t
<221> NAME/KEY: modified_base
<222> LOCATION: (194)
<223> OTHER INFORMATION: Where n is a, c, g or t
<221> NAME/KEY: modified_base
<222> LOCATION: (206)
<223> OTHER INFORMATION: Where n is a, c, g or t
<221> NAME/KEY: modified_base
<222> LOCATION: (238)
<223> OTHER INFORMATION: Where n is a, c, g or t
<221> NAME/KEY: modified_base
<222> LOCATION: (296)
<223> OTHER INFORMATION: Where n is a, c, g or t

<400> SEQUENCE: 88

tagctgtgnt cagcaggccg aggttttttt ttttttttgag atggagtctc g ccctgtcac     60

ccaggctgga gtgcagtggc ctgatctcag ctcactgcaa gctccacctc c tggattcac    120

gctattctcc tgcctcagcc tcccaagtag ctgggactac aggcgcccgc c accacgccc    180

agctaattnt ttgnattttt agtacnagat gcggtttcat cgtgttagcc a gcatggnct    240

cgatctcctg acctcgtgaa ctgcccgcct cggcctccca aagacctgcc c gggcnggcc    300

gctcgaaa                                                             308


<210> SEQ ID NO 89
<211> LENGTH: 492
<212> TYPE: DNA
<213> ORGANISM: Human
```

<220> FEATURE:
<221> NAME/KEY: modified_base
<222> LOCATION: (448)
<223> OTHER INFORMATION: Where n is a, c, g or t

<400> SEQUENCE: 89

```
agcggccgcc cgggcaggtc tgttaagtaa catacatatc accttaataa a aatcaagat     60

gaaatgtttt agaaactatt ttatcaaaag tggctctgat acaaagactt g tacatgatt    120

gttcacagca gcactattaa tgccaaaaag tagacaaaac ctaaatgtcc a ttaactgat    180

aagcaaaatg tggtatatcc atacaatgga atattatgta gcccacaaca t ggcatggag    240

tactacaaca tggatgagcc tcaaaaacgt tatgctaaat gaaaaaagtc a gatatagga    300

aaccacatgt catatgatcc catttatatg aaatagccag aaaaggcaag t catagaaac    360

aagatagatc ggaaaatggg ttggaggact acaaatggca ccagggatct t tgaagttga    420

tggaaatggt ctaaaatcag actgtggntg tggttgaaca agtctgtaaa t ttaccaaaa    480

tgcgttaata ca                                                        492
```

<210> SEQ ID NO 90
<211> LENGTH: 390
<212> TYPE: DNA
<213> ORGANISM: Human
<220> FEATURE:
<221> NAME/KEY: modified_base
<222> LOCATION: (106)
<223> OTHER INFORMATION: Where n is a, c, g or t
<221> NAME/KEY: modified_base
<222> LOCATION: (184)
<223> OTHER INFORMATION: Where n is a, c, g or t
<221> NAME/KEY: modified_base
<222> LOCATION: (206)
<223> OTHER INFORMATION: Where n is a, c, g or t
<221> NAME/KEY: modified_base
<222> LOCATION: (209)
<223> OTHER INFORMATION: Where n is a, c, g or t
<221> NAME/KEY: modified_base
<222> LOCATION: (234)
<223> OTHER INFORMATION: Where n is a, c, g or t
<221> NAME/KEY: modified_base
<222> LOCATION: (314)
<223> OTHER INFORMATION: Where n is a, c, g or t

<400> SEQUENCE: 90

```
tcgagcggcc gcccgggcag gtacaagctt tttttttttt tttttttttt t tttctaaca     60

gttctctgtt ttattgcaat acagcaaagt ctggttaata ttaagngata t caacataaa    120

gtattggtga ggagtctttt gtgacatttt ttaccatccc accttaaata t ttctgtgca    180

aaanaatcca catcattgtt tggtancana ggatctctta aaaagttccc t aanacactg    240

agggcataaa accaaacaaa ataaaataag gagtgatagg ctaaagcagt a tcttcccct    300

ccatccacat ttgncaagca ttatattcta accaaaaaat gatcacacca g gccatgcaa    360

aactgtccaa tattaccgag aaaaaaccct                                     390
```

<210> SEQ ID NO 91
<211> LENGTH: 192
<212> TYPE: DNA
<213> ORGANISM: Human

<400> SEQUENCE: 91

```
agcgtggtcg cggccgaggt ctgtcaatta atgctagtcc tcaggattta a aaaataatc     60

ttaactcaaa gtccaatgca aaaacattaa gttggtaatt actcttgatc t tgaattact    120

tccgttacga aagtccttca catttttcaa actaagctac tatatttaag g cctgcccgg    180
```

gcggccgctc ga 192

<210> SEQ ID NO 92
<211> LENGTH: 570
<212> TYPE: DNA
<213> ORGANISM: Human
<220> FEATURE:
<221> NAME/KEY: modified_base
<222> LOCATION: (519)
<223> OTHER INFORMATION: Where n is a, c, g or t
<221> NAME/KEY: modified_base
<222> LOCATION: (559)
<223> OTHER INFORMATION: Where n is a, c, g or t

<400> SEQUENCE: 92
agcgtggtcg cggccgaggt ctgacaacta acaaagaagc aaaaactggc a tcttggaca 60 tcctagtatt acacttgcaa gcaattagaa cacaaggagg gccaaggaaa a agtttagct 120 ttgaatcact tccaaatcta ctgattttga ggttccgcag tagttctaac a aaacttttc 180 agacaatgtt aactttcgat taagaaagaa aaaaacccca aacatcttca g gaattccat 240 gccaggttca gtctcttcca gtgagcccgc ttgctaaaag tccacgtgca c cattaatta 300 gctgggctgg cagcaccatg taaaaagaag cctattcacc accaaccaca c agactagac 360 atgtaaagta ggatcaagta atggatgaca accatggtcg tggaatatgg t caatgagag 420 tcagaaaagt acaggcacca gtacaagcag cagataacag aattgacggg c caaaggata 480 aaaataggct tatttaaata ggatgctaca gaacacatnc acttctaatt g gaagctgct 540 ttacactggg tggcattgna ccatatgcat 570

<210> SEQ ID NO 93
<211> LENGTH: 446
<212> TYPE: DNA
<213> ORGANISM: Human
<220> FEATURE:
<221> NAME/KEY: modified_base
<222> LOCATION: (328)
<223> OTHER INFORMATION: Where n is a, c, g or t
<221> NAME/KEY: modified_base
<222> LOCATION: (389)
<223> OTHER INFORMATION: Where n is a, c, g or t

<400> SEQUENCE: 93
tcgagcggcc gcccgggcag gtccaggttt ttatttagtt gtgtaatctt g gacaagtta 60 cctaactttt ttgagtctga atatatttaa tctgcaaaat gagaatcatg a taatacgtc 120 ataggcttaa ttaggaggat taaatgaaat aatttatagg tggtgccatg g ttacataca 180 agtattagta gttaattctt ttcctttgtt tacttttata gtataggttg g atgaaggtt 240 ccagtatagg caaaaatact acttgggggt aaagtagagt gtgatacttt a tttgaaatg 300 ttccctgaat ctgatcttta ctttttgnta ctgctgcact acccaaatcc a aattttcat 360 cccaacattc ttggatttgt gggacagcng tagcagcttt tccaatataa t ctatactac 420 atcttttctt actttggtgc tttttg 446

<210> SEQ ID NO 94
<211> LENGTH: 409
<212> TYPE: DNA
<213> ORGANISM: Human

<400> SEQUENCE: 94
cgagcggccg cccgggcagg tccatcagct cttctgctta gaatacgagg c agacagtgg 60

-continued

```
agaggtcaca tcagttatcg tctatcaggg tgatgaccca agaaaggtga g tgagaaggt    120

gtcggcacac acgcctctgg atccacccat gcgagaagcc ctcaagttgc g tatccagga    180

ggagattgca aagcgccaga gccaacactg accatgttga aggcgttctc t ccaggctgg    240

attcactgca ctcggaagaa ttctgcccag ggaatttagt gtgggggtac c aggaccagt    300

ttgtcttgat cttgagaccc ccagagctgc tgcatccata gggtgttgca g gactacacc    360

tggcctgcct tgcagtcatt ctttcttata tgttgaccca tttgcccaa                409
```

<210> SEQ ID NO 95
<211> LENGTH: 490
<212> TYPE: DNA
<213> ORGANISM: Human
<220> FEATURE:
<221> NAME/KEY: modified_base
<222> LOCATION: (486)
<223> OTHER INFORMATION: Where n is a, c, g or t

<400> SEQUENCE: 95

```
tcgagcggcc gcccgggcag gtcctacttg tttgcagctt ccacacactg c acctaccta     60

ctacctctct tccatgctta actgggttta gaaaggtgag ctatgcgtag a agaactact    120

tgggatattc aagtgctgta tttgaacgat aagcctatag ataacagtct g aagctgcaa    180

gggagacttt gttagtacac tactataaac aggtaaacta cctgtttgta c ttgatatag    240

tgcatatgaa atgactgatt taatacaaaa ctacagaaca tgcaaaattt t ttctgagat    300

gttaagtatt acttcagtgg agaacaaaac ttacttaacc tttcgctaat g catgtagta    360

ccagaaagca aacatggttt tagcttcctt tactcaaaat atgaacatta a gtggttgtg    420

aattttgtct gccaagtggt tcagaaaata cattataaat aacctaagtt a aaaaaaaga    480

aactgngaac                                                           490
```

<210> SEQ ID NO 96
<211> LENGTH: 223
<212> TYPE: DNA
<213> ORGANISM: Human

<400> SEQUENCE: 96

```
agcgtggtcg cggccgaggt ctggaagccc accctaggac ttgaatggca c cttgtcctt     60

tctctgccag taatgcaatc caacacaata tgctacaggg aaaacagaat t tccacggtg    120

ccgccctctg gtacaaggga aacagcacgc aaagcaaaag gccacagagg g ctccctgag    180

aatccagtac aactaagcga ggacctgccc gggcggccgc tcg                      223
```

<210> SEQ ID NO 97
<211> LENGTH: 527
<212> TYPE: DNA
<213> ORGANISM: Human
<220> FEATURE:
<221> NAME/KEY: modified_base
<222> LOCATION: (404)
<223> OTHER INFORMATION: Where n is a, c, g or t
<221> NAME/KEY: modified_base
<222> LOCATION: (436)
<223> OTHER INFORMATION: Where n is a, c, g or t
<221> NAME/KEY: modified_base
<222> LOCATION: (451)
<223> OTHER INFORMATION: Where n is a, c, g or t
<221> NAME/KEY: modified_base
<222> LOCATION: (476)
<223> OTHER INFORMATION: Where n is a, c, g or t

<400> SEQUENCE: 97

-continued

```
tcgagcggcc gcccgggcag gtctgtgcag gagacactga agtgggtagt g tccataatc     60

tttttagcct gttgctgaaa ttccagttgt actccttcaa accaaaatgc t tacaggatc    120

atgggaaagc ctcggttgca gaaatcaaga caggcaagtg ggaagataac t cggctttga    180

ggttaaacag atctgggttc aaagcatagt ttcactctct gtcttgtgaa g tgtcctggg    240

tgaagtcatt tcctctcttg aatttcagag aggatgaaaa tataaaaagt a taataacta    300

tcttcataat ctttgtgagg attaaagaag acgaagtgtg tgaaaagcta a gcacagagc    360

aggcattcta caataagtag ttattatttt tggaaccatc ccgnccctag c cccagccca    420

attaccttct cttagnctct tcatatcgaa ngccgtaatc ttgaccttct c ttgcnactg    480

gattggtgct ggttgatgcc caaacttccc gagatgctgt ctgggaa                 527
```

<210> SEQ ID NO 98
<211> LENGTH: 514
<212> TYPE: DNA
<213> ORGANISM: Human
<220> FEATURE:
<221> NAME/KEY: modified_base
<222> LOCATION: (455)
<223> OTHER INFORMATION: Where n is a, c, g or t

<400> SEQUENCE: 98

```
tcgagcggcc gcccgggcag gtctggctcc catggccctt ggggtggcct g actctgtca     60

ctattcctaa aaccttctag gacatctgct ccaggaagaa ctttcaacac c aaaattcat    120

ctcaatttta cagatgggaa aagtgattct gagaccagac cagggtcagg c caaggtcat    180

ccagcatcag tggctgggct gagactgggc ccagggaacc ctgtctgctc c tctttttcc    240

cagagctgtg agttctctag ccaaggctgc actcttgagg gagagccagg a agcatagct    300

gaggccatga caacctcact cttcacctga aaatttaacc cgtggcagag g atccaggca    360

catataggct tcggagccaa acaggacctc ggccgcgacc acgctaagcc g aattccagc    420

acactggcgg ccgttactag tggatcccga gcttnggtac caagcttggc g taatcatgg    480

gcatagctgg ttcctggggt gaaaatggta tccg                               514
```

<210> SEQ ID NO 99
<211> LENGTH: 530
<212> TYPE: DNA
<213> ORGANISM: Human
<220> FEATURE:
<221> NAME/KEY: modified_base
<222> LOCATION: (430)
<223> OTHER INFORMATION: Where n is a, c, g or t
<221> NAME/KEY: modified_base
<222> LOCATION: (522)
<223> OTHER INFORMATION: Where n is a, c, g or t

<400> SEQUENCE: 99

```
tcgagcggcc gcccgggcag gtctgaagaa acaggtataa atttggcagc c agtaatttt     60

gacagggaag ttacagcttg catgacttta aatatgtaaa tttgaaaata c tgaatttcg    120

agtaatcatt gtgctttgtg ttgatctgaa aaatataaca ctggctgtcg a agaagcatg    180

ttcaaaaata tttaattcac ttcaaaatgt catacaaatt atggtggttt c tatgcaccc    240

ctaaagcttc aagtcattta gctcaggtac atactaaagt aatatattaa t tcttccagt    300

acagtggtgt ttcataccat tgacatttgc ataccctaga ataatttaag a aagacatgt    360

gtaatattca caatgttcag aaaagcaagc aaaaggtcaa ggaacctgct t tggttcttc    420

tggagatggn ctcatatcag cttcataaac attcattcta caaaatagta a gctaaccat    480
```

-continued

```
ttgaacccca atttccagat taagcatatt ttctcataaa tnatgaagcc           530


<210> SEQ ID NO 100
<211> LENGTH: 529
<212> TYPE: DNA
<213> ORGANISM: Human

<400> SEQUENCE: 100

agcgtggtcg cggccgaggt ccaggcacgg tggcttatgt gtgtaatccc a gcacttggg    60

gaggctgagg gaggtggatc acttgagtcc aggagtttga gaccagtctg g gcaacatgg   120

cgaaacttca tcactaccaa agaagaaaaa aattagccag gtgtggtggt g tatgcctgt   180

agtcccagat actctggtgg ctgaggtgag aggatagctt gagcccagga a attgaggct   240

gcagtgaact atgattgcac tactgtgctc cagcttgggc aacagagtga g atcttgtct   300

ccaaaagtcc ttgaaggatt ttaggaagtt gttaaaagtc ttgaaacgat g tttgggggc   360

atgttagggt tcttgaatgt ttaattcctc taataactgc ttattcaaga g aagcatttc   420

tgactgggtg cggggcagtg gcttcatgcc ccataatccc agtactttgg g aggctgaag   480

caggaacatt gcttgagccc aggacttcaa gaacagcctg ggtaacata            529


<210> SEQ ID NO 101
<211> LENGTH: 277
<212> TYPE: DNA
<213> ORGANISM: Human

<400> SEQUENCE: 101

tcgagcggcc gcccgggcag gtcgcaggaa gaggatggaa actgaggagt c caggaagaa    60

gagggaacga gatcttgagc tggaaatggg agatgattat attttggatc t tcagaagta   120

ctgggattta atgaatttgt ctgaaaaaca tgataagata ccagaaatct g ggaaggcca   180

taatatagct gattatattg atccagccat catgaagaaa ttggaagaat t agaaaaaga   240

agaagagctg agaacagacc tcggccgcga ccacgct                         277


<210> SEQ ID NO 102
<211> LENGTH: 490
<212> TYPE: DNA
<213> ORGANISM: Human

<400> SEQUENCE: 102

gcgtggtcgc ggccgaggtc tgacggcttt gctgtcccag agccgcctaa a cgcaagaaa    60

agtcgatggg acagttagag gggatgtgct aaagcgtgaa atcagttgtc c ttaattttt   120

agaaagattt tggtaactag gtgtctcagg gctgggttgg ggtccaaagt g taaggaccc   180

cctgccctta gtggagagct ggagcttgga gacattaccc cttcatcaga a ggaattttc   240

ggatgttttc ttgggaagct gttttggtcc ttggaagcag tgagagctgg g aagcttctt   300

ttggctctag gtgagttgtc atgtgggtaa gttgaggtta tcttgggata a agggtcttc   360

tagggcacaa aactcactct aggtttatat tgtatgtagc ttatattttt t actaaggtg   420

tcaccttata agcatctata aattgacttc tttttcttag ttgtatgacc t gccccgggc   480

ggccgctcga                                                       490


<210> SEQ ID NO 103
<211> LENGTH: 490
<212> TYPE: DNA
<213> ORGANISM: Human

<400> SEQUENCE: 103
```

```
gagcggccgc ccgggcaggt ccaaaccagc ttgctcataa gtcattaacc a aatccatta    60

taggtaattt gttcagttca atgtttacaa ttcttatgga aaaaattagc a acacacaca   120

tttaaaacgt gtgcatttac ctttgcgtga gtgcttaaaa tacatatttc t atttcaaga   180

tgacatttaa aaattattct aatatatcag cagcaaaaat ataatttgca a ttacaaaaa   240

actaaactag aatccttaag ttattctcat gtttacagtt gtgattcttt a ataaatact   300

attatgcagc tctattgttt aagctttctg gatttggttt aaacacatgc a tatatattg   360

tcaattgtgg gaagctttac aagttatatt ccatgcactt tttggacaga g ttctaacag   420

agccagccag tccacaaaac aggcaagaca aaagttgaat taactggggc a aaataggac   480

tcttatgcaa                                                          490
```

<210> SEQ ID NO 104
<211> LENGTH: 489
<212> TYPE: DNA
<213> ORGANISM: Human

<400> SEQUENCE: 104

```
cgtggtcgcg gccgaggtcc aggctggtct cgaactcctg accttgtgat c tgcccgcct    60

cggcctccca aagtgttggg attacaggca tgagccactg cgcccgaccg a gttgaacat   120

ttaatgtcag actaggccag agtttctcaa tctttttatt ctcacttccc a aaggagccg   180

ttggagattt tcccctcaat ctctctcctt catgaaattt cataccacaa a tatagtatg   240

ttttatttat gtactgtgac cctttgaagg atcacaaacc aatataatag t ttttctttt   300

taacccgtca aggaccaagt tttgcccct gttggaaatg cataaactgg a ctgatgaat   360

tggtatagat ggcttttatc atgaggatca gaaaaacttg aaattccttg g ctacgacac   420

tccatattta tcaccgtata gggaggacct tggtatgggg aagtagaaac a cttctacac   480

tttacagca                                                           489
```

<210> SEQ ID NO 105
<211> LENGTH: 479
<212> TYPE: DNA
<213> ORGANISM: Human
<220> FEATURE:
<221> NAME/KEY: modified_base
<222> LOCATION: (142)
<223> OTHER INFORMATION: Where n is a, c, g or t
<221> NAME/KEY: modified_base
<222> LOCATION: (453)
<223> OTHER INFORMATION: Where n is a, c, g or t

<400> SEQUENCE: 105

```
gcgtggtcgc ggccgaggtc tgactggctt cagccccaga agttgagctg g cctttagac    60

aaaataattg cacctccctc tgctgcttat tcccttccgt ttttcatttg a gtgtgaaca   120

gttagataaa atctgtggct gnctcttcca ccttgctcta gtttccattg c tgtgagcag   180

gccctcctat gccccgcatt tagctacaat gctgtggact cacttgattc t ttttctccg   240

agctttgtct agaaatatgt gaaggtgagg ttaagtgctt ctctgtgtag a tccacttag   300

ccctgtctgc tgtctcgatg ggcgttgctt cgtctctcct ctcttccatc c tttccattt   360

gcttctcacc accttctggc ttcttttctt aatgcaataa aggcagtttc t aacaaagaa   420

agaatgtggg ctttggagtt agacagacct ggntttaaat tctgcttctg g ctctccaa    479
```

<210> SEQ ID NO 106
<211> LENGTH: 511

-continued

<212> TYPE: DNA
<213> ORGANISM: Human

<400> SEQUENCE: 106

```
tcgcggccga ggtccaaaac gtggattcca atgacctgcc ttgagcccgc g gttgccagg     60

agttggacct gcagtagtat gggaagctca cggcctaaat accgactgcc c tctgacccc    120

accgtccagc gattctagaa catttctagt aggaaagaca tagcaaggga t tttcatgat    180

tgggaaatac tgggagacaa gctgaagatt tgttaagggc tatgcttctg t catctttta    240

ggtatttaag gctactcctt tagctagcta ctttgagctg tttaaagtga c tatctccct    300

acacagagtt acacaatgag catctctgaa agagaatatt accctggatt t ccaaagatg    360

tactctaaca ggatgaccag gcaaaaggtg acccggggga ggagtctgtt a taacactcg    420

gacccacatg ttctcaaggc acttcagaac tttgggaaat cattttgtac c ggatcctca    480

gaaagcattt atggaaatac acatccttta g                                   511
```

<210> SEQ ID NO 107
<211> LENGTH: 451
<212> TYPE: DNA
<213> ORGANISM: Human

<400> SEQUENCE: 107

```
ggccgcccgg gcaggtccag aatatcaaat caaaaggtca caaatgttca c ttcctcctc     60

caccctctta catattggat cttcaattgc aatagggagt gtaagatggg c attttagag    120

acgtagttgc atcagcagaa gcaaacccat cttatacaaa tgggttttgg g gataggaaa    180

aggctgctaa aaattcacaa gtcaccattc cccagaagca atgaatagcc g tagaagacc    240

aaggaagatc aacaagtttc caaagtgcta aagccagaga tttggccctt c caaaatacc    300

accaggacgc ctggacccgt gggctctccg catgtcacca ctgactgcca g gatgctgct    360

gcacctccct tccttgagac acaacagaga gacagtgaag tcacccaaga c tgggatcat    420

cagaggctcc tcatgcttgc tacagagaag c                                   451
```

<210> SEQ ID NO 108
<211> LENGTH: 461
<212> TYPE: DNA
<213> ORGANISM: Human

<400> SEQUENCE: 108

```
ccgcccgggc aggtcctgaa aacattcaga ctaatcaaaa tggtactact g taacttctt     60

ataatacata atataaaagt ttttgaaaga tatagacaca attaacccct a aacaacaca    120

ctatctgatt ctcaaaagca atggctattt aacaagatgt aaaaggacaa t aacatatca    180

aagaactttc acacacctaa agatagcatt tagcagcaag ttagtcagac a aaacaaaca    240

caaatatttt cacatttcct atgtttgttt ttaactttac ttcataaagc c actgataat    300

tgaggtttct ttcaagtata agatttctaa aattaaaaac tgtttttgac a tatttttat    360

aaagaaataa aaagcaaaac gcaatccaac tatttatatg agtccctctt c tccaacagc    420

tttagatggt tttctgagta ctttttaca cagaatattt t                          461
```

<210> SEQ ID NO 109
<211> LENGTH: 441
<212> TYPE: DNA
<213> ORGANISM: Human

<400> SEQUENCE: 109

-continued

```
ggccgcccgg gcaggtctga ttataagaga aagaaatcca gtgacacgag g gcaggcagg     60

ccccgctctg ctctgatcga gaaaagcttc ctgatgtcag ggagatggaa c tgccaccat    120

cagaaccatg gcactttggg tgaaggtgtg tcagcgacca agggggcagg a aatgggcag    180

tgactaaggg ggcaggaaac aggcaggcac atggcaaggt tctcccagcc c atcagccca    240

gtgatggcct cgattttgaa gctgcactac tgtctgaaaa gcacaattac t ggtgactct    300

taacaaactt cagcatactg ggaaggaga ctgtcaagta actgaattgg a aagatgaaa    360

aagaaccatc tctaaaagtt gatgcttgtc agaagaataa cctcctttgt g caagtcttg    420

caacatcttc attcaaccac a                                               441
```

<210> SEQ ID NO 110
<211> LENGTH: 451
<212> TYPE: DNA
<213> ORGANISM: Human
<220> FEATURE:
<221> NAME/KEY: modified_base
<222> LOCATION: (260)
<223> OTHER INFORMATION: Where n is a, c, g or t
<221> NAME/KEY: modified_base
<222> LOCATION: (361)
<223> OTHER INFORMATION: Where n is a, c, g or t

<400> SEQUENCE: 110

```
ggtcgcggcc gaggtctggg gaaggggtga gaatccctgg gccttgccca g tcctgagct     60

ctgggtgtct gcagggaagc acagtggtga gttagtgtta aagaaagcat c cagagaggt    120

aagaggggct tgggtagcac cctttgcctc tgtcacttcc gcaaaaactt c ttgttgagg    180

aggaagatga gaaggttgac attgactttg gccttgttga agagtttcat g acagccaca    240

ccctcatact ggagctgcan gagatcctga tagtgaagct tgaaatcgct c catgtccac    300

acccaggaac ttggcattta cttcaaactt tcctgcctca tctcccggcg t gatgtcaaa    360

natgacgttt cttgaagtga gaggcgggaa agatcttcaa tttccaccaa a gacaccctt    420

tttccaggaa gcttgagcaa caagtgtaat g                                    451
```

<210> SEQ ID NO 111
<211> LENGTH: 407
<212> TYPE: DNA
<213> ORGANISM: Human
<220> FEATURE:
<221> NAME/KEY: modified_base
<222> LOCATION: (26)
<223> OTHER INFORMATION: Where n is a, c, g or t
<221> NAME/KEY: modified_base
<222> LOCATION: (33)
<223> OTHER INFORMATION: Where n is a, c, g or t
<221> NAME/KEY: modified_base
<222> LOCATION: (36)
<223> OTHER INFORMATION: Where n is a, c, g or t
<221> NAME/KEY: modified_base
<222> LOCATION: (79)
<223> OTHER INFORMATION: Where n is a, c, g or t
<221> NAME/KEY: modified_base
<222> LOCATION: (105)
<223> OTHER INFORMATION: Where n is a, c, g or t
<221> NAME/KEY: modified_base
<222> LOCATION: (111)
<223> OTHER INFORMATION: Where n is a, c, g or t
<221> NAME/KEY: modified_base
<222> LOCATION: (133)
<223> OTHER INFORMATION: Where n is a, c, g or t
<221> NAME/KEY: modified_base
<222> LOCATION: (149)
<223> OTHER INFORMATION: Where n is a, c, g or t
<221> NAME/KEY: modified_base
<222> LOCATION: (186)

-continued

<223> OTHER INFORMATION: Where n is a, c, g or t
<221> NAME/KEY: modified_base
<222> LOCATION: (206)
<223> OTHER INFORMATION: Where n is a, c, g or t
<221> NAME/KEY: modified_base
<222> LOCATION: (220)
<223> OTHER INFORMATION: Where n is a, c, g or t
<221> NAME/KEY: modified_base
<222> LOCATION: (239)
<223> OTHER INFORMATION: Where n is a, c, g or t
<221> NAME/KEY: modified_base
<222> LOCATION: (245)
<223> OTHER INFORMATION: Where n is a, c, g or t
<221> NAME/KEY: modified_base
<222> LOCATION: (259)
<223> OTHER INFORMATION: Where n is a, c, g or t
<221> NAME/KEY: modified_base
<222> LOCATION: (336)
<223> OTHER INFORMATION: Where n is a, c, g or t
<221> NAME/KEY: modified_base
<222> LOCATION: (375)
<223> OTHER INFORMATION: Where n is a, c, g or t
<221> NAME/KEY: modified_base
<222> LOCATION: (383)
<223> OTHER INFORMATION: Where n is a, c, g or t
<221> NAME/KEY: modified_base
<222> LOCATION: (393)
<223> OTHER INFORMATION: Where n is a, c, g or t

<400> SEQUENCE: 111
ggccgacgtt cgacctgact tctttngagc agntgncact acccgtcttg a ggaatgccg 60 actgcagaca gtggcccang gcaaagagtg tgcgtcatcg atganattgg n aagatggag 120 ctcttcagtc agnttttcat tcaagctgnt cgtcagacgc tgtctacccc a gggactata 180 atcctnggca caatcccagt tcctanagga aagccactgn ctcttgtaga a gaaatcana 240 cacanaaagg atgtgaacng tgtttaatgt caccaaggga aaacatgaaa c caccttctg 300 ccagatatcg ggacgttgcg tgcagatcaa gcacgnaagt gaagacgcgt g cattccttg 360 ccttccgtga acgantgccc agntcaagaa gancctgatg gaaccct 407

<210> SEQ ID NO 112
<211> LENGTH: 401
<212> TYPE: DNA
<213> ORGANISM: Human
<220> FEATURE:
<221> NAME/KEY: modified_base
<222> LOCATION: (363)
<223> OTHER INFORMATION: Where n is a, c, g or t

<400> SEQUENCE: 112
tcgcggccga ggtcggccga ggtctgacat ctgttgtctg tgataaccac t tctgtattg 60 cgtcttaacc acttctgtat tgtgtggttt taactgccta aggcggcaat g ggcagtggg 120 cccctttccc ttaggatggg tatcaattca acaatattta taaggcattt a ctgtgtgct 180 aagcatttgg aagacccagg ctacaaaata agacatagtt cctgccctcc a ggccagcag 240 agggaggcac aaatacccag gaatctctga tgggtgtgaa gtgcggtcgt g ggccacaga 300 aaatgaccgt catggagacc ctgctaaagg tcggaccctg agcccaaagg g gtattcaga 360 agnggagatg attttggccc cactcataga tgggtggcaa a 401

<210> SEQ ID NO 113
<211> LENGTH: 451
<212> TYPE: DNA
<213> ORGANISM: Human

<400> SEQUENCE: 113

-continued

```
gtcgcggccg aggtccatat taaaaagtcc atcataaaca aagactcctc c tcatggtat     60

gaatatgctc catatgccca taatggtgca taacggactt agaaattcca a tgagtctta    120

gggttgaaat ttccaatgac ctgagcaagg cagctcccta tagcttctgg a taacatttt    180

acacccagag ttcaggctta aacagaccta tcaacacaat tattttcgga t tgtctgtct    240

agaaaacggc aatgctcaaa ggaatataaa taagggtggg gggacatatg c ttccagcct    300

ggcctttctc catgtggtaa aaaacaatgg aatggctgtg ttaatttttt t ttaatcttt    360

tctgaccttt actatgtttg gtaatggaaa taagtcaggg aaaacaaaat g aacaggtct    420

catcacttaa ttaatactgg gttttcttct t                                451
```

```
<210> SEQ ID NO 114
<211> LENGTH: 441
<212> TYPE: DNA
<213> ORGANISM: Human

<400> SEQUENCE: 114

ggccgcccgg gcaggtccat cctgtcagag atgggagaag tcacagacgg a atgatggat     60

acaaagatgg ttcactttct tacacactat gctgacaaga ttgaatctgt t catttttca    120

gaccagttct ctggtccaaa aattatgcaa gaggaaggtc agcctttaaa g ctacctgac    180

actaagagga cactgttgtt tacatttaat gtgcctggct caggtaacac t tacccaaag    240

gatatggagg cactgctacc cctgatgaac atggtgattt attctattga t aaagccaaa    300

aagttccgac tcaacagaga aggcaaacaa aaagcagata agaaccgtgc c cgagtagaa    360

gagaacttct tgaaacttga cacatgtgca aagacaggaa gcagcacagt c tcggcggga    420

ggaagaaaaa aagaacagag a                                           441
```

```
<210> SEQ ID NO 115
<211> LENGTH: 431
<212> TYPE: DNA
<213> ORGANISM: Human
<220> FEATURE:
<221> NAME/KEY: modified_base
<222> LOCATION: (317)
<223> OTHER INFORMATION: Where n is a, c, g or t

<400> SEQUENCE: 115

gccgcccggg caggtccatt ggcggtgaca aaaggaaaag aagcaaagag a ctcagtcca     60

taatgctgat tagttagaag aaagggctag gattgagaaa gtaccaggaa c ttttaatta    120

tttaaaagag aatgctgact gttaatgttt taaatcttac tgttcaaatg t actaatatg    180

aatttttacc ctttgtgcat gaatattcta aacaactaga agacctccac a atttagcag    240

ttatgaaagt taaacttttt attataaaaa ttctaaacct tactgctcct t taccaggaa    300

catgacacac tatttancat cagttgcata cctcgccaat agtataattc a actgtcttg    360

cccgaacaat catctccatc tggaagacgt aagcctttag aaacacattt t tctattaat    420

ttctctagaa c                                                      431
```

```
<210> SEQ ID NO 116
<211> LENGTH: 421
<212> TYPE: DNA
<213> ORGANISM: Human

<400> SEQUENCE: 116

gtcgcggccg aggtccagaa atgaagaaga agtttgcaga tgtatttgca a agaagacga     60

aggcagagtg gtgtcaaatc tttgacggca cagatgcctg tgtgactccg g ttctgactt    120
```

-continued

```
ttgaggaggt tgttcatcat gatcacaaca aggaaccggg gctcgtttat c accagtgag    180

gagcaggacg tgagcccccg ccctgcacct ctgctgttaa acaccccagc c atcccttct    240

ttcaaaaggg atcctttcat aggagaacac actgaggaga tacttgaaga a tttggattc    300

agcccgcgaa gagatttatc aagcttaact cagataaaat cattgaaagt a ataaggtaa    360

aagctaagtc tctaacttcc aggcccacgg ctcaagtgaa tttcgaatac t gcatttaca    420

g                                                                    421
```

<210> SEQ ID NO 117
<211> LENGTH: 489
<212> TYPE: DNA
<213> ORGANISM: Human

<400> SEQUENCE: 117

```
agcgtggtcg cggccgaggt aaggctgcga ggttgtggtg tctgggaaac t ccgaggaca     60

gagggctaaa tccatgaagt ttgtggatgg cctgatgatc cacagcggag a ccctgttaa    120

ctactacgtt gacactgctg tgcgccacgt gttgctcaga cagggtgtgc t gggcatcaa    180

ggtgaagatc atgctgccct gggacccaac tggtaagatt ggccctaaga a gcccctgcc    240

tgaccacgtg agcattgtgg aacccaaaga tgagatactg cccaccaccc c catctcaga    300

acagaagggt gggaagccag agccgcctgc catgccccag ccagtcccca c agcataaca    360

gggtctcctt ggcagacctg cccgggcggc cgctcgaaag cccgaattcc a gcacactgg    420

cggccgttac tagtggatcc cagctcggta ccaagcttgg cgtaatcatg g tcatagctg    480

gtttcctgt                                                            489
```

<210> SEQ ID NO 118
<211> LENGTH: 489
<212> TYPE: DNA
<213> ORGANISM: Human

<400> SEQUENCE: 118

```
tcgagcggcc gcccgggcag gtattgaata cagcaaaatt ctatatacaa a gtgacctgg     60

acctgctgct tcaaaacatg atcctttctt actaatatct tgatagtcgg t ccatagagc    120

attagaaagc aattgactct taaataaaca gaaaagtgcc taatgcacat t aaatgaatg    180

gcctaactac tggaacttta gtagttctat aaggtgatta acataggtag g atccagttc    240

ctatgacagg ctgctgaaga acagatatga gcatcaagag gccattttgt g cactgccac    300

cgtgatgcca tcgtgtttct ggatcataat gttcccatta tctgattcta g acacaccac    360

aggaatatca gtggggtcag aggttagctt agctgcttgc tgggctagaa c agatatcac    420

tccagcatgc tcatctgaca gggtcccgcg gcaacccaga ttaagtcctt g tgaatctgt    480

gcacaggga                                                            489
```

<210> SEQ ID NO 119
<211> LENGTH: 181
<212> TYPE: DNA
<213> ORGANISM: Human

<400> SEQUENCE: 119

```
taggttccag agacttttgg cccaggagga atatttactt ttagctctgg a catcattac     60

aaaaaggaat atttcccaaa cctcttcaga ccgagaatac atgggtaaaa t tattaaata    120

gttgtataat aaaaataatt ttttccttaa aaaaaaaaaa aacctcggcc g cgaccacgc    180
```

-continued t 181

<210> SEQ ID NO 120
<211> LENGTH: 489
<212> TYPE: DNA
<213> ORGANISM: Human
<220> FEATURE:
<221> NAME/KEY: modified_base
<222> LOCATION: (422)
<223> OTHER INFORMATION: Where n is a, c, g or t
<221> NAME/KEY: modified_base
<222> LOCATION: (487)
<223> OTHER INFORMATION: Where n is a, c, g or t

<400> SEQUENCE: 120
gcgtggtcgc ggccgaggtc catttaaaac aaagaaaaat actaaagcca c tagtaaaca 60 tctgatgtgc aaaatacaac atcctctagt tggctttatg ccattattac a taagctcca 120 aatagctcat cttaaattaa aaagaaaaag tggctgtccc atctctgctg c ataaatcag 180 attttttttt aaaggtttag agtactttaa ggaagggaag ttcaaaactg c cagtgaaat 240 tcacagagaa tacaaattta gcaatttaat ttcccaaagc tctttgaaga a gcaagagag 300 tctctcttct taatgcagtg ttctcccaag aggaactgta attttgcttg g tacttatgc 360 tgggagatat gcaaaatgtg tttttcaatg tttgctagaa tataatggtt c ctcttcagt 420 gnctggttca tcctggaact catgggttaa gaaggacttc ttggagccga a ctgcccggg 480 cgggccntt 489

<210> SEQ ID NO 121
<211> LENGTH: 531
<212> TYPE: DNA
<213> ORGANISM: Human

<400> SEQUENCE: 121
cgagcggccg cccgggcagg tggccagcgc tggtcccgca gacgccgaga t ggaggaaat 60 atttgatgat gcgtcacctg gaaagcaaaa ggaaatccaa gaaccagatc c tacctatga 120 agaaaaaatg caaactgacc gggcaaatag attcgagtat ttattaaagc a gacagaact 180 ttttgcacat ttcattcaac ctgctgctca gaagactcca acttcacctt t gaagatgaa 240 accagggcgc ccacgaataa aaaaagatga gaagcagaac ttactatccg t tggcgatta 300 ccgacaccgt agaacagagc aagaggagga tgaagagcta ttaacagaaa g ctccaaagc 360 aaccaatgtt tgcactcgat ttgaagactc tccatcgtat gtaaaatggg g taaactgag 420 agattatcag gtcccgagga ttaaactggc tcatttcttt gtatgagaat g gcatcaatg 480 gtatccttgc agatgaaatg ggcctaggaa agactcttca acaatttctc t 531

<210> SEQ ID NO 122
<211> LENGTH: 174
<212> TYPE: DNA
<213> ORGANISM: Human

<400> SEQUENCE: 122
tcgagcggcc gcccgggcag gtctgccaac agcagaggcg gggcctccgg c atcttcaaa 60 gcacctctga gcaggctcca gccctctggc tgcgggaggg gtctggggtc t cctctgagc 120 tcggcagcaa agcagatgtt atttctctcc cgcgacctcg gccgcgacca c gct 174

<210> SEQ ID NO 123
<211> LENGTH: 531
<212> TYPE: DNA

<213> ORGANISM: Human
<220> FEATURE:
<221> NAME/KEY: modified_base
<222> LOCATION: (152)
<223> OTHER INFORMATION: Where n is a, c, g or t
<221> NAME/KEY: modified_base
<222> LOCATION: (373)
<223> OTHER INFORMATION: Where n is a, c, g or t
<221> NAME/KEY: modified_base
<222> LOCATION: (482)
<223> OTHER INFORMATION: Where n is a, c, g or t
<221> NAME/KEY: modified_base
<222> LOCATION: (494)
<223> OTHER INFORMATION: Where n is a, c, g or t
<221> NAME/KEY: modified_base
<222> LOCATION: (496)
<223> OTHER INFORMATION: Where n is a, c, g or t
<221> NAME/KEY: modified_base
<222> LOCATION: (502)
<223> OTHER INFORMATION: Where n is a, c, g or t

<400> SEQUENCE: 123

```
agcgtggtcg cggccgaggt cctcaaccaa gagggttgat ggcctccagt c aagaaactg     60

tggctcatgc cagcagagct ctctcctcgt ccagcaggcg ccatgcaagg g caggctaaa    120

agacctccag tgcatcaaca tccatctagc anagagaaaa ggggcactga a gcagctatg    180

tctgccaggg gctaggggct cccttgcaga cagcaatgct acaataaagg a cacagaaat    240

gggggaggtg ggggaagccc tatttttata acaaagtcaa acagatctgt g ccgttcatt    300

cccccagaca cacaagtaga aaaaaaccaa tgcttgtggt ttctgccaag a tggaatatt    360

cctccttcct aanttccaca catggccgtt tgcaatgctc gacagcattg c actgggctg    420

cttgtctctg tggtctgggc accagtagct tgggccccat atacacttct c agttcccac    480

anggcttatg gccnangggc angctccaat tttcaagcac cacgaaggaa g              531
```

<210> SEQ ID NO 124
<211> LENGTH: 416
<212> TYPE: DNA
<213> ORGANISM: Human

<400> SEQUENCE: 124

```
tcgagcggcc gcccgggcag gtccatctat actttctaga gcagtaaatc t cataaattc     60

acttaccaag cccaggaata atgactttta aagccttgaa tatcaactaa g acaaattat    120

gccaattctg atttctcaca tatacttaga ttacacaaag ataaagcttt a gatgtgatc    180

attgtttaat gtagacttat ctttaaagtt tttaattaaa aactacagaa g ggagtaaac    240

agcaagccaa atgatttaac caaatgattt aagagtaaaa ctcactcaga a agcattata    300

cgtaactaaa tatacatgag catgattata tacatacatg aaactgcaat t ttatggcat    360

tctaagtaac tcatttaagt acatttttgg catttaaaca aagatcaaat c aagct        416
```

<210> SEQ ID NO 125
<211> LENGTH: 199
<212> TYPE: DNA
<213> ORGANISM: Human
<220> FEATURE:
<221> NAME/KEY: modified_base
<222> LOCATION: (112)
<223> OTHER INFORMATION: Where n is a, c, g or t
<221> NAME/KEY: modified_base
<222> LOCATION: (160)
<223> OTHER INFORMATION: Where n is a, c, g or t
<221> NAME/KEY: modified_base
<222> LOCATION: (195)
<223> OTHER INFORMATION: Where n is a, c, g or t -continued

<400> SEQUENCE: 125

```
agcgtggtcg cggccgaggt gctttttttt tttttttttt tttttttttt g ctattctaa    60
aggggaaggc cccttttat taaacttgta cattttactt tccttctttc a naatgctaa    120
taaaaaactt ttgtttatac ttaaaaaaac cataaatcan acaaacaaaa g aaacgattc   180
caacatcact tctgngatg                                                 199
```

<210> SEQ ID NO 126
<211> LENGTH: 490
<212> TYPE: DNA
<213> ORGANISM: Human

<400> SEQUENCE: 126

```
cgtggtcgcg gccgaggtcc agttgctcta agtggattgg atatggttgg a gtggcacag    60
actggatctg ggaaaacatt gtcttatttg cttcctgcca ttgtccacat c aatcatcag   120
ccattcctag agagaggcga tgggcctatt tgtttggtgc tggcaccaac t cgggaactg   180
gcccaacagg tgcagcaagt agctgctgaa tattgtagag catgtcgctt g aagtctact   240
tgtatctacg gtggtgctcc taagggacca caaatacgtg atttggagag a ggtgtggaa   300
atctgtattg caacacctgg aagactgatt gactttttag agtgtggaaa a accaatctg   360
agaagaacaa cctaccttgt ccttgatgaa gcagatagaa tgcttgatat g ggctttgaa   420
ccccaaataa ggaagattgt ggatcaaata agacctgata ggcaaactct a atgtggagt   480
gcgacttggc                                                           490
```

<210> SEQ ID NO 127
<211> LENGTH: 490
<212> TYPE: DNA
<213> ORGANISM: Human

<400> SEQUENCE: 127

```
cgtggtcgcg gccgaggtcg gccgaggtct ggagatctga gaacgggcag a ctgcctcct    60
caagtgggtc cctgacccct gacccccgag cagcctaact gggaggcacc c cccagcagg   120
ggcacactga cacctcacac ggcagggtat tccaacagac ctgaagctga g ggtcctgtc   180
tgttagaagg aaaactaaca agcagaaagg acagccacat caaaaaccca t ctgtacatc   240
accatcatca aagaccaaaa gtaaataaaa ccacaaagat gggaaaaaaa c agaacagaa   300
aaactggaaa ctctaaaaag cagagcacct ctcctcttcc aaaggaacgc a gttcctcac   360
cagcaatgga acaaagctgg atggagaatg actttgacga gctgagaaaa g aacgcttca   420
gacgatcaaa ttactctgag ctacgggagg acattcaaac caaaggcaaa g aagttgaaa   480
actttgaaaa                                                           490
```

<210> SEQ ID NO 128
<211> LENGTH: 469
<212> TYPE: DNA
<213> ORGANISM: Human
<220> FEATURE:
<221> NAME/KEY: modified_base
<222> LOCATION: (69)
<223> OTHER INFORMATION: Where n is a, c, g or t
<221> NAME/KEY: modified_base
<222> LOCATION: (106)
<223> OTHER INFORMATION: Where n is a, c, g or t
<221> NAME/KEY: modified_base
<222> LOCATION: (140)
<223> OTHER INFORMATION: Where n is a, c, g or t
<221> NAME/KEY: modified_base
<222> LOCATION: (152)

-continued

<223> OTHER INFORMATION: Where n is a, c, g or t
<221> NAME/KEY: modified_base
<222> LOCATION: (165)
<223> OTHER INFORMATION: Where n is a, c, g or t
<221> NAME/KEY: modified_base
<222> LOCATION: (196)
<223> OTHER INFORMATION: Where n is a, c, g or t
<221> NAME/KEY: modified_base
<222> LOCATION: (224)
<223> OTHER INFORMATION: Where n is a, c, g or t
<221> NAME/KEY: modified_base
<222> LOCATION: (233)
<223> OTHER INFORMATION: Where n is a, c, g or t
<221> NAME/KEY: modified_base
<222> LOCATION: (241)
<223> OTHER INFORMATION: Where n is a, c, g or t
<221> NAME/KEY: modified_base
<222> LOCATION: (258)
<223> OTHER INFORMATION: Where n is a, c, g or t
<221> NAME/KEY: modified_base
<222> LOCATION: (260)
<223> OTHER INFORMATION: Where n is a, c, g or t
<221> NAME/KEY: modified_base
<222> LOCATION: (267)
<223> OTHER INFORMATION: Where n is a, c, g or t
<221> NAME/KEY: modified_base
<222> LOCATION: (291)
<223> OTHER INFORMATION: Where n is a, c, g or t
<221> NAME/KEY: modified_base
<222> LOCATION: (347)
<223> OTHER INFORMATION: Where n is a, c, g or t
<221> NAME/KEY: modified_base
<222> LOCATION: (395)
<223> OTHER INFORMATION: Where n is a, c, g or t

<400> SEQUENCE: 128
cgtggtcgcg gccgaggtgc tttttttttt tttttttttt tttttttttt t gctgattta 60 ttttttctnt ttattgttac atacaatgta taaacacata aaacanaaaa c agtagggat 120 cctctaggat ctctagggan acagtaaagt anaaagaggt ctcanaaaca t tttttttaaa 180 gtacaagaca ttcagngctc ggcccaaagg cgtaaaaggt ttanagccag c anatagctg 240 nactaaaggc tccgtctntn tccccanagc caggacaacc ccagggagct n tccattagc 300 agccagtcca cgcaggcagg atgctgcgga aaaagctcta tgctganaac a ttccccttg 360 atggaaagaa gggcaacaca aaaggggtaa ctaanagctc cttcctctcg t gagggcgac 420 aactgaggaa cagaaaagga gtgtcccatg tcacttttga ccccctccc 469

<210> SEQ ID NO 129
<211> LENGTH: 419
<212> TYPE: DNA
<213> ORGANISM: Human

<400> SEQUENCE: 129
gcgtggtcgc ggccgaggtc tgattttcat ttaaatattt cagagctata g catttgcct 60 ccatgctcaa atccacacca ttggggctta agccgctcat gccaacatta g caaatgaca 120 tgcagtttaa tccagagatc actgcttctg ggctgatgca tgccaacaca c tggcgtgat 180 ccacgttatg tgcatttttc ttcactttag tgggagaatc aatttttact c caaggcttc 240 ttagttgctt aagagttgca ttaaggacac aatctttgtc caccagtctt g aatgatgtg 300 tttttttctt tgtatggtaa acgttttggg ttctggtgca ttcatgactg a taattactg 360 ctttggtaga cggctgctca agtttccttg gaggaactat ttaataggtg g gttacttg 419

<210> SEQ ID NO 130
<211> LENGTH: 354
<212> TYPE: DNA

<213> ORGANISM: Human

<400> SEQUENCE: 130
agcgtggtcg cggccgaggt ccatctgagg agataaccac atcactaaca a agtgggagt 60 gaccccgcag agcacgctgt ggaattccat agttggtctc atccctggtc a gtttccaca 120 tgatgatggt cttatctcga gaggcggaga ggatcatgtc cgggaactgc g gggtagtag 180 cgatctgggt tacccagccg ttgtggccct tgagggtgcc acgaagggtc a tctgctcag 240 tcatggcggc ggcgagagcg tgtgtcgctg cagcgacgag gatggcactg g atggcttag 300 agaaactagc accacaacct ctcctgccgc acctgcccgg gcggcccgct c gaa 354

<210> SEQ ID NO 131
<211> LENGTH: 474
<212> TYPE: DNA
<213> ORGANISM: Human
<220> FEATURE:
<221> NAME/KEY: modified_base
<222> LOCATION: (421)
<223> OTHER INFORMATION: Where n is a, c, g or t

<400> SEQUENCE: 131
cgagcggccg cccgggcagg tctggcagca gcttcctctg gaataattga c agctttgtg 60 ctgcctgact aaaatttgaa atgacaaccg ctgaatgtaa aatgatgtac c tacaatgag 120 agagatttag gaatactatc tgtcaatcca tagatgtaga aacaaaacaa a ctacagaat 180 gaaaacaaac ttattttaaa ccaaagaaac aaatgtatcc aaaatatagt c catgatata 240 tttgattact agtataacca cagttgaaaa cttaaaaaaa aaaattgaca t tttttgtaa 300 tgggtactaa tggatttata aaaggtttct gtttccaaag atgttattgg g gtccacata 360 ttccttgaag acttcagcat cccaaagccc gacatcagag atactttcct t tagccattg 420 nttcccgtaa cttgcccact ccatggtgat gtgacaggct tcccttcatt a gca 474

<210> SEQ ID NO 132
<211> LENGTH: 474
<212> TYPE: DNA
<213> ORGANISM: Human
<220> FEATURE:
<221> NAME/KEY: modified_base
<222> LOCATION: (403)
<223> OTHER INFORMATION: Where n is a, c, g or t

<400> SEQUENCE: 132
ggccgaggtg ggaattcat gtggaggtca gagtggaagc aggtgtgaga g ggtccagca 60 gaaggaaaca tggctgccaa agtgtttgag tccattggca agtttggcct g gccttagct 120 gttgcaggag gcgtggtgaa ctctgcctta tataatgtgg atgctgggca c agagctgtc 180 atctttgacc gattccgtgg agtgcaggac attgtggtag gggaagggac t cattttctc 240 atcccgtggg tacagaaacc aattatcttt gactgccgtt ctcgaccacg t aatgtgcca 300 gtcatcactg gtagcaaaga tttacagaat gtcaacatca cactgcgcat c ctcttccgg 360 cctgtcgcca gccagcttcc tcgcatcttc accagcatcg ganaggacta t gatgaaccg 420 tgtgctgccg tccatcacaa ctgagatcct caagtcagtg gtggctcgct t tga 474

<210> SEQ ID NO 133
<211> LENGTH: 387
<212> TYPE: DNA
<213> ORGANISM: Human

<400> SEQUENCE: 133

```
tgctcgagcg gccgccagtg tgatggatat ctgcagaatt cggcttagcg t ggtcgcggc     60

cgaggtctgc gggcccctta gcctgccctg cttccaagcg acggccatcc c agtagggga    120

ctttcccaca ctgtgccttt acgatcagcg tgacagagta gaagctggag t gcctcacca    180

cacggcccgg aaacagcggg aagtaactgg aaagagcttt aggacagctt a gatgccgag    240

tgggcgaatg ccagaccaat gatacccaga gctacctgcc gccaacttgt t gagatgtgt    300

gtttgactgt gagagagtgt gtgtttgtgt gtgtgttttg ccatgaactg t ggccccagt    360

gtatagtgtt tcagtggggg agaactg                                         387
```

```
<210> SEQ ID NO 134
<211> LENGTH: 401
<212> TYPE: DNA
<213> ORGANISM: Human

<400> SEQUENCE: 134

ggccgcccgg gcaggtctga tgaagaacac gggtgtgatc cttgccaatg a cgccaatgc     60

tgagcggctc aagagtgttg tgggcaactt gcatcggctg ggagtcacca a caccattat    120

cagccactat gatgggcgcc agttccccaa ggtggtgggg ggctttgacc g agtactgct    180

ggatgctccc tgcagtggca ctggggtcat ctccaaggat ccagccgtga a gactaacaa    240

ggatgagaag gacatcctgc gcttgtgctc acctccagaa ggaagttgct c ctgagtgct    300

attgactctt gtcaatgcga ccttcaagac aggaggctac ctggtttact g cacctgttc    360

tatcacagtg agacctctgc catggcagaa caggggaagc t                         401
```

```
<210> SEQ ID NO 135
<211> LENGTH: 451
<212> TYPE: DNA
<213> ORGANISM: Human

<400> SEQUENCE: 135

ggtcgcggcc gaggtctgtt cctgagaaca gcctgcattg gaatctacag a gaggacaac     60

taatgtgagt gaggaagtga ctgtatgtgg actgtggaga aagtaagtca c gtgggccct    120

tgaggacctg gactgggtta ggaacagttg tactttcaga ggtgaggtgt c gagaaggga    180

aagtgaatgt ggtctggagt gtgtccttgg ccttggctcc acagggtgtg c tttcctctg    240

gggccgtcag ggagctcatc ccttgtgttc tgccagggtg gggtaccggg g tttgacact    300

gaggagggta acctgctggc tggagcggca gaacagtggc cttgatttgt c ttttggaag    360

attttaaaaa ccaaaaagca taaacattct ggtccttcac aatgctttct c tgaagaaat    420

acttaacgga aggacttctc cattcaccat t                                    451
```

```
<210> SEQ ID NO 136
<211> LENGTH: 411
<212> TYPE: DNA
<213> ORGANISM: Human

<400> SEQUENCE: 136

ggccgcccgg gcaggtctga atcacgtaga atttgaagat caagatgatg a agccagagt     60

tcagtatgag ggttttcgac ctgggatgta tgtccgcgtt gagattgaaa a tgttccctg    120

tgaatttgtg cagaactttg accccttta ccccattatc ctgggtggct t gggcaacag    180

tgagggaaat gttggacatg tgcaggtggg tccctttgct gcgtatttgg t gcctgaggc    240

tctgtggatt tcccctccat caatcatctt accctctcat cccctcaga t gcgtctgaa    300
```

```
gaaacatctc tggtataaga aaatcctcaa gtcccaagat ccaatcatat t ttctgtagg    360

gtggaggaag tttcagacca tcctgctcta ttatatccga agaccacaat g              411


<210> SEQ ID NO 137
<211> LENGTH: 211
<212> TYPE: DNA
<213> ORGANISM: Human
<220> FEATURE:
<221> NAME/KEY: modified_base
<222> LOCATION: (186)
<223> OTHER INFORMATION: Where n is a, c, g or t

<400> SEQUENCE: 137

cggccgcccg ggcaggtcgg ttggtgcggc ctccattgtt cgtgttttaa g gcgccatga     60

ggggtgacag aggccgtggt cgtggtgggc gctttggttc cagaggaggc c caggaggag    120

ggttcaggcc ctttgcacca catatcccat ttgacttcta tttgtgtgaa a tggcctttc    180

cccggntcaa gccagcacct cgatgaaact t                                   211


<210> SEQ ID NO 138
<211> LENGTH: 471
<212> TYPE: DNA
<213> ORGANISM: Human

<400> SEQUENCE: 138

gccgcccggg caggtctggg ctggcgactg gcatccaggc cgtaactgca a atctatgct     60

aggcggggtc tcccttctgt gtgttcaagt gttctcgact tggattctta a ctattttaa    120

aaaatgcact gagtttgggt taaaaaccaa ccaccaaaat ggatttcaac a cagctctaa    180

agccaagggc gtggccggct ctcccaacac agcgactcct ggaggccagg t gcccatggg    240

cctacatccc ctctcagcac tgaacagtga gttgattttt ctttttacaa t aaaaaaagc    300

tgagtaatat tgcataggag taccaagaaa ctgcctcatt ggaaacaaaa a ctatttaca    360

ttaaataaaa agcctggccg caggctgcgt ctgccacatt tacagcacgg t gcgatgcac    420

acggtgacca aaccacggag gcaagcttct ggcactcaca ccacgacccg c              471


<210> SEQ ID NO 139
<211> LENGTH: 481
<212> TYPE: DNA
<213> ORGANISM: Human
<220> FEATURE:
<221> NAME/KEY: modified_base
<222> LOCATION: (384)
<223> OTHER INFORMATION: Where n is a, c, g or t

<400> SEQUENCE: 139

gtcgcggccg aggtctgttc tttagctcag atttaaacct gctgtctctt c tttatttgc     60

agaatgaatt cccagttcct gagcagttca agaccctatg gaacgggcag a agttggtca    120

ccacagtgac agaaattgct ggataagcga agtgccactg ggttctttgc c ctcccttca    180

caccatggga taaatctgta tcaagacggt tcttttctag atttcctcta c ctttttgct    240

cttaaaactg cttctctgct ctgagaagca cagctacctg ccttcactga a atatacctc    300

aggctgaaat ttggggtggg atagcaggtc agttgatctt ctgcaggaag g tgcagcttt    360

tccatatcag ctcaaccacg ccgncagtcc attcttaagg aactgccgac t aggactgat    420

gatgcatttt agcttttgag cttttggggg gtattctacc aaccaacagt c catttggaa    480

a                                                                    481
```

-continued

<210> SEQ ID NO 140
<211> LENGTH: 421
<212> TYPE: DNA
<213> ORGANISM: Human
<220> FEATURE:
<221> NAME/KEY: modified_base
<222> LOCATION: (372)
<223> OTHER INFORMATION: Where n is a, c, g or t

<400> SEQUENCE: 140
gtcgcggccg aggtttccca tttaagaaaa atagatcttg agattctgat t cttttccaa 60 acagtcccct gctttcatgt acagcttttt ctttacctta cccaaaattc t ggccttgaa 120 gcagttttcc tctatggctt tgcctttctg attttctcag aggctcgagt c tttaatata 180 accccaaatg aaagaaccaa ggggaggggt gggatggcac tttttttgt t ggtcttgtt 240 ttgttttgtt ttttggttgg ttgggttccg ttattttta agattagcca t tctctgctg 300 ctatttccct acataatgtc aatttttaac cataattttg acatgattga g atgtacttg 360 aggcttttt gntttaattg agaaaagact ttgcaatttt tttttagga t gagcctctc 420 c 421

<210> SEQ ID NO 141
<211> LENGTH: 242
<212> TYPE: DNA
<213> ORGANISM: Human
<220> FEATURE:
<221> NAME/KEY: modified_base
<222> LOCATION: (4)
<223> OTHER INFORMATION: Where n is a, c, g or t
<221> NAME/KEY: modified_base
<222> LOCATION: (6)
<223> OTHER INFORMATION: Where n is a, c, g or t
<221> NAME/KEY: modified_base
<222> LOCATION: (20)
<223> OTHER INFORMATION: Where n is a, c, g or t
<221> NAME/KEY: modified_base
<222> LOCATION: (31)
<223> OTHER INFORMATION: Where n is a, c, g or t
<221> NAME/KEY: modified_base
<222> LOCATION: (35)
<223> OTHER INFORMATION: Where n is a, c, g or t
<221> NAME/KEY: modified_base
<222> LOCATION: (39)
<223> OTHER INFORMATION: Where n is a, c, g or t
<221> NAME/KEY: modified_base
<222> LOCATION: (72)
<223> OTHER INFORMATION: Where n is a, c, g or t
<221> NAME/KEY: modified_base
<222> LOCATION: (94)
<223> OTHER INFORMATION: Where n is a, c, g or t
<221> NAME/KEY: modified_base
<222> LOCATION: (141)
<223> OTHER INFORMATION: Where n is a, c, g or t
<221> NAME/KEY: modified_base
<222> LOCATION: (142)
<223> OTHER INFORMATION: Where n is a, c, g or t
<221> NAME/KEY: modified_base
<222> LOCATION: (211)
<223> OTHER INFORMATION: Where n is a, c, g or t
<221> NAME/KEY: modified_base
<222> LOCATION: (222)
<223> OTHER INFORMATION: Where n is a, c, g or t

<400> SEQUENCE: 141
cgantngccc gcccgggcan gtctgtctaa ntttntcang gaccacgaac a gaaactcgt 60 gcttcaccga anaacaatat cttaaacatc gaanaattta aatattatga a aaaaaacat 120 tgcaaaatat aaaataaata nnaaaaggaa aggaaacttt gaaccttatg t accgagcaa 180 atccaggtct agcaaacagt gctagtccta nattacttga tntacaacaa c acatgaata 240 ca 242

<210> SEQ ID NO 142
<211> LENGTH: 551
<212> TYPE: DNA
<213> ORGANISM: Human
<220> FEATURE:
<221> NAME/KEY: modified_base
<222> LOCATION: (15)
<223> OTHER INFORMATION: Where n is a, c, g or t
<221> NAME/KEY: modified_base
<222> LOCATION: (19)
<223> OTHER INFORMATION: Where n is a, c, g or t
<221> NAME/KEY: modified_base
<222> LOCATION: (32)
<223> OTHER INFORMATION: Where n is a, c, g or t
<221> NAME/KEY: modified_base
<222> LOCATION: (73)
<223> OTHER INFORMATION: Where n is a, c, g or t
<221> NAME/KEY: modified_base
<222> LOCATION: (110)
<223> OTHER INFORMATION: Where n is a, c, g or t
<221> NAME/KEY: modified_base
<222> LOCATION: (278)
<223> OTHER INFORMATION: Where n is a, c, g or t
<221> NAME/KEY: modified_base
<222> LOCATION: (405)
<223> OTHER INFORMATION: Where n is a, c, g or t
<221> NAME/KEY: modified_base
<222> LOCATION: (436)
<223> OTHER INFORMATION: Where n is a, c, g or t
<221> NAME/KEY: modified_base
<222> LOCATION: (473)
<223> OTHER INFORMATION: Where n is a, c, g or t
<221> NAME/KEY: modified_base
<222> LOCATION: (510)
<223> OTHER INFORMATION: Where n is a, c, g or t

<400> SEQUENCE: 142
agcgtggtcg cggcncgang tccacagggc anatattctt ttagtgtctg g aattaaaat 60 gtttgaggtt tangtttgcc attgtctttc caaaaggcca aataattcan a tgtaaccac 120 accaagtgca aacctgtgct ttctatttca cgtactgttg tccatacagt t ctaaataca 180 tgtgcagggg attgtagcta atgcattaca cagtcgttca gtcttctctg c agacacact 240 aagtgatcat accaacgtgt tatacactca actagaanat aataagcttt a atctgaggg 300 caagtacagt cctgacaaaa gggcaagttt gcataataga tcttcgatca a ttctctctc 360 caaggggccc gcaactaggc tattattcat aaaacacaac tgaanagggg a ttggtttta 420 ctggtaaatc atgtgntgct aaatcatttt ctgaacagtg gggtctaaat c antcattga 480 tttagtggca gccacctgcc cggcggccgn tcgaagccca attctgcaga t atccatcac 540 actggcggcc g 551

<210> SEQ ID NO 143
<211> LENGTH: 515
<212> TYPE: DNA
<213> ORGANISM: Human
<220> FEATURE:
<221> NAME/KEY: modified_base
<222> LOCATION: (5)
<223> OTHER INFORMATION: Where n is a, c, g or t
<221> NAME/KEY: modified_base
<222> LOCATION: (286)
<223> OTHER INFORMATION: Where n is a, c, g or t
<221> NAME/KEY: modified_base
<222> LOCATION: (498)
<223> OTHER INFORMATION: Where n is a, c, g or t

<400> SEQUENCE: 143

```
cgagnggccc gcccgggcag gtatcttcac aaactcaaca aaggcactac a tgagacttc     60

acattcccct agtccaatag ctgacaaatt tttgcaacgt tctgcaatgc g aattaactc    120

ttcatcaagt ggccgtaatc catttgcaca cactactagt tcaaccagtc t agggcatgt    180

cattcccaca cggccaagca catctttgct tactgatctc ccaaagtaca g atgggtggc    240

aggtatttca tagcgaaaga aggggtcaaa ttcttcttca tataanaaaa a atacatcac    300

taagttcact ttgggtgaat gtctgatgaa agcatcccag ctactcttct g aatagtatg    360

gaagtgtgtc tgtccaggat tctcactgac tacatcaatg cgcaaatgtt c taatcgaac    420

atgtttttca gaagacaatg caagtaacaa ctcatcactc aataagtggt a agttcaggg    480

ctagttctct taagccgnga cactgatcag cacac                                515
```

<210> SEQ ID NO 144
<211> LENGTH: 247
<212> TYPE: DNA
<213> ORGANISM: Human
<220> FEATURE:
<221> NAME/KEY: modified_base
<222> LOCATION: (11)
<223> OTHER INFORMATION: Where n is a, c, g or t
<221> NAME/KEY: modified_base
<222> LOCATION: (20)
<223> OTHER INFORMATION: Where n is a, c, g or t
<221> NAME/KEY: modified_base
<222> LOCATION: (42)
<223> OTHER INFORMATION: Where n is a, c, g or t
<221> NAME/KEY: modified_base
<222> LOCATION: (115)
<223> OTHER INFORMATION: Where n is a, c, g or t
<221> NAME/KEY: modified_base
<222> LOCATION: (152)
<223> OTHER INFORMATION: Where n is a, c, g or t
<221> NAME/KEY: modified_base
<222> LOCATION: (165)
<223> OTHER INFORMATION: Where n is a, c, g or t
<221> NAME/KEY: modified_base
<222> LOCATION: (181)
<223> OTHER INFORMATION: Where n is a, c, g or t
<221> NAME/KEY: modified_base
<222> LOCATION: (195)
<223> OTHER INFORMATION: Where n is a, c, g or t
<221> NAME/KEY: modified_base
<222> LOCATION: (208)
<223> OTHER INFORMATION: Where n is a, c, g or t
<221> NAME/KEY: modified_base
<222> LOCATION: (221)
<223> OTHER INFORMATION: Where n is a, c, g or t

<400> SEQUENCE: 144

```
tgcattctct ntggatgcan acctgcccgt tggtagggac tntgctcaca c ggaacatgg     60

acggttacac ctgtgccgtg ggtgacgtcc accagcttct ggatcatctc g gcgngggtg    120

ttgtggaagg gcagactatc cacctccatg cncacgatgc ccganacgcc a ctccggact    180

ntgtgctgca ccaanatgcc cagcattnta tcttcaagca nagcacttat c agggtcctt    240

ggcacac                                                               247
```

<210> SEQ ID NO 145
<211> LENGTH: 309
<212> TYPE: DNA
<213> ORGANISM: Human
<220> FEATURE:
<221> NAME/KEY: modified_base
<222> LOCATION: (18)
<223> OTHER INFORMATION: Where n is a, c, g or t
<221> NAME/KEY: modified_base
<222> LOCATION: (155)

<223> OTHER INFORMATION: Where n is a, c, g or t
<221> NAME/KEY: modified_base
<222> LOCATION: (247)
<223> OTHER INFORMATION: Where n is a, c, g or t

<400> SEQUENCE: 145

```
cgtgggtcgc ggcccgangt ctgctgtaac aaaacaccat agtctgggca g ctcatagac     60

aatggaattt tatttctcac gcttctggag gctggattcc aagatcaagg t tccaggaga    120

ctcagtgtct ggcaaggtct cggtttctgc ctcanagatg gtgccatctg g ctgtgtcct    180

cacaagtagg aaggtgcaag aagctcccct caggctctgt ctgtaagaca c tgatcccat    240

tcatganggg gaaacgtaat gacctaatca gcccccagag accccacttc t aacaccatc    300

accttgggg                                                            309
```

<210> SEQ ID NO 146
<211> LENGTH: 486
<212> TYPE: DNA
<213> ORGANISM: Human
<220> FEATURE:
<221> NAME/KEY: modified_base
<222> LOCATION: (16)
<223> OTHER INFORMATION: Where n is a, c, g or t
<221> NAME/KEY: modified_base
<222> LOCATION: (97)
<223> OTHER INFORMATION: Where n is a, c, g or t
<221> NAME/KEY: modified_base
<222> LOCATION: (154)
<223> OTHER INFORMATION: Where n is a, c, g or t
<221> NAME/KEY: modified_base
<222> LOCATION: (244)
<223> OTHER INFORMATION: Where n is a, c, g or t
<221> NAME/KEY: modified_base
<222> LOCATION: (275)
<223> OTHER INFORMATION: Where n is a, c, g or t
<221> NAME/KEY: modified_base
<222> LOCATION: (322)
<223> OTHER INFORMATION: Where n is a, c, g or t
<221> NAME/KEY: modified_base
<222> LOCATION: (347)
<223> OTHER INFORMATION: Where n is a, c, g or t
<221> NAME/KEY: modified_base
<222> LOCATION: (349)
<223> OTHER INFORMATION: Where n is a, c, g or t
<221> NAME/KEY: modified_base
<222> LOCATION: (352)
<223> OTHER INFORMATION: Where n is a, c, g or t
<221> NAME/KEY: modified_base
<222> LOCATION: (357)
<223> OTHER INFORMATION: Where n is a, c, g or t
<221> NAME/KEY: modified_base
<222> LOCATION: (449)
<223> OTHER INFORMATION: Where n is a, c, g or t
<221> NAME/KEY: modified_base
<222> LOCATION: (460)
<223> OTHER INFORMATION: Where n is a, c, g or t
<221> NAME/KEY: modified_base
<222> LOCATION: (472)
<223> OTHER INFORMATION: Where n is a, c, g or t

<400> SEQUENCE: 146

```
agcgtgggtc gcggcncgac gtcctgtcca tatttcacag cccgagaact a atacaagat     60

gctgacatca tattttgtcc ctacaactat cttctanatg cacaaataag g gaaagtatg    120

gatttaaatc tgaaagaaca ggttgtcatt ttanatgaag ctcataacat c gaggactgt    180

gctcgggaat cagcaagtta cagtgtaaca gaagttcagc ttcggtttgc t cgggatgaa    240

ctanatagta tggtcaacaa taatataagg aaganagatc atgaacccct a cgagctgtg    300

tgctgtagcc tcattaattg gntagaagca aacgctgaat atcttgnana a ngagantat    360
```

-continued

```
gaatcagctt gtaaaatatg gagtggaaat gaaatgctct taactttaca c aaaatgggt    420

atcaccactg ctacttttcc cattttgcng gtaagatatn ttttctacct g ngaaacgta    480

tttaag                                                              486
```

<210> SEQ ID NO 147
<211> LENGTH: 430
<212> TYPE: DNA
<213> ORGANISM: Human
<220> FEATURE:
<221> NAME/KEY: modified_base
<222> LOCATION: (12)
<223> OTHER INFORMATION: Where n is a, c, g or t
<221> NAME/KEY: modified_base
<222> LOCATION: (26)
<223> OTHER INFORMATION: Where n is a, c, g or t
<221> NAME/KEY: modified_base
<222> LOCATION: (28)
<223> OTHER INFORMATION: Where n is a, c, g or t
<221> NAME/KEY: modified_base
<222> LOCATION: (289)
<223> OTHER INFORMATION: Where n is a, c, g or t
<221> NAME/KEY: modified_base
<222> LOCATION: (299)
<223> OTHER INFORMATION: Where n is a, c, g or t
<221> NAME/KEY: modified_base
<222> LOCATION: (352)
<223> OTHER INFORMATION: Where n is a, c, g or t
<221> NAME/KEY: modified_base
<222> LOCATION: (390)
<223> OTHER INFORMATION: Where n is a, c, g or t
<221> NAME/KEY: modified_base
<222> LOCATION: (399)
<223> OTHER INFORMATION: Where n is a, c, g or t

<400> SEQUENCE: 147

```
gccgcccggg cangttcgac attacntnga gttccatgat gtacaattct t tcacgaaaa     60

acaatgaatg caagaatttg aggatctcct tactcctccc ttttacagat g gtctctcaa    120

tcccttcttc ttcctcttca tcttcatctt cttctgaacg cgctgccggg t accacggct    180

ttctttgtct ttatcgtgag atgaaggtga tgcttctgtt tcttctacca t aactgaaga    240

aatttcgctg caagtctctt gactggctgt ttctccgact tcgcctttnt g tcaaacgng    300

agtcttttta cctcatgccc ctcagcttca cagcatcttc atctggatgt t natttctca    360

aagggctcac tgaggaaact tctgattcan atgtcgaana gcactgtgaa g ttttctctt    420

cattttgctg                                                          430
```

<210> SEQ ID NO 148
<211> LENGTH: 483
<212> TYPE: DNA
<213> ORGANISM: Human
<220> FEATURE:
<221> NAME/KEY: modified_base
<222> LOCATION: (20)
<223> OTHER INFORMATION: Where n is a, c, g or t
<221> NAME/KEY: modified_base
<222> LOCATION: (24)
<223> OTHER INFORMATION: Where n is a, c, g or t
<221> NAME/KEY: modified_base
<222> LOCATION: (53)
<223> OTHER INFORMATION: Where n is a, c, g or t
<221> NAME/KEY: modified_base
<222> LOCATION: (55)
<223> OTHER INFORMATION: Where n is a, c, g or t
<221> NAME/KEY: modified_base
<222> LOCATION: (374)
<223> OTHER INFORMATION: Where n is a, c, g or t
<221> NAME/KEY: modified_base
<222> LOCATION: (381)
<223> OTHER INFORMATION: Where n is a, c, g or t -continued
<221> NAME/KEY: modified_base
<222> LOCATION: (423)
<223> OTHER INFORMATION: Where n is a, c, g or t
<221> NAME/KEY: modified_base
<222> LOCATION: (431)
<223> OTHER INFORMATION: Where n is a, c, g or t
<221> NAME/KEY: modified_base
<222> LOCATION: (459)
<223> OTHER INFORMATION: Where n is a, c, g or t

<400> SEQUENCE: 148
cccgggcagg tctgtgttgn tttncaaccg gtgtcctccc cagcgtccag a ananggaaa 60 tgtggagcgg gtgatgatga cccctcgctg tcctgtcacc tcctgcacag c ttcgtatgt 120 gggtctggtc tgggaccacc cgtacaggtt gtgcacgttg tagtgctcca c gggggagct 180 gtccggcagg atctgctgac tctccatgca cagagtcttg ctgctcaggc c cttgtccct 240 agattccaaa tatggcatat agggtggggt tatttagcat ttcattgctg c agcccctga 300 cagatccatc cacaaaattt gatggctcat tcatatcaat ccacaatcca t caaacttca 360 agctcttctc tggntctcga nggtttgcat agaactcttc tatctctttc t tccaccacg 420 canacctcgg ncgcgaccac gctaagccga attctgcana tatccatcac a ctggcggcc 480 gct 483

<210> SEQ ID NO 149
<211> LENGTH: 439
<212> TYPE: DNA
<213> ORGANISM: Human
<220> FEATURE:
<221> NAME/KEY: modified_base
<222> LOCATION: (11)
<223> OTHER INFORMATION: Where n is a, c, g or t
<221> NAME/KEY: modified_base
<222> LOCATION: (359)
<223> OTHER INFORMATION: Where n is a, c, g or t
<221> NAME/KEY: modified_base
<222> LOCATION: (384)
<223> OTHER INFORMATION: Where n is a, c, g or t
<221> NAME/KEY: modified_base
<222> LOCATION: (402)
<223> OTHER INFORMATION: Where n is a, c, g or t

<400> SEQUENCE: 149
ctttcacgaa nacaatgaat gcaagaattt gaggatctcc ttactcctcc c ttttacaga 60 tggtctctca atcccttctt cttcctcttc atcttcatct tcttctgaac g cgctgccgg 120 gtaccacggc tttctttgtc tttatcgtga gatgaaggtg atgcttctgt t tcttctacc 180 ataactgaag aaatttcgct gcaagtctct tgactggctg tttctccgac t tcgcctttt 240 tgcaaacgtg agtcttttta cctcatgccc ctcagcttcc acagcatctt c atctggatg 300 ttcatttctc aaagggctca ctgaggaaac ttctgactca catgtcgaag a agcactgng 360 agtttctctt catttgctgc aaanttgctc tttgctggct gngctctcag a ccacccatt 420 tggctgcatg gggctgac 439

<210> SEQ ID NO 150
<211> LENGTH: 578
<212> TYPE: DNA
<213> ORGANISM: Human
<220> FEATURE:
<221> NAME/KEY: modified_base
<222> LOCATION: (4)
<223> OTHER INFORMATION: Where n is a, c, g or t
<221> NAME/KEY: modified_base
<222> LOCATION: (15)
<223> OTHER INFORMATION: Where n is a, c, g or t -continued
<221> NAME/KEY: modified_base
<222> LOCATION: (260)
<223> OTHER INFORMATION: Where n is a, c, g or t
<221> NAME/KEY: modified_base
<222> LOCATION: (336)
<223> OTHER INFORMATION: Where n is a, c, g or t
<221> NAME/KEY: modified_base
<222> LOCATION: (371)
<223> OTHER INFORMATION: Where n is a, c, g or t
<221> NAME/KEY: modified_base
<222> LOCATION: (430)
<223> OTHER INFORMATION: Where n is a, c, g or t
<221> NAME/KEY: modified_base
<222> LOCATION: (461)
<223> OTHER INFORMATION: Where n is a, c, g or t
<221> NAME/KEY: modified_base
<222> LOCATION: (535)
<223> OTHER INFORMATION: Where n is a, c, g or t
<221> NAME/KEY: modified_base
<222> LOCATION: (572)
<223> OTHER INFORMATION: Where n is a, c, g or t

<400> SEQUENCE: 150
ggcncgcccg ggcangtcca ctccactttt gagctctgag ggaatacctt c aggagggac 60 agggtcaggg agtcctggca gctccgcagc agagattcac attcattcag a gacttgttg 120 tccagtgcaa tgccattgat cgcaacgatc ctgtctccca cagcaaggga c ccttcttta 180 gcggcagggc ttccaggcag cacagcggca gcatacactc cattctccag a ctgatgcca 240 ctgtctttct gtccactgan gttgatgtgc agcggcgtga ccaccttccc a cccagggac 300 ttcctccgcc gcacgaccat gttgatgggc cccctnccca ttgaggagcg c cttgatggc 360 ctgcttcttg nccttggtga tgaagtccac atcggtgatt ctcacagcca g tcattgacc 420 cttaagcggn catcagcaat gcttcctttg gccactttag ngacaaatat g ccacagtcc 480 ccgggaaaca agggtcattc acaccttctg gcatatcaaa cacctcggcc g gganacacta 540 agccgaattc tgcagatatc catcacactg gngggccg 578

<210> SEQ ID NO 151
<211> LENGTH: 503
<212> TYPE: DNA
<213> ORGANISM: Human
<220> FEATURE:
<221> NAME/KEY: modified_base
<222> LOCATION: (392)
<223> OTHER INFORMATION: Where n is a, c, g or t
<221> NAME/KEY: modified_base
<222> LOCATION: (464)
<223> OTHER INFORMATION: Where n is a, c, g or t

<400> SEQUENCE: 151
cgagcggccc gcccgggcag gtctgggaga tcagcgactg ctgccacgtg c ccagaaatg 60 gctcgtcctt tcactacagc ggaatgcaat gagggtgggt gagaagatga t gggtcggtt 120 atttcattcc ttttcttttt acaacttcac tttcagagac ttcagcgttc c atgtctgct 180 gtgctgtgga acccagagtg ctcttgcctg gatggctgag aatcccttgg a ccctggaag 240 cacctactcc atgatggccc ggtatagtgc aggctcaata taatcttccc g gtatcttga 300 gttgataact cgttgccgtt tcttttcttg cttaacctct ttctctgtga a aatctcatt 360 gaagcgcatg tctgaagcta ctgacagtct anatttgact ctcttgggaa g ctcttcatc 420 cagtgtgtat acatcatctc tcttaaccac aagttggagc catncttaaa c ttcacctgg 480 tacatttgga tagggtggga ggc 503

<210> SEQ ID NO 152

```
<211> LENGTH: 553
<212> TYPE: DNA
<213> ORGANISM: Human
<220> FEATURE:
<221> NAME/KEY: modified_base
<222> LOCATION: (293)
<223> OTHER INFORMATION: Where n is a, c, g or t
<221> NAME/KEY: modified_base
<222> LOCATION: (432)
<223> OTHER INFORMATION: Where n is a, c, g or t
<221> NAME/KEY: modified_base
<222> LOCATION: (459)
<223> OTHER INFORMATION: Where n is a, c, g or t
<221> NAME/KEY: modified_base
<222> LOCATION: (481)
<223> OTHER INFORMATION: Where n is a, c, g or t
<221> NAME/KEY: modified_base
<222> LOCATION: (536)
<223> OTHER INFORMATION: Where n is a, c, g or t

<400> SEQUENCE: 152

agcgtggtcg cggcccgagg tccactgagc tccgccttcc ccgggctccc t gaggaagca     60

gagtcctgac ttccaggaag gacaggacac agaggcaaga actcagcctg t gaggctctg    120

ggtggctcct gaggccagag gacgccttcc gcgatccatg gctcagcatc g tccttctgg    180

cttcccagcc ccgggccgaa cgttcgggtt aataagcaga gcagttattc g gctcctggc    240

aggagctccc ccgttagttt ccacgttgtg agcacattca tacttaagac t gnttctctt    300

tgtgttttaa gcgtctgtct ctgtagtaaa ctgaaatgtt aacagaaatg c agacctgcc    360

cgggcggccg ctcgaaagcc gaattctgca gatatccatc acactggcgg c cgctcgagc    420

atgcatctag anggcccaat tcgccctata gtgagtcgna ttacaattca c tgggccgcg    480

ntttacaacg tcgtgactgg gaaaaccctg cggtacccac ttaatcgcct t gcagnacat    540

ccccctttcg cca                                                       553


<210> SEQ ID NO 153
<211> LENGTH: 454
<212> TYPE: DNA
<213> ORGANISM: Human
<220> FEATURE:
<221> NAME/KEY: modified_base
<222> LOCATION: (198)
<223> OTHER INFORMATION: Where n is a, c, g or t
<221> NAME/KEY: modified_base
<222> LOCATION: (307)
<223> OTHER INFORMATION: Where n is a, c, g or t
<221> NAME/KEY: modified_base
<222> LOCATION: (325)
<223> OTHER INFORMATION: Where n is a, c, g or t
<221> NAME/KEY: modified_base
<222> LOCATION: (347)
<223> OTHER INFORMATION: Where n is a, c, g or t
<221> NAME/KEY: modified_base
<222> LOCATION: (386)
<223> OTHER INFORMATION: Where n is a, c, g or t
<221> NAME/KEY: modified_base
<222> LOCATION: (389)
<223> OTHER INFORMATION: Where n is a, c, g or t
<221> NAME/KEY: modified_base
<222> LOCATION: (392)
<223> OTHER INFORMATION: Where n is a, c, g or t
<221> NAME/KEY: modified_base
<222> LOCATION: (415)
<223> OTHER INFORMATION: Where n is a, c, g or t
<221> NAME/KEY: modified_base
<222> LOCATION: (425)
<223> OTHER INFORMATION: Where n is a, c, g or t

<400> SEQUENCE: 153

tcgagcggct cgcccgggca ggtccaccta gcatggctcc tctaaacacg c aactcagcg     60
```

```
aggggacccc cttcacctct ggcaagagag ctgggtagat cagaaacttg g tgacacctg    120

gctagcacag agcaggctca cttgtcttgg tcccactacc cagattcctg c agacattgc    180

aaaccaaatg aaggttgntg aatgacccct gtccccagcc acttgttttg g tatcatctg    240

ctctgcagtg gaatgcctgt gtgtttgagt tcactctgca tctgtatatt t gagtataga    300

aaccgantca agtgatctgt gcatncagac acactggggc acctgancac a gaacaaatc    360

accttaacga tctggaatga aactgnganc antgcccgcc tgggtgggtc t gganaaact    420

gccgncttct tgttggacct tggccgcacc acct                               454
```

<210> SEQ ID NO 154
<211> LENGTH: 596
<212> TYPE: DNA
<213> ORGANISM: Human
<220> FEATURE:
<221> NAME/KEY: modified_base
<222> LOCATION: (19)
<223> OTHER INFORMATION: Where n is a, c, g or t
<221> NAME/KEY: modified_base
<222> LOCATION: (33)
<223> OTHER INFORMATION: Where n is a, c, g or t
<221> NAME/KEY: modified_base
<222> LOCATION: (37)
<223> OTHER INFORMATION: Where n is a, c, g or t
<221> NAME/KEY: modified_base
<222> LOCATION: (131)
<223> OTHER INFORMATION: Where n is a, c, g or t
<221> NAME/KEY: modified_base
<222> LOCATION: (377)
<223> OTHER INFORMATION: Where n is a, c, g or t
<221> NAME/KEY: modified_base
<222> LOCATION: (425)
<223> OTHER INFORMATION: Where n is a, c, g or t
<221> NAME/KEY: modified_base
<222> LOCATION: (439)
<223> OTHER INFORMATION: Where n is a, c, g or t
<221> NAME/KEY: modified_base
<222> LOCATION: (505)
<223> OTHER INFORMATION: Where n is a, c, g or t

<400> SEQUENCE: 154

```
agcgtggtcg cggcccgang gcggcctcct gantganggg aagggacgtg g gggcggcca     60

cggcaggatt aacctccatt tcagctaatc atgggagaga ttaaagtctc t cctgattat    120

aactggttta naggtacagt tccccttaaa aagattattg tggatgatga t gacagtaag    180

atatggtcgc tctatgacgc gggcccccga agtatcaggt gtcctctcat a ttcctgccc    240

cctgtcagtg gaactgcaga tgtctttttc cggcagattt tggctctgac t ggatggggt    300

taccgggtta tcgctttgca gtatccagtt tattgggacc atctcgagtt c ttgtgatgg    360

attcacaaaa cttttanacc atttacaatt ggataaagtt catctttttg g cgcttcttt    420

gggangcttt ttggcccana aatttgctga atacactcac aaatctccta g aagccattc    480

cctaatcctc tgcaattcct tcagngacac ctctatcttc aaccaacttg g actggaaac    540

agctttggct gatgcctgca tttatgctca aaaaatagtt cttggaaatt t tcatc        596
```

<210> SEQ ID NO 155
<211> LENGTH: 343
<212> TYPE: DNA
<213> ORGANISM: Human
<220> FEATURE:
<221> NAME/KEY: modified_base
<222> LOCATION: (6)
<223> OTHER INFORMATION: Where n is a, c, g or t
<221> NAME/KEY: modified_base
<222> LOCATION: (11)

<223> OTHER INFORMATION: Where n is a, c, g or t
<221> NAME/KEY: modified_base
<222> LOCATION: (23)
<223> OTHER INFORMATION: Where n is a, c, g or t
<221> NAME/KEY: modified_base
<222> LOCATION: (44)
<223> OTHER INFORMATION: Where n is a, c, g or t
<221> NAME/KEY: modified_base
<222> LOCATION: (58)
<223> OTHER INFORMATION: Where n is a, c, g or t
<221> NAME/KEY: modified_base
<222> LOCATION: (86)
<223> OTHER INFORMATION: Where n is a, c, g or t
<221> NAME/KEY: modified_base
<222> LOCATION: (99)
<223> OTHER INFORMATION: Where n is a, c, g or t
<221> NAME/KEY: modified_base
<222> LOCATION: (279)
<223> OTHER INFORMATION: Where n is a, c, g or t
<221> NAME/KEY: modified_base
<222> LOCATION: (310)
<223> OTHER INFORMATION: Where n is a, c, g or t
<221> NAME/KEY: modified_base
<222> LOCATION: (319)
<223> OTHER INFORMATION: Where n is a, c, g or t

<400> SEQUENCE: 155
ctcganttgg cncgcccggg cangtctgcc tggtttttga ccgngcgagc t atttagnct 60 ctggctctgt ttccggagct caaggnaaaa atcttgaana actcgagcag c ttctgtgga 120 tagccttggg tacacatact gccgagcata gccaatgtac tttctcaata g ctggtgggg 180 aatgggatct attgtttctc caggaaccac ctttagtctt tctgataatg g cttctcaga 240 aactacttca agtacggaag tatttgaatc ttgactatnc atacgagcta c tgtggcact 300 gctaatgggn tctctgctnt ccagctctta ttgcaatcac atg 343

<210> SEQ ID NO 156
<211> LENGTH: 556
<212> TYPE: DNA
<213> ORGANISM: Human
<220> FEATURE:
<221> NAME/KEY: modified_base
<222> LOCATION: (34)
<223> OTHER INFORMATION: Where n is a, c, g or t
<221> NAME/KEY: modified_base
<222> LOCATION: (375)
<223> OTHER INFORMATION: Where n is a, c, g or t
<221> NAME/KEY: modified_base
<222> LOCATION: (530)
<223> OTHER INFORMATION: Where n is a, c, g or t

<400> SEQUENCE: 156
tcgagcggcc cgcccgggca ggtctggcac cacncagatc gattaactgg c tcatctgat 60 ctcgtggccc ccaccctgga actgacttag cacaaaagga cacctcaatt c cttatgatt 120 tcatctccga cccaaccaat caacaccctt gactcactgg ccttccccct c ccaccaaat 180 tatccttaaa aactctgatc cccgaatgct cagggagatc gatttgagta c taataagac 240 tccagtctcc tgcacaagca gctctgtgta ctcttcctct attgcaattc c tgtcttgat 300 aaatcggctc tgtgtaggcg gcggaagaag tgaacctgtt gggcggttac c acctctgtc 360 gtgtgtgaca gttgntttga atctctaatt gctcagtaca gatccacatg c aggttaagt 420 aagaagcttt tgaagaaaat ggaaagtctt aagtgatggc ttccaagaaa t caaacctac 480 attaattagg gaacaacgga ctttacgtat cacaaatgaa gagactgacn a agtaaatca 540 acttggcctt ttctta 556

```
<210> SEQ ID NO 157
<211> LENGTH: 333
<212> TYPE: DNA
<213> ORGANISM: Human
<220> FEATURE:
<221> NAME/KEY: modified_base
<222> LOCATION: (18)
<223> OTHER INFORMATION: Where n is a, c, g or t
<221> NAME/KEY: modified_base
<222> LOCATION: (40)
<223> OTHER INFORMATION: Where n is a, c, g or t
<221> NAME/KEY: modified_base
<222> LOCATION: (55)
<223> OTHER INFORMATION: Where n is a, c, g or t
<221> NAME/KEY: modified_base
<222> LOCATION: (57)
<223> OTHER INFORMATION: Where n is a, c, g or t
<221> NAME/KEY: modified_base
<222> LOCATION: (60)
<223> OTHER INFORMATION: Where n is a, c, g or t
<221> NAME/KEY: modified_base
<222> LOCATION: (91)
<223> OTHER INFORMATION: Where n is a, c, g or t
<221> NAME/KEY: modified_base
<222> LOCATION: (97)
<223> OTHER INFORMATION: Where n is a, c, g or t
<221> NAME/KEY: modified_base
<222> LOCATION: (103)
<223> OTHER INFORMATION: Where n is a, c, g or t
<221> NAME/KEY: modified_base
<222> LOCATION: (110)
<223> OTHER INFORMATION: Where n is a, c, g or t
<221> NAME/KEY: modified_base
<222> LOCATION: (161)
<223> OTHER INFORMATION: Where n is a, c, g or t
<221> NAME/KEY: modified_base
<222> LOCATION: (173)
<223> OTHER INFORMATION: Where n is a, c, g or t
<221> NAME/KEY: modified_base
<222> LOCATION: (193)
<223> OTHER INFORMATION: Where n is a, c, g or t
<221> NAME/KEY: modified_base
<222> LOCATION: (195)
<223> OTHER INFORMATION: Where n is a, c, g or t
<221> NAME/KEY: modified_base
<222> LOCATION: (196)
<223> OTHER INFORMATION: Where n is a, c, g or t
<221> NAME/KEY: modified_base
<222> LOCATION: (214)
<223> OTHER INFORMATION: Where n is a, c, g or t
<221> NAME/KEY: modified_base
<222> LOCATION: (231)
<223> OTHER INFORMATION: Where n is a, c, g or t
<221> NAME/KEY: modified_base
<222> LOCATION: (233)
<223> OTHER INFORMATION: Where n is a, c, g or t
<221> NAME/KEY: modified_base
<222> LOCATION: (238)
<223> OTHER INFORMATION: Where n is a, c, g or t
<221> NAME/KEY: modified_base
<222> LOCATION: (263)
<223> OTHER INFORMATION: Where n is a, c, g or t
<221> NAME/KEY: modified_base
<222> LOCATION: (264)
<223> OTHER INFORMATION: Where n is a, c, g or t
<221> NAME/KEY: modified_base
<222> LOCATION: (266)
<223> OTHER INFORMATION: Where n is a, c, g or t
<221> NAME/KEY: modified_base
<222> LOCATION: (283)
<223> OTHER INFORMATION: Where n is a, c, g or t
<221> NAME/KEY: modified_base
<222> LOCATION: (284)
<223> OTHER INFORMATION: Where n is a, c, g or t
<221> NAME/KEY: modified_base
<222> LOCATION: (287)
<223> OTHER INFORMATION: Where n is a, c, g or t
<221> NAME/KEY: modified_base
<222> LOCATION: (297)
```

<223> OTHER INFORMATION: Where n is a, c, g or t
<221> NAME/KEY: modified_base
<222> LOCATION: (298)
<223> OTHER INFORMATION: Where n is a, c, g or t
<221> NAME/KEY: modified_base
<222> LOCATION: (323)
<223> OTHER INFORMATION: Where n is a, c, g or t
<221> NAME/KEY: modified_base
<222> LOCATION: (331)
<223> OTHER INFORMATION: Where n is a, c, g or t

<400> SEQUENCE: 157

```
ggtccacaaa aatatatnaa ataagctgga tatataaaan caaacactta a catngncan     60

cattccttca gttattcaaa ctcactgata nctaacnggg agnagttggn a ttctggaag    120

acttcctaag ctaaaagtat atttacatat ttacaacaca ngtaaatata a cngaagaac    180

tacttcaaat aangnngaaa ttccagaatt ctanagattt atagctatag n tnacaanta    240

tcaccaattg gtttgcaatc aanngnccag cactacttat gannaangtt t aactannaa    300

accaaaaggg gagaaaacct ggnagggaaa nat                               333
```

<210> SEQ ID NO 158
<211> LENGTH: 629
<212> TYPE: DNA
<213> ORGANISM: Human
<220> FEATURE:
<221> NAME/KEY: modified_base
<222> LOCATION: (345)
<223> OTHER INFORMATION: Where n is a, c, g or t
<221> NAME/KEY: modified_base
<222> LOCATION: (565)
<223> OTHER INFORMATION: Where n is a, c, g or t

<400> SEQUENCE: 158

```
tcgagcggcc gcccgggcag gtctggtaca tttgtgcgag gtccggcact c tgttctcat     60

ccagtaagtg gtcgagccct ttctgcagaa ttgctgttaa atgttctcct a atagctgtt    120

tctccacaca agcaatcagt ggtttctgtg tgctgtggtc caagtaagtg a ttactctgt    180

ctccctcttc ttctaagcgt ttacttacat ggttaagata ttctggaacc t ctctttcct    240

gcattaacct ttggccttcg gcagcatata agcaattagt ctcttccaaa a atttcagtt    300

caaatgaatc tttatacacc tgcaggtcag acagcatgcc caggnaggct c cgcaacagg    360

ctccggtcca cggcctcgcc gctcctctcg cgctcgatca gcagtaggat t ccatcaatg    420

gttttactct gaaccatttt atcactaata atatgggttc taaacagttc t aatcccata    480

tcccagatgg agggcagcgt ggagttctgc agcacatagg tgcggtccaa g aacaggaag    540

atgcttctga tcatgaatca tttgnctggc aatggtcctg ccagcacgtg g taatctttc    600

ttttaaaaat aaacccttat ctaaacgtc                                    629
```

<210> SEQ ID NO 159
<211> LENGTH: 629
<212> TYPE: DNA
<213> ORGANISM: Human
<220> FEATURE:
<221> NAME/KEY: modified_base
<222> LOCATION: (33)
<223> OTHER INFORMATION: Where n is a, c, g or t
<221> NAME/KEY: modified_base
<222> LOCATION: (546)
<223> OTHER INFORMATION: Where n is a, c, g or t
<221> NAME/KEY: modified_base
<222> LOCATION: (576)
<223> OTHER INFORMATION: Where n is a, c, g or t

<400> SEQUENCE: 159

```
tcgagcggcc gcccgggcag gttctagagg ganaatctgg ctgatttggg a ataaaatat     60

aatcgaatat tcaacaccat gaagataaat cttattttgg aaatctactg a ccttaatac    120

cccaagcttg ccctgaatac tttgattgga attggaatat atcaaaaaag g ttagtattt    180

ttgttgtagt taggatacta aaaggatatt agttacccaa gagatccaat t tgtttttct    240

gatgaatagt gttcagtaaa atgaagcagt cttaagagtg actaataatt t caaagtgat    300

ttttcgtcta ttcttaatat tttttaatta tttattttta agagttttat a ccttgagca    360

gatacaatga tccgctttag tgagaggaca atttctgatt gattgttttc t cttcaggcc    420

atctcacctc ttcattctct tgttacattt gaagcagttg atataatggg t ttatacttt    480

aaaagataga catggtgcca tgaagtttgg ggaagttggg tgaattatcc c attctagtt    540

acagangagc tttccttaaa tgccctttac ttctangttt ggtcaagaag t cattttctg    600

agtaaaagtt attttcatat atgttgggg                                      629
```

```
<210> SEQ ID NO 160
<211> LENGTH: 519
<212> TYPE: DNA
<213> ORGANISM: Human
<220> FEATURE:
<221> NAME/KEY: modified_base
<222> LOCATION: (46)
<223> OTHER INFORMATION: Where n is a, c, g or t
<221> NAME/KEY: modified_base
<222> LOCATION: (309)
<223> OTHER INFORMATION: Where n is a, c, g or t
<221> NAME/KEY: modified_base
<222> LOCATION: (397)
<223> OTHER INFORMATION: Where n is a, c, g or t
<221> NAME/KEY: modified_base
<222> LOCATION: (430)
<223> OTHER INFORMATION: Where n is a, c, g or t
<221> NAME/KEY: modified_base
<222> LOCATION: (434)
<223> OTHER INFORMATION: Where n is a, c, g or t
<221> NAME/KEY: modified_base
<222> LOCATION: (471)
<223> OTHER INFORMATION: Where n is a, c, g or t
<221> NAME/KEY: modified_base
<222> LOCATION: (497)
<223> OTHER INFORMATION: Where n is a, c, g or t

<400> SEQUENCE: 160

tcgagcggcg cgcccgggca ggtctgctgg gattaatgcc aagttnttca g ccataaggt     60

agcgaaatct agcagaatcc agattacatc cacttccaat cacgcggtgt t tgggtaatc    120

cacttagttt ccagataaca tacgtaagaa tgtccactgg gttggaaacc a caattatga    180

tgcaatcagg actgtacttg acgatctgag gaataatgaa tttgaagaca t taacatttc    240

tctgcaccag attgagccga ctctcccctt cttgctgacg gactcctgca g ttaccacta    300

caatcttana attgggcggg tcacagaata atctttatct gccacaattt t aggtgctga    360

agaaataagc tcccatgctg cagatccatc atttctnctt taagcttatc t tccaaaaca    420

tccacaagan caangttcat cagccagaga ctttcccaga atgctgatag n acacgccat    480

accaacttgt ccaacancca ctacagcgat cttattggt                           519
```

```
<210> SEQ ID NO 161
<211> LENGTH: 446
<212> TYPE: DNA
<213> ORGANISM: Human
<220> FEATURE:
<221> NAME/KEY: modified_base
<222> LOCATION: (5)
```

<223> OTHER INFORMATION: Where n is a, c, g or t
<221> NAME/KEY: modified_base
<222> LOCATION: (32)
<223> OTHER INFORMATION: Where n is a, c, g or t
<221> NAME/KEY: modified_base
<222> LOCATION: (36)
<223> OTHER INFORMATION: Where n is a, c, g or t
<221> NAME/KEY: modified_base
<222> LOCATION: (269)
<223> OTHER INFORMATION: Where n is a, c, g or t
<221> NAME/KEY: modified_base
<222> LOCATION: (354)
<223> OTHER INFORMATION: Where n is a, c, g or t
<221> NAME/KEY: modified_base
<222> LOCATION: (381)
<223> OTHER INFORMATION: Where n is a, c, g or t

<400> SEQUENCE: 161

```
cgagnggccc gcccgggcag gtccagtaag cntttnacga tgatgggaaa g gttatgcaa     60

ggtcccagcg gtacaacgag ctgtttctac atcatttgta ttctgcatgg t acgtacaat    120

agcagacacc atctgaggag aacgcatgat agcgtgtctg gaagcttcct t tttagaaag    180

ctgatggacc ataactgcag ccttattaac caccacctgg tcctcgtcat t tagcagttt    240

tgtcagttca gggattgcac gtgtggcang ttctgcatca tcttgatagt t aatcaagtt    300

tacaactggc atgtttcagc atctgcgatg ggctcagcaa acgctggaca t tantgggat    360

gagcagcatc aaactgtgta natgggatct gcatgccctc atctaatgtc t cagggaaca    420

tagcagctcg taccctctga gctcga                                          446
```

<210> SEQ ID NO 162
<211> LENGTH: 354
<212> TYPE: DNA
<213> ORGANISM: Human
<220> FEATURE:
<221> NAME/KEY: modified_base
<222> LOCATION: (6)
<223> OTHER INFORMATION: Where n is a, c, g or t
<221> NAME/KEY: modified_base
<222> LOCATION: (19)
<223> OTHER INFORMATION: Where n is a, c, g or t
<221> NAME/KEY: modified_base
<222> LOCATION: (36)
<223> OTHER INFORMATION: Where n is a, c, g or t
<221> NAME/KEY: modified_base
<222> LOCATION: (126)
<223> OTHER INFORMATION: Where n is a, c, g or t
<221> NAME/KEY: modified_base
<222> LOCATION: (152)
<223> OTHER INFORMATION: Where n is a, c, g or t
<221> NAME/KEY: modified_base
<222> LOCATION: (174)
<223> OTHER INFORMATION: Where n is a, c, g or t
<221> NAME/KEY: modified_base
<222> LOCATION: (186)
<223> OTHER INFORMATION: Where n is a, c, g or t
<221> NAME/KEY: modified_base
<222> LOCATION: (196)
<223> OTHER INFORMATION: Where n is a, c, g or t
<221> NAME/KEY: modified_base
<222> LOCATION: (223)
<223> OTHER INFORMATION: Where n is a, c, g or t
<221> NAME/KEY: modified_base
<222> LOCATION: (249)
<223> OTHER INFORMATION: Where n is a, c, g or t

<400> SEQUENCE: 162

```
agcgtngtcg cggcccgang tcctgggaag cctttnttgc tgagcctcac a gcctctgtc     60

aggcggctgc ggatccagcg gtccaccagg ctctcatggc ctccgggctg g gaggngggt    120

gagggcacaa aacccttccc aaggccacga anggcaaact tggtggcatt c canagcttg    180
```

ttgcanaagt ggcggnaacc cagtatccgg ttcacatcca ggntgatgtc a cgaccctgg 240 gacatgtang cacataatcc aaaccggaga gcatcggtgc cacattcacg a atccccgct 300 gggaagtcag ctttctgccc ttctttggcc ttctccacct cgctgggatc c agg 354

<210> SEQ ID NO 163
<211> LENGTH: 258
<212> TYPE: DNA
<213> ORGANISM: Human
<220> FEATURE:
<221> NAME/KEY: modified_base
<222> LOCATION: (7)
<223> OTHER INFORMATION: Where n is a, c, g or t
<221> NAME/KEY: modified_base
<222> LOCATION: (24)
<223> OTHER INFORMATION: Where n is a, c, g or t
<221> NAME/KEY: modified_base
<222> LOCATION: (32)
<223> OTHER INFORMATION: Where n is a, c, g or t
<221> NAME/KEY: modified_base
<222> LOCATION: (153)
<223> OTHER INFORMATION: Where n is a, c, g or t
<221> NAME/KEY: modified_base
<222> LOCATION: (198)
<223> OTHER INFORMATION: Where n is a, c, g or t
<221> NAME/KEY: modified_base
<222> LOCATION: (205)
<223> OTHER INFORMATION: Where n is a, c, g or t

<400> SEQUENCE: 163
tttttcncca agtcctcttg ccgngggatc tngactgcaa tttaagacac t tctaattag 60 ttatacccag gccctgcaaa attgctgggt ttatataata tattcttgct g cacgaagat 120 ttattattct gttggatgat tctattttaa ttntatttat tctggccaaa a aagaacctt 180 ctccgctcgt caagagangc caatntgtct tgaaggacaa gagaaagatg c taacacaca 240 ctttcttctt cttgagga 258

<210> SEQ ID NO 164
<211> LENGTH: 282
<212> TYPE: DNA
<213> ORGANISM: Human
<220> FEATURE:
<221> NAME/KEY: modified_base
<222> LOCATION: (97)
<223> OTHER INFORMATION: Where n is a, c, g or t
<221> NAME/KEY: modified_base
<222> LOCATION: (130)
<223> OTHER INFORMATION: Where n is a, c, g or t
<221> NAME/KEY: modified_base
<222> LOCATION: (163)
<223> OTHER INFORMATION: Where n is a, c, g or t
<221> NAME/KEY: modified_base
<222> LOCATION: (178)
<223> OTHER INFORMATION: Where n is a, c, g or t
<221> NAME/KEY: modified_base
<222> LOCATION: (203)
<223> OTHER INFORMATION: Where n is a, c, g or t
<221> NAME/KEY: modified_base
<222> LOCATION: (204)
<223> OTHER INFORMATION: Where n is a, c, g or t

<400> SEQUENCE: 164
ggaacatatt acttttaaat tacttgggtc aatgaaacat ttaataaaaa c atttgcttc 60 tctatataat acgtatgtat aaaataagcc ttttcanaaa ctctggttct c ataatcctc 120 tataaatcan atgatctgac ttctaagagg aacaaattac agnaaggggt a tacattnat 180 gaatactggt agtactagag ganngacgct aaaccactct actaccactt g cggaactct 240

-continued cacagggtaa atgacaaagc caatgactga ctctaaaaac aa 282

<210> SEQ ID NO 165
<211> LENGTH: 462
<212> TYPE: DNA
<213> ORGANISM: Human
<220> FEATURE:
<221> NAME/KEY: modified_base
<222> LOCATION: (10)
<223> OTHER INFORMATION: Where n is a, c, g or t
<221> NAME/KEY: modified_base
<222> LOCATION: (33)
<223> OTHER INFORMATION: Where n is a, c, g or t
<221> NAME/KEY: modified_base
<222> LOCATION: (36)
<223> OTHER INFORMATION: Where n is a, c, g or t
<221> NAME/KEY: modified_base
<222> LOCATION: (49)
<223> OTHER INFORMATION: Where n is a, c, g or t
<221> NAME/KEY: modified_base
<222> LOCATION: (198)
<223> OTHER INFORMATION: Where n is a, c, g or t
<221> NAME/KEY: modified_base
<222> LOCATION: (222)
<223> OTHER INFORMATION: Where n is a, c, g or t
<221> NAME/KEY: modified_base
<222> LOCATION: (243)
<223> OTHER INFORMATION: Where n is a, c, g or t
<221> NAME/KEY: modified_base
<222> LOCATION: (278)
<223> OTHER INFORMATION: Where n is a, c, g or t
<221> NAME/KEY: modified_base
<222> LOCATION: (357)
<223> OTHER INFORMATION: Where n is a, c, g or t
<221> NAME/KEY: modified_base
<222> LOCATION: (385)
<223> OTHER INFORMATION: Where n is a, c, g or t
<221> NAME/KEY: modified_base
<222> LOCATION: (399)
<223> OTHER INFORMATION: Where n is a, c, g or t
<221> NAME/KEY: modified_base
<222> LOCATION: (405)
<223> OTHER INFORMATION: Where n is a, c, g or t
<221> NAME/KEY: modified_base
<222> LOCATION: (437)
<223> OTHER INFORMATION: Where n is a, c, g or t

<400> SEQUENCE: 165
gcccgggcan gtcctgtaat cccagctact cangangctg agtcatgana a tcgcctgaa 60 tccgggaggt agaggccgca gcgagcaaag attaagccac tgcactccag t ctgggtgac 120 agagtgagaa tctgtctgtt gctcctctgg cattggtctg aaatgggttt g tagaacatg 180 ccacagaagg accagcanca gcaacaaatg gatttgtgga angcgtagct c caaatggag 240 cangcacact tgatgaagca cgctgtgtct gtgcagangc aaccactggc a ctgttccaa 300 aaacattgct gctagcatta cttgtggaag tatacgcatt actggaggtg g ctgcanaac 360 tgaaaacgct gtctagttct gccanagctg catacttgnc tgaanatgca c ttgactgac 420 tgggaactga accacanaac caacaggacc tttacctgtg ga 462

<210> SEQ ID NO 166
<211> LENGTH: 365
<212> TYPE: DNA
<213> ORGANISM: Human
<220> FEATURE:
<221> NAME/KEY: modified_base
<222> LOCATION: (14)
<223> OTHER INFORMATION: Where n is a, c, g or t
<221> NAME/KEY: modified_base
<222> LOCATION: (18)
<223> OTHER INFORMATION: Where n is a, c, g or t

<400> SEQUENCE: 166

```
cgtgggtcgc ggcncgangt ctgaaaccaa tccagaacta aacatcagca c acaaaaaat     60

accaggatag atggaatcaa aagactctga agccaaaagg aggctaggga g agcaactga    120

acttagcaag ctgaggactt cagtgtccat catccgatcc tgccctgtaa c aacaggtct    180

atatgataga gatattccat ctgagctgga ggccattatc cttagcaaac t aacacagaa    240

cagaaaacca aatacatgtt ctcatttaga agtaggagct aaatgatgag a actcaagga    300

cacaaagaaa ggaacaacag acactggggc ctacttgagg gtggagggtg g gaggaggga    360

gaaga                                                                365
```

<210> SEQ ID NO 167
<211> LENGTH: 364
<212> TYPE: DNA
<213> ORGANISM: Human
<220> FEATURE:
<221> NAME/KEY: modified_base
<222> LOCATION: (19)
<223> OTHER INFORMATION: Where n is a, c, g or t
<221> NAME/KEY: modified_base
<222> LOCATION: (342)
<223> OTHER INFORMATION: Where n is a, c, g or t
<221> NAME/KEY: modified_base
<222> LOCATION: (361)
<223> OTHER INFORMATION: Where n is a, c, g or t

<400> SEQUENCE: 167

```
agcgtggtcg cggcgcgang tccagcccta gcttgcctgt gactccgcct t cactgggtg     60

ctctctctaa aagttgctga ctctttactg tatctcccaa ttcccactcc a ttggttcca    120

taaggggagg ggtgtctcac tcaacatggt gttcctggta ccaagaactg g ctgacgaag    180

ctgggtgccg tggctcatgc ctgtaatccc agcacttttg ggaggccaag a agggcggat    240

cacctgaggt ctggagttca agatcagcct gaccaacatg atgaaaccaa g tctccacta    300

aaaatataaa acaattagcc aggcatggtg gtgggtgcct gnaatcccag c tactgggga    360

ngct                                                                 364
```

<210> SEQ ID NO 168
<211> LENGTH: 447
<212> TYPE: DNA
<213> ORGANISM: Human
<220> FEATURE:
<221> NAME/KEY: modified_base
<222> LOCATION: (407)
<223> OTHER INFORMATION: Where n is a, c, g or t
<221> NAME/KEY: modified_base
<222> LOCATION: (414)
<223> OTHER INFORMATION: Where n is a, c, g or t
<221> NAME/KEY: modified_base
<222> LOCATION: (437)
<223> OTHER INFORMATION: Where n is a, c, g or t

<400> SEQUENCE: 168

```
cccgggcagg tcaaaaccca aaacctttca ttttagccca aaccagctca t gattaggta     60

tacaaggata acagaaccag ttgtcaggac gagcatttga caagtaaaag c aattcttgc    120

aaagctgcag ttcatccagc tcatggcatg tgtctttata tagcatcctc g caatgtcag    180

cttgctcact gtctgctcca tagaaaatca cggtattgtg gagaagcaat t gggcatcag    240

ctttgaactc ttcataactt cggtatttcc cttcattcac tttctcttga a tggtgggaa    300

cgtccacaga cctcggccgc gaccacgcta agcccgaatt ctgcagatat c catcacact    360

ggcggccgtt cgagcatggc atctagaagg cccaattcgc ctatagngag t cgnattacc    420
```

```
aattcactgg ccgtcgnttt acaacgc                                          447


<210> SEQ ID NO 169
<211> LENGTH: 524
<212> TYPE: DNA
<213> ORGANISM: Human
<220> FEATURE:
<221> NAME/KEY: modified_base
<222> LOCATION: (4)
<223> OTHER INFORMATION: Where n is a, c, g or t
<221> NAME/KEY: modified_base
<222> LOCATION: (6)
<223> OTHER INFORMATION: Where n is a, c, g or t
<221> NAME/KEY: modified_base
<222> LOCATION: (39)
<223> OTHER INFORMATION: Where n is a, c, g or t
<221> NAME/KEY: modified_base
<222> LOCATION: (40)
<223> OTHER INFORMATION: Where n is a, c, g or t
<221> NAME/KEY: modified_base
<222> LOCATION: (235)
<223> OTHER INFORMATION: Where n is a, c, g or t
<221> NAME/KEY: modified_base
<222> LOCATION: (248)
<223> OTHER INFORMATION: Where n is a, c, g or t
<221> NAME/KEY: modified_base
<222> LOCATION: (303)
<223> OTHER INFORMATION: Where n is a, c, g or t
<221> NAME/KEY: modified_base
<222> LOCATION: (340)
<223> OTHER INFORMATION: Where n is a, c, g or t
<221> NAME/KEY: modified_base
<222> LOCATION: (359)
<223> OTHER INFORMATION: Where n is a, c, g or t
<221> NAME/KEY: modified_base
<222> LOCATION: (382)
<223> OTHER INFORMATION: Where n is a, c, g or t
<221> NAME/KEY: modified_base
<222> LOCATION: (389)
<223> OTHER INFORMATION: Where n is a, c, g or t
<221> NAME/KEY: modified_base
<222> LOCATION: (420)
<223> OTHER INFORMATION: Where n is a, c, g or t
<221> NAME/KEY: modified_base
<222> LOCATION: (434)
<223> OTHER INFORMATION: Where n is a, c, g or t
<221> NAME/KEY: modified_base
<222> LOCATION: (442)
<223> OTHER INFORMATION: Where n is a, c, g or t
<221> NAME/KEY: modified_base
<222> LOCATION: (453)
<223> OTHER INFORMATION: Where n is a, c, g or t
<221> NAME/KEY: modified_base
<222> LOCATION: (496)
<223> OTHER INFORMATION: Where n is a, c, g or t

<400> SEQUENCE: 169

cgantngcgc gcccgggcag gtctgagcag cctttctgnn tgctggacta t tgggattgg     60

gttcatccaa cagagactgt atggatgtta gaatggaaga cacatcatag g ttggactcc    120

aacggttctg aagtatgtcc agacatatac taccatctgc atagactaag a acaaagaag    180

taggtacatt aaacgtaaca agaccactaa ggttttaaca ttatagacaa a acanaaata    240

gtcaaganta ctttgctttt gaagtttaaa gattcctatg ttgcttccca g ttaactgcc    300

taaaaagata agncataacc accactagtg aaataatcan gatgatcaga g aatgtcana    360

tgtgatcagt ataaaactgg angatattna gtgtcatcct ttggaaaagg c tgccctatn    420

atccaggaaa tcanaaacat tnttgaacag ggnccctagc tatccacaga c atgtgggaa    480

attcattccc caaatngtag gctggatccc ctatctgaaa taac                      524
```

<210> SEQ ID NO 170
<211> LENGTH: 332
<212> TYPE: DNA
<213> ORGANISM: Human
<220> FEATURE:
<221> NAME/KEY: modified_base
<222> LOCATION: (5)
<223> OTHER INFORMATION: Where n is a, c, g or t
<221> NAME/KEY: modified_base
<222> LOCATION: (10)
<223> OTHER INFORMATION: Where n is a, c, g or t
<221> NAME/KEY: modified_base
<222> LOCATION: (63)
<223> OTHER INFORMATION: Where n is a, c, g or t
<221> NAME/KEY: modified_base
<222> LOCATION: (66)
<223> OTHER INFORMATION: Where n is a, c, g or t
<221> NAME/KEY: modified_base
<222> LOCATION: (90)
<223> OTHER INFORMATION: Where n is a, c, g or t
<221> NAME/KEY: modified_base
<222> LOCATION: (93)
<223> OTHER INFORMATION: Where n is a, c, g or t
<221> NAME/KEY: modified_base
<222> LOCATION: (96)
<223> OTHER INFORMATION: Where n is a, c, g or t
<221> NAME/KEY: modified_base
<222> LOCATION: (186)
<223> OTHER INFORMATION: Where n is a, c, g or t
<221> NAME/KEY: modified_base
<222> LOCATION: (207)
<223> OTHER INFORMATION: Where n is a, c, g or t
<221> NAME/KEY: modified_base
<222> LOCATION: (261)
<223> OTHER INFORMATION: Where n is a, c, g or t
<221> NAME/KEY: modified_base
<222> LOCATION: (290)
<223> OTHER INFORMATION: Where n is a, c, g or t
<221> NAME/KEY: modified_base
<222> LOCATION: (324)
<223> OTHER INFORMATION: Where n is a, c, g or t
<221> NAME/KEY: modified_base
<222> LOCATION: (326)
<223> OTHER INFORMATION: Where n is a, c, g or t

<400> SEQUENCE: 170
tcgancggcn cgcccgggca ggtgacaaac ctgttattga agatgttggt t ctgatgagg 60 aanaanatca gaagggatgg tgacaagaan aanaanaaga agattaagga a aagtacatc 120 gatcaagaag agctcaacaa aacaaagccc atctggacca gaaatcccga c gatattact 180 aatgangagt acggagaatt ctataanagc ttgaccaatg actgggaaga t cacttggca 240 gtgaagcatt tttcagttga nggacagttg gaattcagag cccttctatn t gtcccacga 300 cgtgctcctt ttgatctgtt tganancaga aa 332

<210> SEQ ID NO 171
<211> LENGTH: 334
<212> TYPE: DNA
<213> ORGANISM: Human
<220> FEATURE:
<221> NAME/KEY: modified_base
<222> LOCATION: (5)
<223> OTHER INFORMATION: Where n is a, c, g or t
<221> NAME/KEY: modified_base
<222> LOCATION: (9)
<223> OTHER INFORMATION: Where n is a, c, g or t
<221> NAME/KEY: modified_base
<222> LOCATION: (200)
<223> OTHER INFORMATION: Where n is a, c, g or t
<221> NAME/KEY: modified_base
<222> LOCATION: (228)
<223> OTHER INFORMATION: Where n is a, c, g or t
<221> NAME/KEY: modified_base
<222> LOCATION: (232)

<223> OTHER INFORMATION: Where n is a, c, g or t

<400> SEQUENCE: 171
cgagnggcnc gcccgggcag gtctgttgat agcgacttaa cagaaaagtc t agacaaaca 60 taagcataaa aaattacagt ctttctaccc ttgggaatgg ggagaaaaag g aatctctac 120 cccaagacca gaaataataa gtcctgtttc tggtcctgaa catccagaat t atggaggct 180 ttggcctgac accacattan aatttggtct ggaaatcaaa ctttaganac a ngagatcgt 240 aagccatttt atactatcga cctaaattcc agtctaacgg ttcctttaca a agttgcgga 300 aagccctctt atatgctagc tgtaggaaat atag 334

<210> SEQ ID NO 172
<211> LENGTH: 439
<212> TYPE: DNA
<213> ORGANISM: Human
<220> FEATURE:
<221> NAME/KEY: modified_base
<222> LOCATION: (19)
<223> OTHER INFORMATION: Where n is a, c, g or t
<221> NAME/KEY: modified_base
<222> LOCATION: (375)
<223> OTHER INFORMATION: Where n is a, c, g or t
<221> NAME/KEY: modified_base
<222> LOCATION: (388)
<223> OTHER INFORMATION: Where n is a, c, g or t
<221> NAME/KEY: modified_base
<222> LOCATION: (390)
<223> OTHER INFORMATION: Where n is a, c, g or t
<221> NAME/KEY: modified_base
<222> LOCATION: (395)
<223> OTHER INFORMATION: Where n is a, c, g or t
<221> NAME/KEY: modified_base
<222> LOCATION: (409)
<223> OTHER INFORMATION: Where n is a, c, g or t
<221> NAME/KEY: modified_base
<222> LOCATION: (426)
<223> OTHER INFORMATION: Where n is a, c, g or t
<221> NAME/KEY: modified_base
<222> LOCATION: (434)
<223> OTHER INFORMATION: Where n is a, c, g or t

<400> SEQUENCE: 172
agcgtggtcg cggcccgang tctgcctata aaactagact tctgacgctg g gctccagct 60 tcattctcac aggtcatcat cctcatccgg gagagcagtt gtctgagcaa c ctctaagtc 120 gtgctcatac tgtgctgcca aagctgggtc catgacaact tctggtgggg c gagagcagg 180 catggcaaca aattccaagt tagggtctcc aatgagcttc ctagcaagcc a gaggaaggg 240 cttttcaaag ttgtagttac ttttggcaga aatgtcgtag tactgaagat t cttctttcg 300 gtggaagaca atggatttcg ccttcacttt ctgccttaat atccactttg g tgccacaca 360 acacaatggg gatgntttca cacacttngn accanatctc tatgccagnt a ggccatttt 420 ggaagnactt cganggtac 439

<210> SEQ ID NO 173
<211> LENGTH: 599
<212> TYPE: DNA
<213> ORGANISM: Human
<220> FEATURE:
<221> NAME/KEY: modified_base
<222> LOCATION: (5)
<223> OTHER INFORMATION: Where n is a, c, g or t
<221> NAME/KEY: modified_base
<222> LOCATION: (31)
<223> OTHER INFORMATION: Where n is a, c, g or t

<400> SEQUENCE: 173

```
cgatnggccg cccgggcagg tcctgtaaaa naggaaattc agacatcgta c gactcgtaa     60
ttgaatgtgg agctgactgc aatattttgt caaagcacca gaatagtgcc c tgcactttg    120
cgaagcagtc taacaatgtg cttgtgtacg acttgctgaa gaaccattta g agacacttt    180
caagagtagc agaagagaca ataaaggatt actttgaagc tcgccttgct c tgctagaac    240
cagtttttcc aatcgcatgt catcgactct gtgagggtcc agatttttca a cagatttca    300
attaccaacc cccacagaac ataccagaag gctctggcat cctgctgttt a tcttccatg    360
caaacttttt gggtaaagaa gttattgctc ggctctgtgg accgtgtagt g tacaagctg    420
tagttctgaa tgataaattt cagcttcctg tttttctggg tctcgctctg t tgtccaggc    480
tggagtgcag tggcgcggat tacagctcac tggagtcttg acttcccagg c acaagcaat    540
cctcccacct cagcctccta actacctggg actaaaaatg caccgccacc a cattccgg     599
```

```
<210> SEQ ID NO 174
<211> LENGTH: 458
<212> TYPE: DNA
<213> ORGANISM: Human
<220> FEATURE:
<221> NAME/KEY: modified_base
<222> LOCATION: (30)
<223> OTHER INFORMATION: Where n is a, c, g or t
<221> NAME/KEY: modified_base
<222> LOCATION: (32)
<223> OTHER INFORMATION: Where n is a, c, g or t
<221> NAME/KEY: modified_base
<222> LOCATION: (35)
<223> OTHER INFORMATION: Where n is a, c, g or t
<221> NAME/KEY: modified_base
<222> LOCATION: (51)
<223> OTHER INFORMATION: Where n is a, c, g or t
<221> NAME/KEY: modified_base
<222> LOCATION: (61)
<223> OTHER INFORMATION: Where n is a, c, g or t
<221> NAME/KEY: modified_base
<222> LOCATION: (213)
<223> OTHER INFORMATION: Where n is a, c, g or t
<221> NAME/KEY: modified_base
<222> LOCATION: (261)
<223> OTHER INFORMATION: Where n is a, c, g or t
<221> NAME/KEY: modified_base
<222> LOCATION: (327)
<223> OTHER INFORMATION: Where n is a, c, g or t
<221> NAME/KEY: modified_base
<222> LOCATION: (347)
<223> OTHER INFORMATION: Where n is a, c, g or t
<221> NAME/KEY: modified_base
<222> LOCATION: (359)
<223> OTHER INFORMATION: Where n is a, c, g or t
<221> NAME/KEY: modified_base
<222> LOCATION: (377)
<223> OTHER INFORMATION: Where n is a, c, g or t
<221> NAME/KEY: modified_base
<222> LOCATION: (418)
<223> OTHER INFORMATION: Where n is a, c, g or t

<400> SEQUENCE: 174
```

```
tcgatttggc cgcccgggca ggtccatgcn gnttntgccc attcccatgg n gcccgacaa     60
ncccatcccc gaggccgaca tccccatgtt catgttcatg cccaccatgc c ctggctcat    120
ccctgcgctg ttccccagag gggccattcc catggtgccc gtcattacac c gggcatgtt    180
cataggcatg ggtcccccca ggagagggtt agnttgaggc cggacaggaa g catgtttga    240
tggagaactg aggttcacag nctccaaaac tttgagtcat cacattcata g gctgctgca    300
tattctgtct gctgaatcca ttgtatncag tgatggcctg ctggggnttt g gaaggctng    360
```

-continued

```
cataccaggt agtaagntcg tctaggctga tgtttacacc tggggtcaga c caagtanga    420

gggcaaggtt ttgctgactg attttctgga cccatatc                              458
```